US006255326B1

(12) United States Patent
Ashton et al.

(10) Patent No.: US 6,255,326 B1
(45) Date of Patent: *Jul. 3, 2001

(54) COMPOUNDS CONTAINING PHENYL LINKED TO ARYL OR HETEROARYL BY AN ALIPHATIC-OR HETEROATOM-CONTAINING LINKING GROUP

(75) Inventors: Michael John Ashton; David Charles Cook; Garry Fenton; Susan Jacqueline Hills; Ian Michael McFarlane; Andrew David Morley; Malcolm Norman Palfreyman; Andrew James Ratcliffe; Brian William Sharp; Sukanthini Thurairatnam; Bernard Yvon Jack Vacher; Nigel Vicker, all of Dagenham (GB)

(73) Assignee: Aventis Pharma Limited, West Malling (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/239,075

(22) Filed: Jan. 27, 1999

Related U.S. Application Data

(60) Continuation of application No. 09/239,075, filed on Jan. 27, 1999, now abandoned, which is a division of application No. 08/098,178, filed on Jul. 28, 1993, now Pat. No. 5,935,978, which is a continuation-in-part of application No. PCT/GB92/00153, filed on Jan. 28, 1992, now abandoned.

(30) Foreign Application Priority Data

| Jan. 28, 1991 | (GB) | 9101777 |
| Aug. 16, 1991 | (GB) | 9117727 |
| Jul. 28, 1992 | (GB) | 9216005 |
| Jul. 28, 1992 | (GB) | 9216006 |
| Jul. 28, 1992 | (GB) | 9216008 |
| May 21, 1993 | (GB) | 9310633 |
| Jul. 16, 1993 | (GB) | 9314847 |

(51) Int. Cl.[7] ......................... C07D 211/72; A61K 31/44
(52) U.S. Cl. ........................ 514/352; 546/309; 564/74; 564/182; 514/599; 514/617
(58) Field of Search ........................ 564/161, 182, 564/74; 546/309; 514/352, 599, 617

(56) References Cited

U.S. PATENT DOCUMENTS

| 4,263,311 | 4/1981 | Bender | 514/352 |
| 4,971,959 | 11/1990 | Hawkins | 514/352 |
| 5,250,549 | 10/1993 | Yoshino et al. | 514/352 |
| 5,274,002 | 12/1993 | Hawkins | 514/352 |
| 5,332,751 | 7/1994 | Yoshino et al. | 514/352 |

(List continued on next page.)

FOREIGN PATENT DOCUMENTS

| 0 470 805 A1 | 2/1992 | (EP) . |
| 0497564 | 5/1992 | (EP) . |
| 0 706 795 | 4/1996 | (EP) . |
| 0 232 199 B1 | 8/1987 | (FR) . |
| 2084140 | 4/1992 | (GB) . |
| 55/002214 | * 9/1980 | (JP) ........................ 564/161 |
| 58-69812 | 4/1983 | (JP) . |
| 62-158252 | 7/1987 | (JP) . |
| 4-360847 | 12/1992 | (JP) . |
| WO 92/12961 | 8/1982 | (WO) . |
| WO 91/15451 | 10/1991 | (WO) . |
| WO 92/00968 | 1/1992 | (WO) . |
| WO 92/02220 | 2/1992 | (WO) . |
| WO 92/07567 | 5/1992 | (WO) . |
| WO 92/19594 | 11/1992 | (WO) . |
| WO 93/07111 | 4/1993 | (WO) . |
| WO 93/19750 | 10/1993 | (WO) . |
| WO 93/25517 | 12/1993 | (WO) . |
| WO 94/12461 | 6/1994 | (WO) . |
| WO 95/01338 | 1/1995 | (WO) . |
| WO 96/00218 | 1/1996 | (WO) . |

OTHER PUBLICATIONS

Chugai Pharm., Hypoglycemic pharmaceuticals containing benzamide derivatives, Chemical Abstracts, vol. 99, No. 5, Abstract 43558z, p. 322 (Aug. 1983).

Sakakibara et al., Preparation of N–(4–pyridyl)benzamide derivatives as cardiotonics, Chemical Abstracts, vol. 108, No. 13, Abstract 112238p (Mar. 1988).

Sakakibara et al., Preparation of N–pyridyl–4–(benzyloxy-)benzamides as cardiotonics, Chemical Abstracts, vol. 108, No. 15, Abstract 131583p, p. 733 (Apr. 1988).

Lazer et al., Antiinflammatory 2,6–Di–tert–butyl–4(2–arylethenyl)phenols, J. Med. Chem., vol. 32, No. 1, 733 (1989).

Ichinohe et al., A convenient synthesis of isoquinoline alkaloids using catalytic methods, Chemical Abstracts, vol. 93, No. 9, Abstract 95456k, 666 (1980).

Sandstrom et al., Antiviral Therapy in AIDS, Drugs, vol. 34, 373 (1987).

Mathison et al., Synthesis and Hypotensive PRoperties of Tetrahydroiosquinolines, Journal of Medicinal Chemistry, vol. 16, No. 4, 332 (1973).

Navarro et al., Penloxifylline preferentially inhibits interleukin–10 production by HIV–1–infected human T cells, AIDS 1994, vol. 8, No. 8, 1192–1194.

(List continued on next page.)

Primary Examiner—Zinna Northington Davis
(74) Attorney, Agent, or Firm—Irving Newman

(57) ABSTRACT

This invention is directed to the pharmaceutical use of phenyl compounds, which are linked to an aryl moiety by various linkages, for inhibiting tumor necrosis factor. The invention is also directed to the compounds, their preparation and pharmaceutical compositions containing these compounds. Furthermore, this invention is directed to the pharmaceutical use of the compounds for inhibiting cyclic AMP phosphodiesterase.

22 Claims, No Drawings

U.S. PATENT DOCUMENTS

| | | | |
|---|---|---|---|
| 5,340,827 | 8/1994 | Beeley et al. | 514/352 |
| 5,362,915 | 11/1994 | Maachler et al. | 514/352 |
| 5,563,143 | 10/1996 | Cohan et al. | 514/352 |
| 5,679,696 | 10/1997 | Fenton et al. | 514/352 |
| 5,698,711 | 12/1997 | Palfreyman | 514/352 |
| 5,712,298 | 1/1998 | Amschler | 514/352 |
| 5,935,978 | 8/1999 | Fenton et al. | 514/352 |

OTHER PUBLICATIONS

Tilg et al., Immune Response Modulation b Pentoxifylline in Vitro, Transplantation, vol. 56, No. 1, 196–201 (1993).

Biswas et al., Cooperative inhibition of NJ–kB and Tat–inducted superactivation of human immunodeficiency virus type 1 long terminal repeat, Proc. Natl. Acad. Sci. USA, vol. 90, 11044–11048 (1993).

Fazley et al., Pentoxifylline (Trental) Decreases the Replication of the Human Immunodeficiency Virus Type 1 in Human Periphal Blood Mononuclear Cells and in Cultured T Cells, Blood, vol. 77, No. 8, 1653–1656 (1991).

Fauci, Multifactorial Nature of Human Immunodeficiency Virus Disease: Implications for Therapy, Science, vol. 262, 1011–1018 (1993).

Lowe, III et al., The PDE IV family of calcium–independent phosphodiesterase enzymes, Drugs of the Future 1992, vol. 17(9), 799–807.

Baum, Thalidomide blocks virus that causes AIDS, C&EN, p. 5, Jul. 12, 1993.

Grammaticakis, Contribution a l'etude de la'absorption dans l'ultraviolet moyen et le visible des N–aroyl–arylamines, Bull. Soc. Chim. Fr., 848–857 (1965).

* cited by examiner-

COMPOUNDS CONTAINING PHENYL LINKED TO ARYL OR HETEROARYL BY AN ALIPHATIC-OR HETEROATOM-CONTAINING LINKING GROUP

CROSS-REFERENCE TO RELATED APPLICATIONS

This application is a continuation application of U.S. patent application Ser. No. 09/239,075, filed Jan. 27, 1999, which is abandoned, in turn, is a divisional application of U.S. patent application Ser. No. 08/098,178, filed Jul. 28, 1993, now U.S. Pat. No. 5,935,978, in turn, is a continuation-in-part application of International Patent Application No. PCT/GB92/00153, filed Jan. 28, 1992, designating the United States as a Receiving Office, now abandoned.

FIELD OF THE INVENTION

This invention is directed to substituted phenyl compounds, their preparation, pharmaceutical compositions containing these compounds, and their pharmaceutical use in the treatment of disease states associated with proteins that mediate cellular activity.

Disease states associated with abnormally high physiological levels of cytokines such as TNF are treatable according to the invention. TNF is an important pro-inflammatory cytokine which causes hemorrhagic necrosis of tumors and possesses other important biological activities. TNF is released by activated macrophages, activated T-lymphocytes, natural killer cells, mast cells and basophils, fibroblasts, endothelial cells and brain astrocytes among other cells.

The principal in vivo actions of TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of TNF with poor prognosis in sepsis, graft versus host disease and acute respiratory distress syndrome, and its role in many other immunologic processes, this factor is regarded as an important mediator of general inflammation.

TNF primes or activates neutrophils, eosinophils, fibroblasts and endothelial cells to release tissue damaging mediators. TNF also activates monocytes, macrophages and T-lymphocytes to cause the production of colony stimulating factors and other pro-inflammatory cytokines such $IL_1$, $IL_6$, $IL_8$ and GM-CSF, which in some case mediate the end effects of TNF. The ability of TNF to activate T-lymphocytes, monocytes, macrophages and related cells has been implicated in the progression of Human Immunodeficiency Virus (HIV) infection. In order for these cells to become infected with HIV and for HIV replication to take place the cells must be maintained in an activated state. Cytokines such as TNF have been shown to activate HIV replication in monocytes and macrophages. Features of endotoxic shock such as fever, metabolic acidosis, hypotension and intravascular coagulation are thought to be mediated through the actions of TNF on the hypothalamus and in reducing the anti-coagulant activity of vascular endothelial cells. The cachexia associated with certain disease states is mediated through indirect effects on protein catabolism. TNF also promotes bone resorption and acute phase protein synthesis.

The discussion herein related to disease states associated with TNF include those disease states related to the production of TNF itself, and disease states associated with other cytokines, such as but not limited to IL-1, or IL-6, that are modulated by associated with TNF. For example, a IL-1 associated disease state, where IL-1 production or action is exacerbated or secreted in response to TNF, would therefore be considered a disease state associated with TNF. TNF-a and TNF-b are also herein referred to collectively as "TNF" unless specifically delineated otherwise, since the RE is a close structural homology between TNF-a (cachectin) and TNF-b (lymphotoxin) and each of them has a capacity to induce similar biologic responses and bind to the same cellular receptor.

Disease states associated with pathological conditions that are modulated by inhibiting enzymes, which are associated with secondary cellular messengers, such as cyclic AMP phosphodiesterase are also treatable according to the invention cyclic AMP phosphodiesterase is an important enzyme which regulates cyclic AMP levels and in turn thereby regulates other important biological reactions. The ability to regulate cyclic AMP phosphodiesterase, including type IV cyclic AMP phosphodiesterase, therefore, has been implicated as being capable of treating assorted biological conditions.

In particular, inhibitors of type IV cyclic AMP phosphodiesterase have been implicated as being bronchodilators and asthma-prophylactic agents and as agents for inhibiting eosinophil accumulation and of the function of eosinophils, and for treating other diseases and conditions characterized by, or having an etiology involving, morbid eosinophil accumulation. Inhibitors of cyclic AMP phosphodiesterase are also implicated in treating inflammatory diseases, proliferative skin diseases and conditions associated with cerebral metabolic inhibition.

Reported Developments

Chemical Abstracts, 108(15), Apr. 11, 1988, abstract no. 131583p pertains to an abstract of Japanese Patent Application Publication No. JP-A-62 158,253 which discloses that a substituted phenyl compound of formula

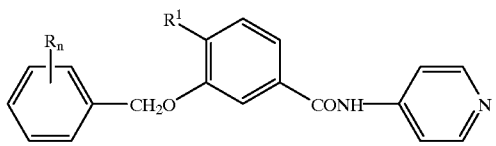

is a cardiotonic, but does not disclose or suggest that the compound inhibits cyclic AMP phosphodiesterase or TNF. JP-A-62 158,253 also does not disclose or suggest that the moiety that is ortho to $R^1$ may be anything other than benzyloxy.

Chemical Abstracts, 99(6), Aug. 8, 1983, abstract no. 43556z pertains to an abstract of Japanese Patent Application Publication No. JP-A-5 869,812 which discloses that a phenyl compound of formula

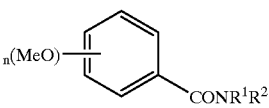

is a hypoglycemic agent, but does not disclose or suggest that the compound inhibits cyclic AMP phosphodiesterase or TNF. JP-A-5 869,812 also does not disclose or suggest that the benzamide moiety may be substituted by anything other than methoxy.

Panos Grammaticakis, *Bull. Soc. Chim. Fr.*, 848–857 (1965) discloses a phenyl compound of the formula

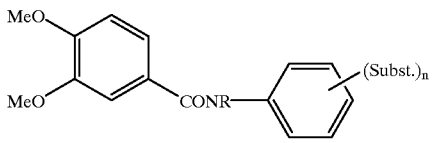

Grammaticakis examines the ultraviolet and visible absorbances of compounds bearing different substituents. Grammaticakis does not disclose or suggest that the compound exhibits any pharmacological activity.

Ian W. Mathison. et al., *J. Med. Chem.*, 16(4), 332–336 (1973), discloses that a phenyl compound of formula

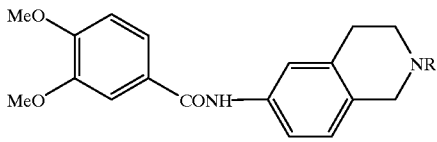

is a hypotensive agent, but do not disclose or suggest that the compound inhibits cyclic AMP phosphodiesterase or TNF. Mathison, et al., also do not disclose or suggest that the benzamide moiety may be substituted by anything other than methoxy.

European Patent Application Publication No. EP 232199 B1 discloses that phenyl compounds of formula

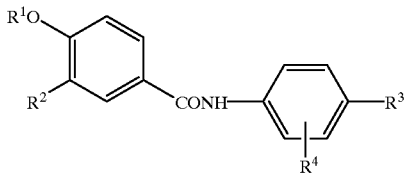

wherein $R^2$ is alkyl or mono- or polycyclic cycloalkyl, exhibit anti-inflammatory and/or anti-allergic activity. EP 232199 B1 does not disclose or suggest compounds wherein the $R^2$ substituent is bonded to the phenyl moiety via an oxygen or sulfur atom.

European Patent Application Publication No. EP 470,805 A1 discloses phenyl compounds of the formula

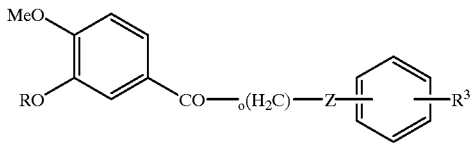

wherein R may be $C_{3-7}$ alkyl, $C_{3-7}$ cycloalkyl or

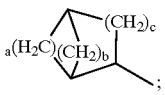

Z may be a bond; o is 1–4; a and b are independently 1–3; and c is 0–2. EP 470,805 A1 discloses that these compounds are useful intermediates for preparing PDE IV inhibitors, but does not disclose or suggest that the compounds have any pharmacological activity.

Japanese Patent Application Publication No. JP-A-0 4360847 discloses compounds of the formula

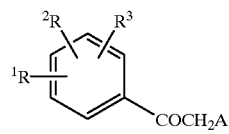

wherein $R^1$, $R^2$ and $R^3$ may be the same or different and may be optionally substituted lower alkyl(O); and A may be optionally substituted aryl or 5–6 membered heterocyclyl group. JP-A-0 4360847 discloses that the compounds are useful intermediates for preparing antimicrobial agents, but does not disclose or suggest that the compounds have any pharmacological activity.

WO Patent Application No. 92/12961 discloses that compounds of the formula

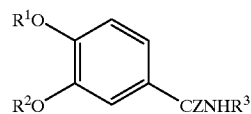

inhibit cyclic AMP phosphodiesterase. WO Patent Application No. 92/12961 does not disclose or suggest that these compound inhibit TNF. WO Patent Application No. 92/12961 also does not disclose compounds wherein $R^1$ is lower alkyl substituted by halo; or $R^2$ is alkyl substituted by halo, cycloalkyl or cycloalkenyl, alkenyl, cycloalkyl substituted by halo, methylene or alkyl, cycloalkenyl, cyclothioalkyl or cyclothioalkenyl; or $R^1$ or $R^2$ attached to the phenyl through sulfur; or $R^3$ is aryl or heteroaryl each of which is substituted by aralkoxy, aralkylthio, carboxy, aralkyloxycarbonyl, $Y^1Y^2N-$, $Y^1Y^2NCO-$ or $Y^1Y^2NSO_2-$ where $Y^1$ and $Y^2$ are independently hydrogen, alkyl, aryl or aralkyl provided that one or both of $Y^1$ and $Y^2$ is aryl or aralkyl.

SUMMARY OF THE INVENTION

This invention is directed to the pharmaceutical use of a compound of formula I below to inhibit the production or physiological effects of TNF in the treatment of a patient suffering from a disease state associated with a physiologically detrimental excess of tumor necrosis factor (TNF), where formula I is as follows:

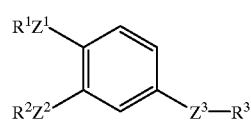

I wherein
$R^1$ is lower alkyl;
$R^2$ is alkyl, alkenyl, cycloalkyl, cycloalkenyl, cyclothioalkyl or cyclothioalkenyl;
$R^3$ is aryl or heteroaryl;
Z, $Z^1$ and $Z^2$ are independently oxygen or sulfur;
$Z^3$ is $-CH=CH-$, $-C\_C-$, $-CH_2-CZ-$, $-CZCH_2-$, $-CZ-CZ-$, $-CH_2-NH-$, $-CH_2-O-$, $-CH_2-S-$, $-CX_2-O-$, $-CZNH-$, $-NH-CH_2-$, $-O-CH_2-$, $-SCH_2-$, $-SOCH_2-$, $-SO_2CH_2-$, $-O-CX_2-O-$ CZ—, —NH—CZ—, —N=N—, —NH—SO$_2$—, —SO$_2$—NH—, —CZ—CZ—NH—, —NH—CO—O—, —O—CO—NH— or —NH—CO—NH—; and X is halo;

or an N-oxide thereof or a pharmnaceutically acceptable salt thereof.

Compounds within the scope of the present invention also inhibit cyclic AMP phosphodiesterase, and are useful in treating a disease state associated with pathological conditions that are modulated by inhibiting cyclic AMP phosphodiesterase, such disease states including inflammatory and autoimmune diseases, in particular type IV cyclic AMP phosphodiesterase.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Alkyl" means an aliphatic hydrocarbon group which may be straight or branched having about 1 to about 15 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl group may be substituted by one or more halo, cycloalkyl or cycloalkenyl. Exemplary alkyl groups include methyl, fluoromethyl, difluoromethyl, trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl.

"Alkenyl" means an aliphatic hydrocarbon group containing a carbon—carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo. Exemplary alkenyl groups include ethenyl, propenyl, n-butenyl, i-butenyl, 3-methylbut-2-enyl, n-pentenyl, heptenyl, octenyl and decenyl.

"Cycloalkyl" means a non-aromatic mono- or multicyclic ring system of about 3 to about 10 carbon atoms. Preferred monocyclic cycloalkyl rings include cyclopentyl, fluorocyclopentyl, cyclohexyl and cycloheptyl; more preferred is cyclopentyl. The cycloalkyl group may be substituted by one or more halo, methylene (H$_2$C=) or alkyl. Exemplary multicyclic cycloalkyl rings include 1-decalin, adamant-(1- or 2-)yl and norbornyl.

"Cycloalkenyl" means a non-aromatic monocyclic or multicyclic ring system containing a carbon—carbon double bond and having about 3 to about 10 carbon atoms. Preferred monocyclic cycloalkenyl rings include cyclopentenyl, cyclohexenyl or cycloheptenyl; more preferred is cyclopentenyl. A preferred multicyclic cycloalkenyl ring is norbornylenyl. The cycloalkenyl group may be substituted by one or more halo, methylene (H$_2$C=) or alkyl.

"Cyclothioalkyl" means a non-aromatic monocyclic or multicyclic ring system of about 3 to about 10 ring atoms. Preferred rings include about 5 to about 6 ring atoms wherein one of the ring atoms is sulfur. The cyclothioalkyl may be optionally substituted by one or more halo. Preferred monocyclic cyclothioalkyl rings include tetrahydrothiophenyl and tetrahydrothiopyranyl; more preferred is tetrahydrothiophenyl. The thio moiety of the cyclothioalkyl may also be optionally oxidized to the corresponding S-oxide or S,S-dioxide.

"Cyclothioalkenyl" means a non-aromatic monocyclic or multicyclic ring system containing a carbon—carbon double bond and having about 3 to about 10 ring atoms. Preferred rings include about 5 to about 6 ring atoms and wherein one of the ring atoms is sulfur. The cyclothioalkenyl may be optionally substituted by one or more halo. Preferred monocyclic cyclothioalkyl rings include dihydrothiophenyl and dihydrothiopyranyl; more preferred is dihydrothiophenyl. The thio moiety of the cyclothioalkyl may also be optionally oxidized to the corresponding S-oxide or S,S-dioxide "Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, alkyl, aryl, aralkyl, hydroxy, hydroxyalkyl, alkoxy, aryloxy, aralkoxy, carboxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, arylthio, aralkylthio, $Y^1Y^2N$—, $Y^1Y^2NCO$— or $Y^1Y^2NSO_2$—, where $Y^1$ and $Y^2$ are independently hydrogen, alkyl, aryl, and aralkyl. Preferred aryl group substituents include hydrogen, alkyl, hydroxy, acyl, aroyl, halo, nitro, cyano, alkoxycarbonyl, acylamino, alkylthio, $Y^1Y^2N$—, $Y^1Y^2NCO$— or $Y^1Y^2NSO_2$—, where $Y^1$ and $Y^2$ are independently hydrogen and alkyl.

"Heteroaryl" means about a 5- to about a 10-membered aromatic monocyclic or multicyclic hydrocarbon ring system in which one or more of the carbon atoms in the ring system is/are element(s) other than carbon, for example nitrogen, oxygen or sulfur. The "heteroaryl" may also be substituted by one or more aryl group substituents. Exemplary heteroaryl groups include pyrazinyl, furanyl, thienyl, pyridyl, pyrimidinyl, isoxazolyl, isothiazolyl, quinolinyl, and isoquinolinyl. Preferred heteroaryl groups include pyrazinyl, thienyl, pyridyl, pyrimidinyl, isoxazolyl and isothiazolyl.

"Aralkyl" means an aryl-alkyl-group in which the aryl and alkyl are as previously described. Preferred aralkyls contain a lower alkyl moiety. Exemplary aralkyl groups include benzyl, 2-phenethyl and naphthlenemethyl.

"Hydroxyalkyl" means a HO-alkyl-group in which alkyl is as previously defined. Preferred hydroxyalkyls contain lower alkyl. Exemplary hydroxyalkyl groups include bydroxymethyl and 2-hydroxyethyl.

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and palmitoyl.

"Aroyl" means an aryl-CO— group in which the aryl group is as previously described. Exemplary groups include benzoyl and 1- and 2-naphthoyl.

"Alkoxy" means an alkyl-O— group in which the alkyl group is as previously described. Exemplary alkoxy groups include methoxy, ethoxy, n-propoxy, i-propoxy, n-butoxy and heptoxy.

"Aryloxy" means an aryl-O— group in which the aryl group is as previously described. Exemplary aryloxy groups include phenoxy and naphthoxy.

"Aralkyloxy" means an aralkyl-O— group in which the aralkyl groups is as previously described. Exemplary aralkyloxy groups include benzyloxy and 1- or 2-naphthalenemethoxy.

"Alkylthio" means an alkyl-S— group in which the alkyl group is as previously described. Exemplary alkylthio groups include methylthio, ethylthio, i-propylthio and heptylthio.

"Arylthio" means an aryl-S— group in which the aryl group is as previously described. Exemplary arylthio groups include phenylthio and naphthylthio.

"Aralkylthio" means an aralkyl-S— group in which the aralkyl group is as previously described. An exemplary aralkylthio group is benzylthio.

"$Y^1Y^2N$—" means a substituted or unsubstituted amino group, wherein $Y^1$ and $Y^2$ are as previously described. Exemplary groups include amino ($H_2N$—), methylamino, ethylmethylamino, dimethylamino and diethylamino.

"Alkoxycarbonyl" means an alkyl-O—CO— group. Exemplary alkoxycarbonyl groups include methoxy- and ethoxycarbonyl.

"Aryloxycarbonyl" means an aryl-O—CO— group. Exemplary aryloxycarbonyl groups include phenoxy- and naphthoxycarbonyl.

"Aralkoxycarbonyl" means an aralkyl-O—CO— group. An exemplary aralkoxycarbonyl group is benzyloxycarbonyl.

"$Y^1Y^2NCO$—" means a substituted or unsubstituted carbamoyl group, wherein $Y^1$ and $Y^2$ are as previously described. Exemplary groups are carbamoyl ($H_2NCO$—) and dimethylcarbamoyl ($Me_2NCO$—).

"$Y^1Y^2NSO_2$—" means a substituted or unsubstituted sulfamoyl group, wherein $Y^1$ and $Y^2$ are as previously described. Exemplary groups are sulfamoyl ($H_2NSO_2$—) and dimethylsulfamoyl ($Me_2NSO_2$—).

"Acylamino" is an acyl-NH— group wherein acyl is as defined herein.

"Aroylamino" is an aroyl-NH— group wherein aroyl is as defined herein.

"Alkylsulfonyl" means an alkyl-$SO_2$— group. Preferred groups are those in which the alkyl group is lower alkyl.

"Alkylsulfinyl" means an alkyl-SO— group. Preferred groups are those in which the alkyl group is lower alkyl.

"Arylsulfonyl" means an aryl-$SO_2$— group.

"Arylsulfinyl" means an aryl-SO— group.

"Halo" means fluoro, chloro, bromo, or iodo. Preferred are fluoro, chloro or bromo, and more preferred are fluoro or chloro.

Preferred Embodiments

A compound of formula I is preferred for use in treating a disease state associated with a physiologically detrimental excess of tumor necrosis factor.

Disease states associated with pathological conditions that are modulated by inhibiting cyclic AMP phosphodiesterase are also preferably treated with a compound of formula I.

According to the compound aspect of the invention, preferred compounds are described by formula I, provided that when $R^1$ is methyl, $R^2$ is cyclopentyl, $Z^1$ and $Z^2$ are oxygen and $R^3$ is phenyl, then $Z^3$ is other than —$COCH_2$—.

More preferred compounds of the present invention include those wherein $R^2$ is norbornyl, norbornenyl, cyclopentyl and cyclopentenyl; preferably cyclopentyl, norbornyl and norbornenyl.

According to a further aspect of the invention, more preferred compounds of formula I are described wherein $Z^1$ and $Z^2$ are oxygen, or $Z^1$ is sulfur and $Z^2$ is oxygen are preferred. More preferred are where $Z^1$ and $Z^2$ are oxygen.

Compounds of the invention wherein $R^1$ is substituted by halo, preferably fluoro, are also preferred. It is further preferred that the halo substitution is on positions of the $R^1$ that are adjacent to the position of $R^1$ that is attached respectively to $Z^1$.

Among the compounds of the invention where $R^3$ is substituted phenyl the phenyl group is preferably substituted on the 2-position or on both the 2- and 6-positions.

Similarly, among compounds of the invention where $R^3$ is substituted heteroaryl, the heteroaryl group is preferably substituted on one or both, more preferably on both. of the positions adjacent to the position of $R^3$ that is attached to $Z^3$. Further preferred are compounds wherein $R^3$ is a 3,5-dihalopyrid-4-yl moiety or an N-oxide thereof.

Special embodiments of the compounds of the invention include those of formula I wherein $Z^3$ is —CZNH—; and $R^1$ is lower alkyl optionally substituted by halo.

Special embodiments of the compounds also include those of formula I wherein $Z^3$ is —CZNH—; and $R^2$ is alkenyl, alkyl optionally substituted by halo, cycloalkyl or cycloalkenyl, cyclothioalkyl, cyclothioalkenyl, cycloalkenyl optionally substituted by halo, methylene or alkyl or cycloalkyl optionally substituted by halo, methylene or alkyl. Further preferred are compounds including those of formula I wherein $Z^3$ is —CZNH—; and $R^2$ is cyclothioalkyl, cycloalkenyl optionally substituted by halo or methylene, cycloalkyl optionally substituted by halo, or alkyl optionally substituted halo.

Special embodiments of the compounds also include those of formula I wherein $Z^3$ is —$CZCH_2$—; and $R^2$ is alkenyl, alkyl optionally substituted by halo, cycloalkyl or cycloalkenyl, cyclothioalkyl, cyclothioalkenyl, cycloalkenyl optionally substituted by halo, methylene or alkyl or cycloalkyl optionally substituted by halo, methylene or alkyl. Further preferred are compounds including those of formula I wherein $Z^3$ is —$CZCH_2$—; and $R^2$ is cycloalkenyl, cycloalkyl optionally substituted by halo, or alkyl optionally substituted halo.

Another special embodiment of the compounds of the present invention include those wherein $Z^3$ is —CZNH—; and $R^3$ is aryl or heteroaryl each of which is substituted by aralkoxy, aralkylthio, carboxy, aralkyloxy-carbonyl, $Y^1Y^2N$—, $Y^1Y^2NCO$— or $Y^1Y^2NSO_2$— where $Y^1$ and $Y^2$ are independently hydrogen, alkyl, aryl or aralkyl, provided that one or both of $Y^1$ and $Y^2$ is aryl or aralkyl.

Another special embodiment of the compounds of the present invention include those wherein $Z^3$ is —CZNH—; and $Z^1$ and $Z^2$ are oxygen or sulfur and at least one of $Z^1$ and $Z^2$ is sulfur; more preferred only one of $Z^1$ and $Z^2$ is sulfur; and further preferred $Z^1$ is sulfur and $Z^2$ is oxygen.

A compound of formula I wherein $Z^3$ is is —CH═CH—, —C≡C—, —$CH_2$—CZ—, —CZ—CZ—, —$CH_2$—NH—, —$CH_2$—O—, —$CH_2$—S—, —$CX_2$—O—, —NH—$CH_2$—, —O—$CH_2$—, —$SCH_2$—, —$SOCH_2$—, —$SO_2CH_2$—, —O—$CX_2$—, —O—CZ—, —NH—CZ—, —N═N—, —NH—$SO_2$—, —$SO_2$—NH—, —CZ—CZ—

NH—, —NH—CO—O—, —O—CO—NH— or —NH—CO—NH— is another special embodiment of the compounds of the present invention. More preferred are compounds wherein $Z^3$ is —O—CH$_2$—, —O—CZ—, —NH—CZ—, —NH—CO—NH—, —CH$_2$—NH—, —CH=CH—, —SO$_2$—NH—, —N=N— or —CZ—CZ—.

Preferred compounds for use according to the invention are selected from the following:

A N-(2,6-difluorophenyl)-3-cyclopentyloxy-4-methoxybenzamide;
B N-(2-chloro-6-fluorophenyl)-3-cyclopentyloxy-4-methoxybenzamide;
C N-(2-trifluoromethylphenyl)-3-cyclopentyloxy-4-methoxybenzamide;
D N-(2,4,6-trichlorophenyl)-3-cyclopentyloxy-4-methoxybenzamide;
E N-(2,6-dibromophenyl)-3-cyclopentyloxy-4-methoxybenzamide;
F N-(2-chloro-6-methylphenyl)-3-cyclopentyloxy-4-methoxybenzamide;
G N-(2,6-dichlorophenyl)-3-cyclopentyloxy-4-methoxybenzamide;
H N-(2-fluorophenyl)-3-cyclopentyloxy-4-methoxybenzamide;
I N-phenyl-3-cyclopentyloxy-4-methoxybenzamide;
J N-(2-methoxyphenyl)-3-cyclopentyloxy-4-methoxybenzamide;
K N-(2-chlorophenyl)-3-cyclopentyloxy-4-methoxybenzamide;
L N-(3-chlorophenyl)-3-cyclopentyloxy-4-methoxybenzamide;
M N-(4-methoxyphenyl)-3-cyclopentyloxy-4-methoxybenzamide;
N N-(2,6-dimethylphenyl)-3-cyclopentyloxy-4-methoxybenzamide;
O N-(2-methylthiophenyl)-3-cyclopentyloxy-4-methoxybenzamide;
P N-(2-bromophenyl)-3-cyclopentyloxy-4-methoxybenzamide;
Q N-(2-methoxycarbonylphenyl)-3-cyclopentyloxy-4-methoxybenzamide;
R N-(2-aminosulfonylphenyl)-3-cyclopentyloxy-4-methoxybenzamide;
S N-(2-benzoylphenyl)-3-cyclopentyloxy-4-methoxybenzamide;
T N-(2-cyanophenyl)-3-cyclopentyloxy-4-methoxybenzamide;
U N-(2,5-dichlorophenyl)-3-cyclopentyloxy-4-methoxybenzamide;
V N-(3-methylphenyl)-3-cyclopentyloxy-4-mnethoxybenzamide;
W N-(2-nitrophenyl)-3-cyclopentyloxy-4-methoxybenzamide;
X N-(2-dimethylaminophenyl)-3-cyclopentyloxy-4-methoxybenzamide;
Y N-(2-acetylphenyl)-3-cyclopentyloxy-4-methoxybenzamide;
Z N-(2-hydroxyphenyl)-3-cyclopentyloxy-4-methoxybenzamide;
AA N-(2-methylsulfonylphenyl)-3-cyclopentyloxy-4-methoxybenzamide;
AB N-(2,6-difluorophenyl)-3-cyclohexyloxy-4-methoxybenzamide;
AC N-(2,6-difluorophenyl)-3-butoxy-4-methoxybenzamide;
AD N-(2,6-difluorophenyl)-3-propoxy-4-methoxybenzamide;
AE N-(2-chlorophenyl)-3-cyclopentyloxy-4-rmethoxy(thiobenzamide);
AF N-(4-chloropyrid-3-yl)-3-cyclopentyloxy-4-methoxybenzamide;
AG N-pyrid-2-yl-3-cyclopentyloxy-4-methoxybenzamide;
AH N-pyrazin-2-yl-3-cyclopentyloxy-4-methoxybenzamide;
AI N-pyrimidin-2-yl-3-cyclopentyloxy-4-methoxybenzamide;
AJ N-(3-methylpyrid-2-yl)-3-cyclopentyloxy-4-methoxybenzamide;
AK N-pyrid-3-yl-3-cyclopentyloxy-4-methoxybenzamide;
AL N-(3-chloropyrid-2-yl)-3-cyclopentyloxy-4-methoxybenzarmide;
AM N-(3-chloropyrid-4-yl)-3-cyclopentyloxy-4-methoxybenzamide;
AN N-pyrid-4-yl-3-cyclopentyloxy-4-methoxybenzamide;
AO N-(3,5-dichloropyrid-4-yl)-3-cyclopentyloxy-4-methoxybenzamide;
AP N-(3,5-dimethyisoxazol-4-yl)-3-cyclopentyloxy4-nethoxybenzamide;
AQ N-(4,6-dichloropyrmid-5-yl)-3-cyclopentyloxy-4-methoxybenzamide,
AR N-(4-nitrophenyl)-3-cyclopentyloxy-4-nethoxybenzamide;
AS N-(2,3,5,6-tetrafluoropyrid-4-yl)-3-cyclopentyloxy-4-methoxybenzamide;
AT N-(3,5-dichloropyrid-4-yl)-3-cyclopentyloxy-4-methoxybenzamide;
AU N-(2,4,6-trifluorophenyl)-3-cyclopentyloxy-4-methoxybenzamide;
AV 3,5-dichloro-4-(3-cyclopentyloxy-4-methoxybenzamido)pyridine-N-oxide;
AW N-(3,5-dichloropyrid-4-yl)-3-(exo-8,9,10-trinorbornyl-2-oxy)-4-methoxybenzamide;
AX N-(3,5-dichloropyrid-4-yl)-3-cyclohexyloxy-4-methoxybenzamide;
AY N-(3,5-dibromopyrid-4-yl)-3-cyclopentyloxy-4-methoxybenzamide;
AZ N-(3,5-dichloropyrid-4-yl)-3-butoxy-4-methoxybenzamide;
BA N-(3-methyl-5-bromoisothiazol-4-yl)-3-cyclopentyloxy-4-methoxybenzamide;
BB N-(3,5-dimethylisothiazol-4-yl)-3-cyclopentyloxy-4-methoxybenzamide;
BC N-(3,5-dimethylpyrid-4-yl)-3-cyclopentyloxy-4-methoxybenzamide;
BD N-(5-cyano-3-methylisothiazol-4-yl)-3-cyclopentyloxy-4-methoxybenzamide;
BE N-(3,5-dichloropyrid-4-yl)-3-cyclopentyloxy-4-methoxy(thiobenzamide);
BF N-(2,6-dichloro-4-methoxyphenyl)-3-cyclopentyloxy-4-methoxybenzamide;

BG N-(2,6-dichloro-4-cyanophenyl)-3-cyclopentyloxy-4-methoxybenzamide;
BH N-(2,6-dichloro-4-carbamoylphenyl)-3-cyclopentyloxy-4-methoxybenzamide;
BI N-(2,6-dichloro-4-aminophenyl)-3-cyclopentyloxy-4-methoxybenzamide;
BJ N-(3-chloro-2,5,6-trifluoropyrid-4-yl)-3-cyclopentyloxy-4-methoxybenzamide;
BK N-(3,5-dibromopyrid-4-yl)-3-butoxy-4-methoxybenzamide;
BL N-(2,6-dichloro-4-methoxycarbonylphenyl)-3-cyclopentyloxy-4-methoxybenzamide;
BM N-(4-acetylamino-2,6-dichlorophenyl)-3-cyclopentyloxy-4-methoxybenzamide;
BN N-(3,5-dichloropyrid-4-yl)-3-nonyloxy-4-methoxybenzamide;
BO N-(2,6-dichloro-4-formylphenyl)-3-cyclopentyloxy-4-methoxybenzamide;
BP N-(2,6-dichlorophenyl)-3-(exo-8,9,10-trinorbornyl-2-oxy)-4-methoxybenzamide;
BQ N-(2,3,5-trifluoropyrid-4-yl)-3-cyclopentyloxy-4-methoxybenzamide;
BR sodium salt of N-(3,5-dichloropyrid-4-yl)-3-cyclopentyloxy-4-methoxybenzamide;
BS N-(2,6-dichloro-4-ethoxycarbonylphenyl)-3-cyclopentyloxy-4-methoxybenzamide;
BT N-(2,6-dichloro-4-hydroxymethylphenyl)-3-cyclopentyloxy-4-methoxybenzamide;
BU N-(3,5-dichloropyrid-4-yl)-3-dodecyloxy-4-methoxybenzamide;
BV (R)-N-(3,5-dichloropyrid-4-yl)-3-(exo-8,9,10-trinorbornyl-2-oxy)-4-methoxybenzamide;
BW (S)-N-(3,5-dichloropyrid-4-yl)-3-(exo-8,9,10-trinorbornyl-2-oxy)-4-methoxybenzamide;
BX N-(2,6-dichloro-4-nitrophenyl)-3-cyclopentyloxy-4-methoxybenzamide;
BY N-(3,5-dichloropyrid-4-yl)-3-cyclopentyloxy-4-(methylthio)benzamide;
BZ N-(3,5-difluoropyrid-4-yl)-3-cyclopentyloxy-4-(methylthio)benzamide;
CA N-(3,5-dichloropyrid-4-yl)-3-(exo)-8,9 10-trinorbornyl-2-oxy-4-(methylthio)benzamide;
CB (R)-N-(3,5-dichloropyrid-4-yl)-3-(exo)-8,9,10-trinorbornyl-2-oxy-4-(methylthio)benzamide;
CC (S)-N-(3,5-dichloropyrid-4-yl)-3-(exo)-8,9,10-trinorbornyl-2-oxy-4-(methylthio)benzamide;
CD (±)-N-(3,5-dichloropyrid-4-yl)-3-cyclopent-2-enyloxy-4-methoxybenzamide;
CE N-(3,5-dichloropyrid-4-yl)-3-cyclopent-3-enyloxy-4-methoxybenzamide;
CF N-(3,5-dichloropyrid-4-yl)-3-cyclopentyloxy-4-difluoromethoxybenzamide;
CG 3-cyclopentylthio-N-(3,5-dichloropyrid-4-yl)-4-methoxybenzamide;
CH N-(3,5-dichloropyrid-4-yl)-3-isopropylthio-4-methoxybenzamide;
CI N-(3,5-dichloropyrid-4-yl)-3-cyclopentyloxy-4-(fluoromethylthio)benzamide;
CJ 3-cyclopentyloxy-4-methoxypheny 2',6'-dichlorobenzyl ketone;
CK 3-cyclopentyloxy-4-methoxyphenyl 3,5-dichloropyrid-4-ylmethyl ketone;
CL 3,5-dichloro-4-(2-(3-cyclopentyloxy-4-methoxyphenyl)-2-oxoethyl)pyridine-N-oxide;
CM 1-(3-cyclopentyloxy-4-methoxyphenyl)-2-(3-chloropyrid-4-yl)ethanone;
CN 1-(3-cyclopentyloxy-4-methoxyphenyl)-2-(4-pyridyl)ethanone;
CO 1-(3-cyclopentyloxy-4-methoxyphenyl)-2-phenylethanone;
CP 3-(3-methyl-2-butenyloxy)-N-(3,5-dichloropyrid-4-yl)-4-methoxybenzamide;
CQ N-(3,5-dichloropyrid-4-yl)-3-[exobicyclo(2.2.1)hept-5-en-2-yloxy]-4-methoxybenzamide;
CR N-(3-cyclopentyloxy-4-methoxyphenyl)-2,6-dichlorobenzamide;
CS N-(3-cyclopentyloxy-4-methoxyphenyl)-2,6-difluorobenzamide;
CT N-(2,6-dichlorophenyl)-N'-(3-cyclopentyloxy-4-methoxyphenyl)urea;
CU N-(3,5-dichloropyrid-4-yl)-N'-(3-cyclopentyloxy-4-methoxyphenyl)urea;
CV (3-cyclopentyloxy-4-methoxyphenyl)-2,6-dichlorobenzoate;
CW 3-cyclopentyloxy-4-methoxyphenyl-2,6-dichlorobenzyl ether;
CX N-(2-chlorophenyl)-3-cyclopentyloxy-4-methoxybenzylamine;
CY 1-(3-cyclopentyloxy-4-methoxyphenyl)-2-(2,6-dichlorophenyl)ethene;
CZ 1-(3-cyclopentyloxy-4-methoxyphenyl)-2-(2,6-difluorophenyl)ethene;
DA 1-(3-cyclopentyloxy-4-methoxyphenyl)-2-(pyrid-4-yl)ethane-1,2-dione;
DB trans-1-(3-cyclopentyloxy-4-methoxyphenyl)-2-(3,5-dichloropyrid-4-yl)-diazene;
DC 1-(3-cyclopentyloxy-4-methoxyphenyl)-c-1-oxo-r-2-(3,5-dichloro-1-oxo-pyrid-4-yl)diazene;
DD trans-1-(3-cyclopentyloxy-4-methoxyphenyl)-2-(3,5-dichloro-1-oxo-pyrid-4-yl)diazene;
DE N-(2-chlorophenyl)-3-cyclopentyloxy-4-methoxybenzenesulfonamide;
DF 3-cyclopentyloxy-N-(3,5-difluoropyrid-4-yl)-4-methoxybenzamide;
DG (R)-N-(2,6-dichlorophenyl)-3-(exo-8,9,10-trinorbornyl-2-oxy)-4-methoxybenzamide;
DH (S)-N-(2,6-dichlorophenyl)-3-(exo-8,9,10-trinorbornyl-2-oxy)-4-methoxybenzamide;
DI 3-cyclopentylmethoxy-N-(3,5-dichloropyrid-4-yl)-4-methoxybenzamide;
DJ 3-cyclopropylmethoxy-N-(3,5-dichloropyrid-4-yl)-4-methoxybenzamide;
DK N-(3-bromo-5-chloropyrid-4-yl)-3-cyclopentyloxy-4-methoxybenzamide;
DL N-(3,5-dichloropyrid-4-yl)-3-isopropoxy-4-methoxybenzamide;
DM 3-tert-butoxy-N-(3,5-dichloropyrid-4-yl)-4-methoxybenzamide;
DN N-(3,5-dichloropyrid-4-yl)-4-methoxy-3-(pent-3-yloxy)benzamide;
DO N-(3,5-dichloropyrid-4-yl)-3-cyclopentyloxy-4-trifluoromethoxybenzamide;
DP N-(3,5-dichloropyrid-4-yl)-3-(4,4-difluoro-3-methylenecyclobut-1-enyloxy)-4-methoxybenzamide;

DQ  N-(3,5-difluoropyrid-4-yl)-3-isopropoxy-4-difluoromethoxybenzamide;
DR  N-(3,5-difluoro-1-oxido-4-pyridinio)-3-isopropoxy-4-difluoromethoxybenzamide;
DS  N-(3,5-dichloro-pyrid-4-yl)-3-isopropoxy-4-difluoromethoxybenzamide;
DT  N-(3,5-dichloro-1-oxido-4-pyridinio)-3-isopropoxy-4-difluoromethoxybenzamide;
DU  N-(3,5-dichloro-4-pyridyl)-4-difluoromethoxy-3-(exo)-8,9,10-trinorborn-2-yloxybenzamide;
DV  N-(3,5-dichloro-1-oxido-4-pyridinio)-4-difluoromethoxy-3-(exo)-8,9,10-trinorborn-2-yloxybenzamide;
DW  N-(3,5-dichloropyrid-4-yl)-3-(2-fluorocyclopentyloxy)-4-methoxybenzamide;
DX  N-(3,5-dichloro-pyrid-4-yl)-3-(tetrahydrothiophen-3-oxy)-4-methoxybenzamide;
DY  3-cyclopentyloxy-N-(3,5-dichloro-1-oxido-4-pyridinio)-4-difluoromethoxybenzamide;
DZ  N-(3,5-dichloropyrid-4-yl)-3-isopropoxy-4-(methylthio)benzamide;
EA  N-(3,5-difluoropyrid-4-yl)-3-isopropoxy-4-(methylthio)benzamide;
EB  N-(3,5-dichloropyrid-4-yl)-3-(pent-3-yloxy)-4-(methylthio)benzamide;
EC  (±)-1-[3-{(exo)-8,9,10-trinorbornyl-2-oxy}-4-methoxyphenyl]-2-(3,5-dichloropyrid-4-yl)ethanone;
ED  1-[-cyclopentyloxy-4-(methylthio)phenyl]-2-(3,5-dichloropyrid-4-yl)-ethanone;
EE  1-(4-methoxy-3-prop-2-yloxyphenyl)-2-(3,5-dichloropyrid-4-yl)ethanone;
EF  1-(4-methylthio-3-prop-2-yloxyphenyl)-2-(3,5-dichloropyrid-4-yl)ethanone;
EG  1-(4-methoxy-3-prop-2-yloxyphenyl)-2-(3,5-dichloro-1-oxido-4-pyridinio)ethanone;
EH  1-(3-cyclopentyloxy-4-difluoromethoxyphenyl)-2-(3,5-dichloropyrid-4-yl)ethanone;
EI  1-(3-cyclopentyloxy-4-difluoromethoxyphenyl)-2-(3,5-dichloro-1-oxido-4-pyridinio)ethanone;
EJ  2-(3,5-dichloropyrid-4-yl)-1-[3-{exobicyclo(2.2.1)hept-5-en-2-yloxy}-4-methoxyphenyl]ethanone;
EK  2-(3,5-dichloro-4-pyridyl)-1-(4-difluoromethoxy-3-(exo)-8,9,10-trinorborn-2-yloxyphenyl)ethanone;
EL  2-(3,5-dichloro-1-oxido-4-pyridinio)-1-[4-difluoromethoxy-3-(exo)-8,9,10-trinorbom-2-yloxyphenyl]ethanone;
EM  2-(3,5-dichloro-4-pyridyl)-1-[4-methoxy-3-(3-methyl-2-butenyloxy)phenyl]ethanone;
EN  2-(3,5-dichloro-4-pyridyl)-1-(4-difluoromethoxy-3-isopropoxyphenyl)ethanone;
EO  2-(3,5-dichloro-1-oxido-4-pyridinio)-1-(4-difluoromethoxy-3-isopropoxyphenyl)ethanone;
EP  3,5-dichloro-4-(3-cyclopentyloxy-4-methoxyphenoxymethyl)pyridine; and
EQ  N-(3,5-dichloro-1-oxido-4-pyridinio-4-methoxy-3-(exo)-8,9,10-trinorborn-2-yloxy-benzamide.

Preferred compounds include AO, AV, AW, BV, BW, BY, CF, CK, CL, CQ, DU, EC, EJ, EK, EL and EQ.

The letters A to EQ are allocated to compounds for easy reference in this specification.

Compounds of formula I may be prepared by the application or adaptation of known methods, by which is meant methods used heretofore or described in the literature.

Thus, compounds of formula I

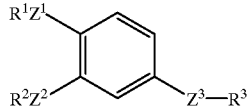

wherein $R^1$, $R^2$, $R^3$, $Z^1$ and $Z^2$, are as hereinbefore defined, $Z^3$ represents a —CZNH— linkage, and Z represents oxygen, may be prepared by the reaction of compounds of formula II

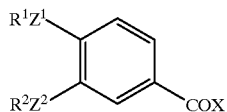

hereinafter depicted, wherein $R^1$, $R^2$, $Z^1$ and $Z^2$ are as hereinbefore defined and X represents halo, e.g. bromo or, preferably, chloro, with compounds of the formula III $R^3NH_2$   III wherein $R^3$ is as hereinbefore defined, preferably in the presence of a base such as an alkali metal hydride, e.g. sodium hydride, or an amine, preferably a tertiary amine, e.g. triethylamine or pyridine, optionally in an inert solvent, for example dichloromethane, dimethylformamide, or an ether, e.g. diethyl ether or tetrahydrofuran, preferably at a temperature from 0° C. to the reflux temperature or at the melting point of the reaction mixture.

Alternatively, compounds of formula I, wherein $R^1$, $R^2$ and $R^3$, are as hereinbefore defined, Z, $Z^1$ and $Z^2$ are oxygen, and $Z^3$ represents a —CZNH— linkage, may be prepared by the reaction of compounds of formula I'

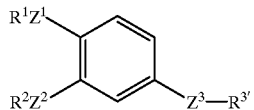

hereinafter depicted, wherein $R^1$ and $R^2$ are as hereinbefore defined, $R^{3'}$ is hydrogen, Z, $Z^1$ and $Z^2$ are oxygen and $Z^3$ represents a —CZNH— linkage, with compounds of the formula V'

$R^3X$   V' wherein $R^3$ and X are as hereinbefore defined. preferably X is chloro, and preferably the preparation takes place in the presence of a base, for example an alkali metal hydride, e.g. sodium hydride, an alkali metal alkoxide, e.g. potassium t-butoxide, an alkali metal hydroxide, e.g. sodium hydroxide or carbonate, or an amine, preferably a tertiary amine, e.g. triethylamine or pyridine, optionally in an inert solvent, for example dichloromethane, dimethylformamide, or an ether, e.g. diethyl ether or tetrahydrofuran, preferably at a temperature from 0° C. to the reflux temperature.

Alternatively, compounds of formula I, wherein $R^1$, $R^2$, $R^3$, Z, $Z^1$ and $Z^2$, are as hereinbefore defined, $Z^3$ represents a —CZNH— linkage, may be prepared by the reaction of compounds of formula IV

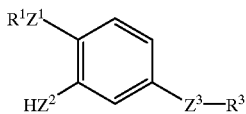

IV hereinafter depicted, wherein $R^1$, $R^3$, Z, $Z^1$ and $Z^2$ are as hereinbefore defined and $Z^3$ represents a —CZNH— linkage, with compounds of the formula V $R^2X$      V wherein $R^2$ is as hereinbefore defined, preferably, X is as hereinbefore defined or p-toluenesulfonate, preferably X is bromo, and preferably the preparation takes place in the presence of a base, for example an alkali metal hydride, e.g. sodium hydride, an alkali metal hydroxide or carbonate, e.g. sodium hydroxide or carbonate, or an amine, preferably a tertiary amine, e.g. triethylamine or pyridine, optionally in an inert solvent, for example dichloromethane, dimethylformamide or an ether, e.g. diethyl ether or tetrahydrofuran, preferably at a temperature from 0° C. to the reflux temperature.

Alternatively, compounds of formula I, wherein $R^1$, $R^2$, $R^3$, $Z^1$ and $Z^2$, are as hereinbefore defined, $Z^3$ represents a —CZCH$_2$— linkage, and Z represents oxygen, are prepared from compounds of formula VI

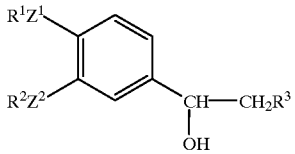

VI wherein $R^1$, $R^2$, $R^3$, $Z^1$ and $Z^2$ are as hereinbefore defined, by oxidation by the application or adaptation of known methods. The oxidation is carried out, for example, by reaction with oxalyl chloride and dimethyl sulfoxide, in a solvent such as dichloromethane, and preferably at a temperature lower than −65° C. Alternatively, the oxidation is carried out by reaction with chromium trioxide in the presence of 3,5-dimethylpyrazole.

According to a further feature of the present invention, compounds of formula I, wherein $R^1$, $R^2$, $R^3$, Z, $Z^1$ and $Z^2$, are as hereinbefore defined, $Z^3$ represents a —CZCH$_2$— linkage, and preferably those wherein Z represents oxygen, are prepared from compounds of formula VII

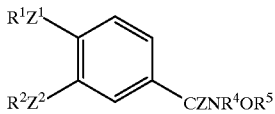

VII wherein $R^1$, $R^2$, Z, $Z^1$ and $Z^2$ are as hereinbefore defined and $R^4$ and $R^5$ represent lower alkyl, e.g. methyl, groups, by coupling with compounds of the formula VIII $R^3CH_3$      VIII wherein $R^3$ is as hereinbefore defined, in the presence of a strong base such as lithium diisopropylamide (usually prepared in situ from butyl lithium and diisopropylamine), preferably at a low temperature.

According to a feature of the present invention, compounds of formula I, wherein $R^1$, $R^2$, $R^3$, $Z^1$ and $Z^2$, are as hereinbefore defined, $Z^3$ represents a —CZCH$_2$— linkage, and Z represents oxygen, are prepared by the reaction of compounds of formula IX

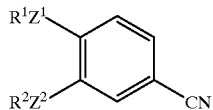

IX wherein $R^1$, $R^2$, $Z^1$ and $Z^2$ are as hereinbefore defined, with compounds of the formula X $R^3MgX$      X wherein $R^3$ and X are as hereinbefore defined.

Alternatively, compounds of formula I, wherein $R^1$, $R^2$, $R^3$, $Z^1$ and $Z^2$ are as hereinbefore defined and $Z^3$ represents an —O—CH2— linkage are prepared by the reaction of compounds of the formula XI

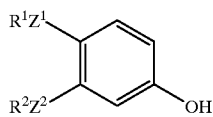

XI wherein $R^1$, $R^2$, $Z^1$ and $Z^2$ are as hereinbefore defined, with compounds of the formula XII $R^3CH_2X^2$      XII wherein $R^3$ and X are as hereinbefore defined, and X is preferably chloro, preferably takes place in the presence of a base such as an alkali metal carbonate, e.g. potassium carbonate, preferably in a solvent such as dimethylformamide.

According to a further feature of the present invention, compounds of formula I, wherein $R^1$, $R^2$, $R^3$, $Z^1$ and $Z^2$ are as hereinbefore defined and $Z^3$ represents an —O—CO— linkage are prepared by the reaction of compounds of formula XI above, wherein $R^1$, $R^2$, $Z^1$ and $Z^2$ are as hereinbefore defined, with compounds of the formula XIII $R^3COX$      XIII wherein $R^3$ and X are as hereinbefore defined, and X is preferably chloro, preferably in the presence of a base such as a tertiary amine, e.g. triethylamine, preferably in a solvent such as dichloromethane.

According to a further feature of the present invention, compounds of formula I, wherein $R^1$, $R^2$, $R^3$, $Z^1$ and $Z^2$ are as hereinbefore defined and $Z^3$ represents an —NH—CO— linkage are prepared by the reaction of compounds of formula XIV

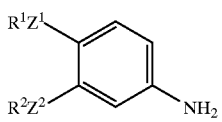

XIV wherein $R^1$, $R^2$, $Z^1$ and $Z^2$ are as hereinbefore defined, with compounds of formula XIII above, wherein $R^3$ and $X^2$ are as hereinbefore defined, preferably in the presence of a base such as a tertiary amine, e.g. triethylamine, preferably in a solvent such as dichloromethane.

According to a further feature of the present invention, compounds of formula I, wherein $R^1$, $R^2$, $R^3$, $Z^1$ and $Z^2$ are as hereinbefore defined and $Z^3$ represents an —NH—CO—NH— linkage are prepared by the reaction of compounds of formula XIV above, wherein $R^1$, $R^2$, $Z^1$ and $Z^2$ are as hereinbefore defined, with compounds of the formula XV

XV wherein $R^3$ is as hereinbefore defined, preferably in the presence of a base such as a tertiary amine, e.g. triethylamine, preferably in a solvent such as dichloromethane.

According to a further feature of the present invention, compounds of formula I, wherein $R^1$, $R^2$, $R^3$, $Z^1$ and $Z^2$ are as hereinbefore defined and $Z^3$ represents an —NH—CO—NH— linkage are prepared by the reaction of compounds of formula XIV, wherein $R^1$ $R^2$, $Z^1$ and $Z^2$ are as hereinbefore defined, with compounds of the formula III above, wherein R3 is as hereinbefore defined, preferably by reacting the compound of formula XIV with phosgene or, preferably, bis(trichloromethyl) carbonate, and by then reacting the product of that reaction with the cation derived from the compound of formula III (for example by reaction with a base such as sodium hydride). The reactions are preferably carried out in suitable solvents such as dichloromethane and tetrahydrofuran.

According to a further feature of the present invention, compounds of formula I, wherein $R^1$, $R^2$, $R^3$, $Z^1$ and $Z^2$ are as hereinbefore defined and $Z^3$ represents a —CH2—NH— linkage are prepared by the reaction of compounds of formula XVI

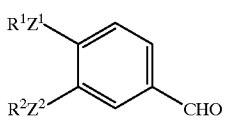

XVI wherein $R^1$, $R^2$, $Z^1$ and $Z^2$ are as hereinbefore defined, with compounds of formula III above, wherein $R^3$ is as hereinbefore defined, followed by reduction with a compound such as sodium cyanoborohydride. This process is especially suitable for compounds wherein $R^3$ represents an optionally substituted phenyl or naphthyl group.

According to a further feature of the present invention, compounds of formula I, wherein $R^1$, $R^2$, $R^3$, $Z^1$ and $Z^2$ are as hereinbefore defined and $Z^3$ represents a —CH2—NH— linkage are prepared by the reaction of compounds of formula XVII

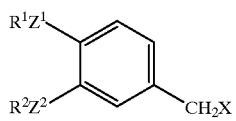

XVII wherein X, $R^1$, $R^2$, $Z^1$ and $Z^2$ are as hereinbefore defined, and X is preferably bromo, with compounds of formula above, wherein $R^3$ is as hereinbefore defined, preferably in the presence of a base such as sodium hydride. This process is especially suitable for compounds wherein $R^3$ represents an optionally substituted heteroaryl group.

According to a further feature of the present invention, compounds of formula I, wherein $R^1$, $R^2$, $R^3$, $Z^1$ and $Z^2$ are as hereinbefore defined and $Z^3$ represents a trans —CH═CH— linkage are prepared by the reaction of compounds of formula XVI above, wherein $R^1$, $R^2$, $Z^1$ and $Z^2$ are as hereinbefore defined, with the reaction product of a compound of the formula XVIII $(R^4PCH_2R^3)^+(X)^-$      XVIII (wherein $R^3$ is as hereinbefore defined, $R^4$ represents an aryl e.g. phenyl group, and X represents halo, preferably bromo) with a base such as an alkali metal alkoxide, e.g. potassium t-butoxide. The reaction is preferably carried out in a solvent such as tetrahydrofuran.

According to a further feature of the present invention, compounds of formula I, wherein $R^1$, $R^2$, $R^3$, $Z^1$ and $Z^2$ are as hereinbefore defined and $Z^3$ represents an —SO₂—NH— linkage are prepared by the reaction of compounds of formula XIX

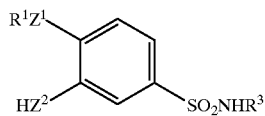

XIX wherein $R^1$, $R^3$, $Z^1$ and $Z^2$ are as hereinbefore defined, with compounds of the formula V $R^2X$      V wherein $R^2$ and X are as hereinbefore defined, preferably after treatment with a base such as sodium hydride, preferably in a solvent such as dimethylformamide.

According to a further feature of the present invention, compounds of formula I, wherein $R^1$, $R^2$, $R^3$, $Z^1$ and $Z^2$ are as hereinbefore defined and $Z^3$ represents an —S—CH2— linkage are prepared by the reaction of compounds of formula XX

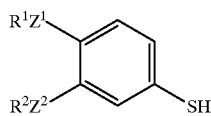

XX wherein $R^1$, $R^2$, $Z^1$ and $Z^2$ are as hereinbefore defined, with compounds of formula XII above, wherein $R^2$ and X are as hereinbefore defined, and preferably X is bromo, preferably after reaction with a base such as an alkali metal alkoxide, e.g. sodium methoxide.

According to a further feature of the present invention, compounds of formula I, wherein $R^1$, $R^2$, $R^3$, $Z^1$ and $Z^2$ are as hereinbefore defined and $Z^3$ represents a —CF2—O— linkage are prepared by the reaction of compounds of formula XXI

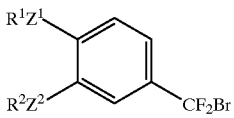

XXI wherein $R^1$, $R^2$, $Z^1$ and $Z^2$ are as hereinbefore defined, with compounds of the formula XXII R³OH                                                                                  XXII wherein $R^3$ is as hereinbefore defined, preferably with the aid of a base such as sodium hydride, preferably in a solvent such as tetrahydrofuran.

According to a further feature of the present invention, compounds of formula I, wherein $R^1$, $R^2$, $R^3$, $Z^1$ and $Z^2$ are as hereinbefore defined and $Z^3$ represents an —NH—CO—O— linkage are prepared by the reaction of compounds of formula XXIII

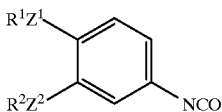

XXIII wherein $R^1$, $R^2$, $Z^1$ and $Z^2$ are as hereinbefore defined, with compounds of formula XII above, wherein $R^3$ is as hereinbefore defined, preferably with the aid of a base such as a tertiary amine, e.g. triethylamine, preferably in a solvent such as dichloromethane.

According to a further feature of the present invention, compounds of formula I, wherein $R^1$, $R^2$, $R^3$, $Z^1$ and $Z^2$ are as hereinbefore defined and $Z^3$ represents an —NH—CH$_2$— linkage are prepared by the reaction of compounds of formula XIV above, wherein $R^1$, $R^2$, $Z^1$ and $Z^2$ are as hereinbefore defined, with compounds of the formula XXIV R³CHO                                                                                XXIV wherein $R^3$ is as hereinbefore defined, preferably with the aid of a reducing agent such as sodium cyanoborohydride.

According to a further feature of the present invention, compounds of formula I, wherein $R^1$, $R^2$, $R^3$, $Z^1$ and $Z^2$ are as hereinbefore defined and $Z^3$ represents an —NH—SO$_2$— linkage are prepared by the reaction of compounds of formula XIV above, wherein $R^1$, $R^2$, $Z^1$ and $Z^2$ are as hereinbefore defined, with compounds of the formula XXV R³SO₂X                                                                               XXV wherein $R^3$ and X are as hereinbefore defined, preferably with the aid of a base such as a tertiary amine, e.g. triethylamine, preferably in a solvent such as tetrahydrofuran.

According to a further feature of the present invention, compounds of formula I, wherein $R^1$, $R^2$, $R^3$, $Z^1$ and $Z^2$ are as hereinbefore defined and $Z^3$ represents an —O—CO—NH— linkage are prepared by the reaction of compounds of formula XI above, wherein $R^1$, $R^2$, $Z^1$ and $Z^2$ are as hereinbefore defined, with compounds of formula XV above, wherein $R^3$ is as hereinbefore defined, or with a compound of formula III above, wherein $R^3$ is as hereinbefore defined, and phosgene or, preferably, bis(trichloromethyl) carbonate, preferably with the aid of a base such as a tertiary amine, e.g. triethylamine, preferably in a solvent such as dichloromethane.

According to a further feature of the present invention, compounds of formula I, wherein $R^1$, $R^2$, $R^3$, $Z^1$ and $Z^2$ are as hereinbefore defined and $Z^3$ represents an —O—CF$_2$— linkage are prepared by the reaction of compounds of formula XI above, wherein $R^1$, $R^2$, $Z^1$ and $Z^2$ are as hereinbefore defined, with compounds of the formula XXV R³CF₂Br                                                                              XXV wherein $R^3$ is as hereinbefore defined, preferably with the aid of a base such as sodium hydride, preferably in a solvent such as tetraliydrofuran.

According to a further feature of the present invention, compounds of formula I, wherein $R^1$, $R^2$, $R^3$, $Z^1$ and $Z^2$ are as hereinbefore defined and $Z^3$ represents an ethynyl linkage are prepared by the reaction of compounds of formula XXVI

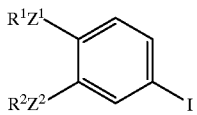

XXVI hereinafter depicted, wherein $R^1$, $R^2$, $Z^1$ and $Z^2$ are as hereinbefore defined, with compounds of the formula XXVII R³X¹                                                                                 XXVII wherein $R^3$ is as hereinbefore defined and $X^1$ represents an ethynyl group. Preferably the reaction is carried out with the aid of a catalyst e.g. palladium on carbon, and cuprous iodide, preferably with the aid of a base such as a tertiary amine, e.g. triethylamine, preferably in a solvent such as dimethylformamide.

According to a further feature of the present invention, compounds of formula I, wherein $R^1$, $R^2$, $R^3$, $Z^1$ and $Z^2$ are as hereinbefore defined and $Z^3$ represents a —CH$_2$—O— linkage are prepared by the reaction of compounds of formula XXVIII

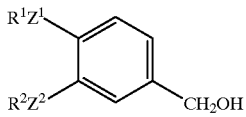

XXVIII wherein $R^1$, $R^2$, $Z^1$ and $Z^2$ are as hereinbefore defined, with compounds of the formula V above, wherein $R^3$ and X are as hereinbefore defined, preferably with the aid of a base such as an alkali metal alkoxide, e.g. potassium t-butoxide. The reaction is preferably carried out in a solvent such as tetrahydrofuran.

According to a further feature of the present invention, compounds of formula I, wherein $R^1$, $R^2$, $R^3$, $Z^1$ and $Z^2$ are as hereinbefore defined and $Z^3$ represents a —CH$_2$—O— linkage are prepared by the reaction of compounds of formula XVII above, wherein $R^1$, $R^2$, $Z^1$, $Z^2$ and X are as hereinbefore defined, with compounds of formula XXII above, wherein $R^3$ is as hereinbefore defined, preferably with the aid of a base such as an alkali metal alkoxide, e.g. potassium t-butoxide.

According to a further feature of the present invention, compounds of formula I, wherein $R^1$, $R^2$, $R^3$, $Z^1$ and $Z^2$ are as hereinbefore defined and $Z^3$ represents a —CO—CO—NH— linkage are prepared by the reaction of compounds of formula XXIX

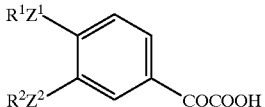

XXIX wherein $R^1$, $R^2$, $Z^1$ and $Z^2$ are as hereinbefore defined, with dichloromethyl methyl ether in dichloromethane, followed by reaction with compounds of formula III above, wherein $R^3$ is as hereinbefore defined, preferably with the aid of a base such as sodium hydride, preferably in a solvent such as tetrahydrofuran.

According to a further feature of the present invention, compounds of formula I, wherein $R^1$, $R^2$, $R^3$, $Z^1$ and $Z^2$ are as hereinbefore defined and $Z^3$ represents a —CO—CO— linkage are prepared by the oxidation of compounds of formula VI above, wherein $R^1$, $R^2$, $R^3$, $Z^1$ and $Z^2$ are as hereinbefore defined, for example by reaction with pyridinium dichromate, preferably in a solvent such as dichloromethane. This reaction is particularly suitable for compounds wherein $R^3$ represents a heteroaryl, preferably an optionally substituted pyridyl, group.

According to a further feature of the present invention, compounds of formula I, wherein $R^1$, $R^2$, $R^3$, $Z^1$ and $Z^2$ are as hereinbefore defined and $Z^3$ represents a trans —N=N— linkage are prepared by the reaction of compounds of formula XXX

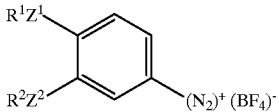

XXX wherein $R^1$ $R^2$, $R^3$, $Z^1$ and $Z^2$ are as hereinbefore defined, with compounds of the formula XXXI $R^3H$   XXXI wherein $R^3$ is as hereinbefore defined, preferably with the aid of a base such as lithium diisopropylamide.

According to a further feature of the present invention, compounds of formula I, wherein $R^1$, $R^2$, $R^3$, $Z^1$ and $Z^2$ are as hereinbefore defined and Z represents a —CH$_2$—S— linkage are prepared by the reaction of compounds of formula XVII, wherein X, $R^1$, $R^2$, $Z^1$ and $Z^2$ are as hereinbefore defined, with compounds of the formula XXXIII $R^3$—SH   XXXIII wherein $R^3$ is as hereinbefore defined, preferably with the aid of a base such as an alkali metal carbonate, e.g. potassium carbonate.

According to a further feature of the present invention, compounds of formula I, wherein $R^1$, $R^2$, $R^3$, $Z^1$ and $Z^2$ are as hereinbefore defined and $Z^3$ represents a —CH$_2$—CO— linkage are prepared by the oxidation of compounds of formula XXXIV

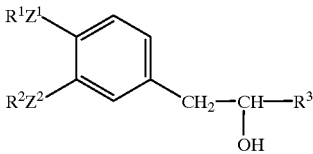

XXXIV wherein $R^1$, $R^2$, $R^3$, $Z^1$ and $Z^2$ are as hereinbefore defined. The oxidation is carried out, for example, by reaction with oxalyl chloride and dimethyl sulfoxide, in a solvent such as dichloromethane, and preferably at a temperature lower than −65° C. Alternatively, the oxidation is carried out by reaction with chromium trioxide in the presence of 3,5-dimethylpyrazole.

As another example, compounds of formula I wherein $R^1$, $R^2$, $R^3$, $Z^1$ and $Z^2$ are as hereinbefore defined, and $Z^3$ represents a cis —C=C— or cis —N=N— linkage are prepared by the action of ultraviolet radiation upon their trans-isomers.

As another example, compounds of formula I wherein $R^1$, $R^2$, $R^3$, $Z^1$ and $Z^2$ are as hereinbefore defined, $Z^1$ and $Z^2$ preferably each represent oxygen, and $Z^3$ represents an —SO—CH$_2$— linkage are prepared by the oxidation of corresponding compounds wherein $Z^3$ represents an —S—CH$_2$— linkage. For example, the oxidation can be carried out by means of potassium hydrogen peroxomonosulfate in a medium such as aqueous methanol.

As another example, compounds of formula I wherein $R^1$, $R^2$, $R^3$, $Z^1$ and $Z^2$ are as hereinbefore defined, $Z^1$ and $Z^2$ preferably each represent oxygen, and $Z^3$ represents an —SO$_2$—CH$_2$— linkage are prepared by the oxidation of corresponding compounds wherein $Z^3$ represents an —S—CH$_2$— linkage. For example, the oxidation can be carried out by means of sodium iodate in a medium such as aqueous methanol.

As another example, compounds of formula I wherein $R^1$, $R^2$, $R^3$, $Z^1$ and $Z^2$ are as hereinbefore defined, $Z^3$ represents a —CZCH$_2$— linkage, and Z represents sulfur are prepared from compounds of formula I wherein $R^1$, $R^2$, $R^3$, $Z^1$ and $Z^2$ are as hereinbefore defined, $Z^3$ represents a —CZCH$_2$— linkage, and Z represents oxygen, by reaction with phosphorus pentasulfide or 2,4-bis(4-methoxyphenyl)-1,3-dithia-2,4-diphosphetane-2,4-disulfide, preferably in a solvent such as pyridine or toluene, and preferably at a temperature from 0° C. to the reflux temperature.

As another example, compounds of formula I wherein $R^1$, $R^2$ Z, $Z^1$, $Z^2$ and $Z^3$ are as hereinbefore defined, Z, $Z^1$ and $Z^2$ preferably each represent oxygen, and $R^3$ is as hereinbefore defined and contains an alkylsulfonyl, arylsulfonyl, alkylsulfinyl or arylsulfinyl group, are prepared by the oxidation of the corresponding compounds of formula I wherein $R^1$, $R^2$, Z, $Z^1$, $Z^2$ and $Z^3$ are as hereinbefore defined and $R^3$ is as hereinbefore defined and contains an alkylthio or arylthio group, preferably by means of reaction with a peroxyacid, e.g. 3-chloroperbenzoic acid, preferably in an inert solvent, e.g. dichloromethane, preferably at or near room temperature. Alternatively, the oxidation is carried out by reaction with a peroxomonosulfate, e.g. potassium peroxomonosulfate, conveniently in a solvent such as methanol, buffered to about pH 5, at temperatures between about 0° C. and room temperature. This latter method is preferred for compounds containing an acid-labile group, such as those wherein the moiety $R^2O$— contains a carbon—carbon double bond between its beta- and gamma-carbon atoms, e.g. a cyclopent-2-enyloxy group.

As another example, compounds of formula I wherein $R^1$, $R^2$, Z, $Z^1$, $Z^2$ and $Z^3$ are as hereinbefore defined, and Z is preferably oxygen, and $R^3$ is as hereinbefore defined and contains a hydroxymethyl group are prepared by the reduction of the corresponding compounds of formula I wherein $R^1$, $R^2$, $Z^1$, $Z^2$ and $Z^3$ are as hereinbefore defined and $R^3$ is as hereinbefore defined and contains an aryloxycarbonyl or, preferably, alkoxycarbonyl group, preferably by means of reaction with an alkali metal borohydride, preferably in an inert solvent, e.g. tetrahydrofuran, preferably at or near room temperature.

As another example, compounds of formula I wherein $R^1$, $R^2$, Z, $Z^1$, $Z^2$ and $Z^3$ are as hereinbefore defined, Z preferably being an oxygen atom, and $R^3$ is as hereinbefore defined and contains a formyl group are prepared by the oxidation of the corresponding compounds of formula I wherein $R^1$, $R^2$, Z, $Z^1$, $Z^2$ and $Z^3$ are as hereinbefore defined and $R^3$ is as hereinbefore defined and contains a hydroxymethyl group, for example by reaction with oxalyl chloride and dimethyl sulfoxide, in a solvent such as dichloromethane, and preferably at a temperature lower than −65° C., or, preferably, by reaction with a complex of sulfur trioxide with an amine such as pyridine, preferably in the presence of an amine such as triethylamine, preferably at or near room temperature.

As another example, compounds of formula I wherein $R^1$, $R^2$, Z, $Z^1$, $Z^2$ and $Z^3$ are as hereinbefore defined, and Z is preferably oxygen, and $R^3$ is as hereinbefore defined and contains an amino group are prepared by the reduction of the corresponding compounds of formula I wherein $R^1$, $R^2$, Z, $Z^1$, $Z^2$ and $Z^3$ are as hereinbefore defined and $R^3$ is as hereinbefore defined and contains a nitro group, preferably by means of reaction with iron in acidic conditions, e.g. in acetic acid, preferably at or above room temperature, more especially at the reflux temperature. Alternatively the reduction are carried out by reaction with hydrazine hydrate in the presence of ferric chloride and activated carbon, conveniently in a solvent such as methanol, at temperatures between about 25° C. and 80° C. This latter method is preferred for compounds containing an acid-labile group, such as those wherein the moiety $R^2O$— contains a carbon—carbon double bond between its beta and gamma-carbon atoms, e.g. a cyclopent-2-enyloxy group.

As another example, compounds of formula I wherein $R^1$, $R^2$, Z, $Z^1$, $Z^2$ and $Z^3$ are as hereinbefore defined, and Z is preferably oxygen, and $R^3$ is as hereinbefore defined and contains an alkanoylamino or aroylamino group are prepared from compounds of formula I wherein $R^1$, $R^2$, Z, $Z^1$, $Z^2$ and $Z^3$ are as hereinbefore defined and $R^3$ is as hereinbefore defined and contains an amino group, preferably by means of reaction with the appropriate acid halide or acid anhydride in the presence of a tertiary base such as triethylamine, optionally in an inert solvent, and preferably at a temperature from 0° C. to the reflux temperature.

As another example, the compounds of formula I wherein $R^1$, $R^2$, Z, $Z^1$, $Z^2$ and $Z^3$ are as hereinbefore defined, Z, $Z^1$ and $Z^2$ preferably are oxygen, and $R^3$ represents a heteroaryl group containing one or more nitrogen ring atoms, can be converted to the corresponding N-oxides preferably by means of reaction with a mixture of hydrogen peroxide and an organic acid, e.g. acetic acid, preferably at or above room temperature at 60–90° C. Alternatively, the oxidation is carried out by reaction with hydrogen peroxide in the presence of sodium tungstate at temperatures between room temperature and about 60° C. This latter method is preferred for compounds containing an acid-labile group, such as those wherein the moiety $R^2O$— contains a carbon—carbon double bond between its beta-and gamma-carbon atoms, e.g. a cyclopent-2-enyloxy group.

For example, compounds of formula I wherein $R^1$ is as hereinbefore defined and is substituted on its alpha-carbon atom by fluorine and $Z^1$ is sulfur, and/or wherein $R^2$ is as hereinbefore defined and is substituted on its alpha-carbon atom by fluorine and $Z^2$ is sulfur, and $R^3$ and $Z^3$ as hereinbefore defined, are prepared by the reaction of xenon difluoride with corresponding compounds of formula I wherein said alpha-carbon atoms carry hydrogen atoms instead of said fluorine atoms. The reaction is conveniently carried out in a solvent, such as dichloromethane, in the presence of a molecular sieve, and in an inert atmosphere, at a low temperature, e.g. at or near 0° C.

As another example, compounds of formula I wherein $R^1$, $R^2$, Z, $Z^1$, $Z^2$ and $Z^3$ are as hereinbefore defined, and $R^3$ represents a heteroaryl group containing one or more nitrogen ring atoms but carrying no halogen substituents, are prepared by the reduction of the corresponding compounds of formula I wherein $R^3$ does carry one or more halogen, e.g. chlorine, substituents, for example by means of ammonium formate in the presence of a palladium catalyst.

Compounds of the present invention may contain asymmetric centers. These asymmetric centers may independently be in either the R or S configuration. It will be apparent to those skilled in the art that certain compounds of the invention may also exhibit geometrical isomerism. The present invention comprises the individual geometrical isomers and stereoisomers and mixtures thereof.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on TNF and PDE inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexyl-sulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-B-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on TNF and PDE inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

As will be self-evident to those skilled in the art, some of the compounds of this invention do not form stable salts. However, acid addition salts are most likely to be formed by compounds of this invention wherein $R^3$ represents a nitrogen-containing heteroaryl group and/or wherein $R^3$ contains an amino group as a substituent. Preferable acid addition salts of the compounds of the invention are those wherein $R^2$ is other than an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be apparent to those skilled in the art that certain compounds of formula I can exhibit isomerism, for example geometrical isomerism and optical isomerism. Geometrical isomers include the cis and trans forms of compounds of the invention having alkenyl or diazenyl moieties. All isomers within formula I, and their mixtures, are within the scope of the invention.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The starting materials and intermediates are prepared by the application or adaptation of known methods, for example methods as described in the Reference Examples or their obvious chemical equivalents.

For example, compounds of formula II, wherein $R^1$, $R^2$, $Z^1$ and $Z^2$ are as hereinbefore defined, are prepared from compounds of formula XXXV

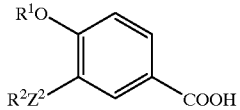

XXXV wherein $R^1$, $R^2$, $Z^1$ and $Z^2$ are as hereinbefore defined, by the application or adaptation of known methods for the preparation of acid halides from carboxylic acids. For example, when X in compound of formula II represents a chloro, the reaction can be carried out by means of thionyl chloride or, preferably, oxalyl chloride in the presence of triethylamine.

Compounds of formula XXXV, wherein $R^1$, $R^2$, $Z^1$ and $Z^2$ are as hereinbefore defined, are prepared by the oxidation of compounds of formula XVI above, wherein $R^1$, $R^2$, $Z^1$ and $Z^2$ are as hereinbefore defined, e.g. by means of reaction with potassium permanganate, or with a mixture of sulfamic acid and sodium chlorite in acetic acid, or with sodium chlorite in the presence of sodium dihydrogen phosphate.

Compounds of formula XVI, wherein $R^1$, $R^2$, $Z^1$ and $Z^2$ are as hereinbefore defined, are prepared from compounds of formula XXXVI

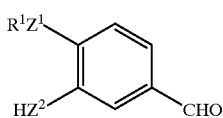

XXXVI wherein $R^1$, $Z^1$ and $Z^2$ are as hereinbefore defined, by reaction with compounds of the formula:

$R^2X$      V wherein $R^2$ and X are as hereinbefore defined, and X is preferably bromo, preferably in the presence of a base, for example an alkali metal hydride, e.g. sodium hydride, an alkali metal hydroxide or carbonate, e.g. sodium hydroxide or carbonate, or an amine, preferably a tertiary amine, e.g. triethylamine or pyridine, optionally in an inert solvent, for example dichloromethane, dimethylformamide, or an ether, e.g. diethyl ether or tetrahydrofuran, preferably at a temperature from 0° C. to the reflux temperature, or alternatively by reaction with compounds of the formula XXXVII $R^2OH$      XXXVII wherein $R^2$ is as hereinbefore defined, preferably in the presence of a compound such as diisopropyl azodicarboxylate.

Alternatively compounds of formula XXXV above, wherein $R^1$, $R^2$, $Z^1$ and $Z^2$ are as hereinbefore defined, are prepared by the hydrolysis of compounds of formula XXXVIII

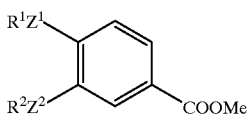

XXXVIII wherein $R^1$, $R^2$, $Z^1$ and $Z^2$ are as hereinbefore defined, e.g. by reaction with a base, such as an alkali metal carbonate or bicarbonate in the presence of water, followed by reaction with an aqueous acid such as dilute hydrochloric acid.

Compounds of formula XXXVIII above, wherein $R^1$, $R^2$, $Z^1$ and $Z^2$ are as hereinbefore defined, can be prepared from compounds of formula XXXIX

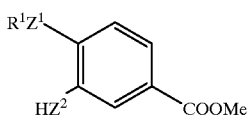

XXXIX where $R^1$ is as herein before defined, by reaction with compounds of the formula XXXVII, wherein $R^2$ is as hereinbefore defined, preferably in the presence of diisopropyl azodicarboxylate and triphenylphosphine.

Compounds of formula VI above, wherein $R^1$, $R^2$, $R^3$, $Z^1$ and $Z^2$ are as hereinbefore defined, are prepared by the reaction of compounds of formula XXXX

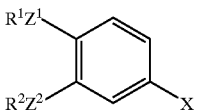

XXXX wherein $R^1$, $R^2$, $Z^1$ and $Z^2$ are as hereinbefore defined and X represents halo, e.g. bromo, with compounds of the formula XXXXI $R^3CH2CHO$      XXXXI wherein $R^3$ is as hereinbefore defined, in the presence of a base such as butyl lithium, preferably at a low temperature.

Alternatively, compounds of formula VI above, wherein $R^1$, $R^2$, $R^3$, $Z^1$ and $Z^2$ are as hereinbefore defined, are prepared by the reaction of compounds of formula XVI above,
wherein $R^1$, $R^2$, $Z^1$ and $Z^2$ are as hereinbefore defined, with compounds of the formula VIII above,
wherein $R^3$ is as hereinbefore defined, in the presence of a base such as lithium diisopropylamide (usually prepared in situ from butyl lithium and diisopropylamine), preferably at a low temperature.

For example, phenols and thiophenols of formula XIX above, wherein $R^1$, $R^3$, $Z^1$ and $Z^2$ are as hereinbefore defined, are prepared by the alkaline hydrolysis of their benzoyl esters, which themselves are prepared by reaction of the benzoyl esters of the corresponding sulfonyl chlorides having reacted with compounds of formula III above, wherein $R^3$ is as hereinbefore defined. The said sulfonyl chlorides are prepared by the action of thionyl chloride on the corresponding sulfonic acids, which themselves are prepared by insertion of the sulfo-group into the benzene ring by the action of chlorsulfonic acid.

Compounds of formula XXI, wherein $R^1$, $R^2$, $Z^1$ and $Z^2$ are as hereinbefore defined, are prepared by the reaction of bromine in carbon tetrachloride and ultraviolet radiation on the corresponding —$CHF_2$ compounds, which themselves are prepared by the action of sulfur tetrafluoride and hydrofluoric acid on compounds of formula XVI above, wherein $R^1$, $R^2$, $Z^1$ and $Z^2$ are as hereinbefore defined, in the presence of pyridine.

Compounds of formula XXIX above, wherein $R^1$, $R^2$, $Z^1$ and $Z^2$ are as hereinbefore defined, are prepared by the reaction of selenium dioxide on the corresponding acetophenones in the presence of pyridine.

Compounds of formula XXXIV above, wherein $R^1$, $R^2$, $R^3$, $Z^1$ and $Z^2$ are as hereinbefore defined, are prepared similarly by the reaction of the corresponding phenylacetaldehyde derivatives with compounds of formula XXXI above, wherein $R^3$ is as hereinbefore defined, in the presence of a base such as lithium diisopropylamide.

The present invention is further exemplified but not limited by the following illustrative examples which illustrate the preparation of the compounds according to the invention. The Reference Examples illustrate the preparation of the intermediates.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

EXAMPLE 1

Compounds A,B,C,D,E,F,G,H,I,J K,L,M,N,O,P,Q,R, S,T,U,V,W,X,Y and Z

A stirred solution of 2,6-difluoroaniline (1.52 g) and triethylamine (1.19 g) in dichloromethane (50 mL) at room temperature is treated dropwise with a solution of 3-cyclopentyloxy-4-methoxybenzoyl chloride (3.0 g), that is prepared as described hereinafter in Reference Example 3) in dichloro-methane (50 mL). The solution is stirred and heated at reflux for 4 hours, then it is cooled, washed with water and dried over magnesium sulfate. The solution is concentrated and the resulting residue is recrystallized from ethyl acetate, to give N-(2,6-difluorophenyl)-3-cyclopentyloxy-4-methoxybenzamide (1.9 g), m.p. 158–160° C. [NMR(CDCl3): 1.55–1.7(m,3H),1.8–2.05(m, 5H), 3.93(s,3H),4.85(m,1H),6.9(d,1H), 6.95–7.03(m,2H), 7.2–7.3(m,1H),7.35(bs,1H), 7.45(q,1H),7.53(d,1H); Elemental analysis: C,65.1; H,5.6; F,10.4; N,4.2%; Calculated: C,65.7; H,5.5; F,10.9; N,40%].

By proceeding in a similar manner, but replacing the 2,6-difluoroaniline by the appropriate quantities of the corresponding aniline derivatives. there are prepared:

N-(2-chloro-6-fluorophenyl)-3-cyclopentyloxy-4-methoxybenzamide. m.p. 140–142° C. [Elemental analysis: C,62.3; H,5.2; Cl,9.7; N,3.6%; Calculated: C,62.7; H,5.3; Cl,9.75; N,3.85%];

N-(2-trifluoromethylphenyl)-3-cyclopentyloxy-4-methoxybenzamide, m.p. 127–129° C. [Elemental analysis: C,63.4; H,5.5; F,13.3; N,3.3%; Calculated: C,63.3; H,5.3; F,15.0; N,3.7%];

N-(2,4,6-trichlorophenyl)-3-cyclopentyloxy-4-methoxybenzamide, m.p. 173° C. [Elemental analysis: C,55.2; H,4.4; Cl,26.4; N,3.1; Calculated: C,55.0; H,4.4; Cl,25.6; N,3.4%];

N-(2,6-dibromophenyl)-3-cyclopentyloxy-4-methoxybenzamide, m.p. 133° C. [Elemental analysis: C,48.5; H,4.0; Br,33.9; N,2.85%; Calculated: C,48.6; H,4.1; Br,34.1; N,3.0%];

N-(2-chloro-6-methylphenyl)-3-cyclopentyloxy-4-metboxybenzamide, m.p. 138–140° C. [Elemental analysis: C,66.3; H,6.2; Cl,10.3; N,3.8%; Calculated: C,66.75; H,6.2; Cl,9.85; N,3.9%];

N-(2,6-dichlorophenyl)-3-cyclopentyloxy-4-methoxybenzamide, m.p. 138–140° C. [Elemental analysis: C,59.8; H,5.1; Cl,19.1; N. 3.3%; Calculated: C,60.0; H,5.0; Cl,18.65; N,3.7 %];

N-(2-fluoropbenyl)-3-cyclopentyloxy-4-methoxybenzamide, m. p. 137 ° C. [Elemental analysis: C,69.3; H,6.2; F,5 .7; N,4.0%; Calculated: C,69.3; H,6.1; F,5.8; N,4.25%];

N-phenyl-3-cyclopentyloxy-4-methoxybenzamide, m. p. 169–173 ° C. [Elemental analysis: C, 73.2; H,6.7; N,4.2%; Calculated: C,73.3; H,6.8; N,4.5%];

N-(2-methoxyphenyl)-3-cyclopentyloxy-4-methoxybenzamide, m.p. 132–134° C. [Elemental analysis: C,70.1; H,6.8; N,4.0%; Calculated: C,70.4; H,6.8; N,4.1%];

N-(2-chlorophenyl)-3-cyclopentyloxy-4-methoxybenzamide, m.p. 122–124° C. [Elemental analysis: C,65.8; H,5.8; Cl,10.5; N,3.9%; Calculated: C,66.0; H,5.8; Cl,10.25; N,4.05%];

N-(3-chlorophenyl)-3-cyclopentyloxy-4-methoxybenzamide, m.p. 110–1 112° C. [Elemental analysis: C,65.9; H,6.5; Cl,9.8; N,3.7%; Calculated: C,66.0; H,5.8; Cl,10.25; N,4.05%];

N-(4-methoxyphenyl)-3-cyclopentyloxy-4-methoxybenzamide, m.p. 182–184° C. [Elemental analysis: C,68.7; H,6.6; N.3.8%;Calculated for $C_{20}H_{23}NO_4$:1/2$H_2O$: C,68.55; H,6.9; N,4.0%];

N-(2,6-dimethylphenyl)-3-cyclopentyloxy-4-methoxybenzamide, m.p. 130–131 ° C. [Elemental analysis: C,74.2; H,7.4; N,4.1%; Calculated: C,74.3; H,7.4; N,4.13%];

N-(2-methylthiophenyl)-3-cyclopentyloxy-4-methoxybenzamide, m.p. 128–130° C. [Elemental analysis: C,67.6; H,6.5; N,3.9; S,8.9%; Calculated: C,67.2; H,6.5; N,3.9; S,9.0%;

N-(2-bromophenyl)-3-cyclopentyloxy-4-methoxybenzamide, m.p. 126–128° C. [Elemental analysis: C,58.2; H,5.1; Br,20.4; N,3.5%; Calculated: C,58.5; H,5.2; Br,20.5; N,3.6%];

N-(2-methoxycarbonylphenyl)-3-cyclopentyloxy-4-methoxybenzamide, m.p. 105–107° C. [Elemental analysis: 68.4; H,6.35; N,3.7%; Calculated: 68.3;6.3; N,3.8%];

N-(2-aminosulfonylphenyl)-3-cyclopentyloxy-4-methoxybenzamide, m.p. 248° C. [Elemental analysis: C,58.0; H,5.5; N,6.9%; Calculated: C,58.45; H,5.7; N,7.2%];

N-(2-benzoylphenyl)-3-cyclopentyloxy-4-methoxybenzamide, m.p. 106–107° C. [Elemental analysis: C,75.5; H,6.3; N,3.3%; Calculated: C,75.2; H,6.1; N,3.4%];

N-(2-cyanophenyl)-3-cyclopentyloxy-4-methoxybenzamide, m.p. 170–172° C. [Elemental analysis: C,71.0; H,6.0; N,8.1%; Calculated: C,75.2; H,6.1; N,3.4%];

N-(2,5-dichlorophenyl)-3-cyclopentyloxy-4-methoxybenzamide, m.p. 117–11 9° C. [Elemental analysis: C,59.7; H,5.0; Cl,18.5; N,3.7%; Calculated: C,60.0; H,5.0; Cl,18.65; N,3.7%];

N-(3-methylphenyl)-3-cyclopentyloxy-4-methoxybenzamide, m.p. 147–149° C. [Elemental analysis: C,73.8; H,7.1; N,4.2%; Calculated: C,73.8; H,7.1; N,4.3%];

N-(2-nitrophenyl)-3-cyclopentyloxy-4-methoxybenzamide, m.p. 130–132° C. [Elemental analysis: C,64.0; H,5.7; N,7.4%; Calculated: C,64.0; H,5.7; N,7.9%];

N-(2-dimethylaminophenyl)-3-cyclopentyloxy-4-methoxybenzamide, in the form of a brown oil [Elemental analysis: C,71.5; H,7.4; N,7.4%; Calculated: C,71.2: H,7.4; N,7.9%];

N-(2-acetylphenyl)-3-cyclopentyloxy-4-methoxybenzamide, m.p. 126–127° C. [Elemental analysis: C,71.0; H,6.6; N,3.9%; Calculated: C,71.4; H,6.6; N,4.0%]; and N-(2-hydroxyphenyl)-3-cyclopentyloxy-4-methoxybenzamide, m.p. 169–171 ° C. [Elemental analysis: C,69.5; H,6.5; N,3.9%; Calculated: C,69.7; H,6.5; N,4.3%].

EXAMPLE 2

Compound AA

A stirred solution of N-(2-methylthiophenyl)-3-cyclopentyloxy-4-methoxybenzamide (1.80 g; that is prepared as described hereinbefore in Example 1) is treated with a solution of 3-chloroperbenzoic acid (3.60 g; 85% pure) in dichloromethane (72 mL), dropwise, and then it is stirred at room temperature for 5 hours. The reaction mixture is washed with saturated aqueous sodium bicarbonate solution and then with water, and then it is dried over magnesium sulfate. The mixture is concentrated to give N-(2-methylsulfonylphenyl)-3-cyclopentyloxy-4-methoxybenzamide, (1.12 g), in the form of a white solid.

m.p. 119–121° C. [NMR(CDCl$_3$): 1.52–2.16 (m,8H), 3.1 (s,3H),3.94(s,3H),4.9(m,$_1$H), 6.96(d,1H),7.46 (m,1H),7.6 (m,2H),7.7(t,1H), 7.95(d,1H),8.68(d,1H); Elemental analysis: C,61.6; H,6.0; N,3.5; S,8.5%; Calculated: C,61.7; H,5.95; N,3.6; S,8.5%].

EXAMPLE 3

Compounds AB AC and AD

By proceeding in a manner similar to that described hereinbefore in Example 1, but using the appropriate quantities of the corresponding acid chlorides, which are prepared as described hereinafter in Reference Example 3, there are prepared:

N-(2,6-difluorophenyl)-3-cyclohexyloxy-4-methoxybenzamide, m.p. 60° C. [Elemental analysis: C,66.1; H,6.3; N,3.3%; Calculated: C,66.5; H,5.9; N,3.9%];

N-(2,6-difluorophenyl)-3-butoxy-4-methoxybenzamide, m.p. 150–152° C. [Elemental analysis: C,64.6; H,5.8; N,4.2; Calculated: C,64.5; H,5.7; N,4.2%]; and N-(2,6-difluorophenyl)-3-propoxy-4-methoxybenzamide, m.p. 170–1740C. [Elemental analysis: C,63.4; H,5.4; N,4.4%; Calculated: C,63.5; H,5.3; N,4.4%].

EXAMPLE 4

Compound AE

3-Cyclopentyloxy-4-methoxybenzoyl chloride (13.3 g) and 2-chloroaniline (6.6 g) are dissolved in pyridine (50 mL) and the solution is allowed to stand at room temperature for 1 hour. Phosphorus pentasulfide (13 g) is added and the stirred mixture is heated at 110° C. for 1.5 hours. After cooling to room temperature the mixture is poured into an ice-cold solution of concentrated hydrochloric acid (100 mL) in water (400 mL). The mixture is stirred for 1 hour and the yellow solid is collected, washed with water and subjected to flash chromatography on silica gel, eluting with a mixture of cyclohexane and ethyl acetate (3:1 v/v), to give N-(2-chlorophenyl)-3-cyclopentyloxy-4-methoxy (thiobenzamide) (5.4 g), m.p. 129–131° C. [Elemental analysis: C,62.6; H,5.5; N,3.9; S,8.9%; Calculated: C,63.1; H,5.6; N,3.9; S,8.9%].

EXAMPLE 5

Compounds AF, AG, AH, AI, AJ, AK, AL, AM and AN

A stirred solution of 4-chloropyrid-3-ylamine (1.94 g) and 3-cyclopentyloxy-4-methoxybenzoyl chloride (3.85 g) in pyridine (50 mL) is heated at 80° C. for 7 hours and then it is allowed to stand overnight. The reaction mixture is evaporated, to give a brown oil, which is subjected to mplc on silica gel, using diethyl ether as eluent, to give N-(4-chloropyrid-3-yl)-3-cyclopentyloxy-4-methoxybenzamide (3.1 g), m.p. 130–132° C.

By proceeding in a similar manner, but using the appropriate quantities of the appropriate amines instead of the 4-chloropyrid-3-ylamine used as a starting material, there are prepared:

N-pyrid-2-yl-3-cyclopentyloxy-4-methoxybenzamide, m.p. 92–94° C.;

N-pyrazin-2-yl-3-cyclopentyloxy-4-methoxybenzamide, m.p. 80–82° C.;

N-pyrimidin-2-yl-3-cyclopentyloxy-4-methoxybenzamide, m.p. 108–110° C.;

N-(3-methylpyrid-2-yl)-3-cyclopentyloxy-4-methoxybenzamide, m.p. 55° C.;

N-pyrid-3-yl-3-cyclopentyloxy-4-methoxybenzamide, m.p. 170–172° C.;

N-(3-chloropyrid-2-yl)-3-cyclopentyloxy-4-methoxybenzamide., m.p. 138–140° C.;

N-(3-chloropyrid-4-yl)-3-cyclopentyloxy-4-methoxybenzamide, m.p. 124–126° C.; and N-pyrid-4-yl-3-cyclopentyloxy-4-methoxybenzamide, m.p. 163–165° C.

EXAMPLE 6

Compound AO

4-Amino-3,5-dichloropyridine (4.0 g) and 3-cyclopentyloxy-4-methoxybenzoyl chloride (6.26 g) are intimately ground together in a mortar with a pestle, and transferred to a round-bottomed flask. The mixture is melted, using a hot air gun external to the flask, stirring with a magnetic stirrer. After 10 minutes, heating is ceased and the melt is allowed to cool. The resulting material is triturated with dichloromethane and the residual solid is filtered off. The filtrate is concentrated to give a fawn solid, which is subjected to flash chromatography on silica gel, eluting with diethyl ether, to give N-(3,5-dichloro-pyrid-4-yl)-3-cyclopentyloxy-4-methoxybenzamide (1.87 g), m.p. 155–157° C. [Elemental analysis: C,56.3; H,4.7; N,7.2; Cl,18.4%; calculated: C,56.7; H,4.76; N,7.35; Cl,18.6%; IR spectrum: 1661 cm$^{-1}$, 3244 cm$^{-1}$].

Alternatively, a suspension of 3-cyclopentyloxy-4-methoxybenzamide (2.58 g; that is prepared as described in Reference Example 73) in dry toluene (40 mL) is heated at reflux and treated with potassium t-butoxide (1.4 g), followed by 3,4,5-trichloro-pyridine (1.82 g). The mixture is then heated at reflux for 3 hours and 45 minutes, and is then treated with a further quantity of potassium t-butoxide (1.4 g) and heated at reflux for a further period of 7 hours. The mixture is allowed to cool and is then filtered. The filtrate is evaporated and the resulting residue is extracted with aqueous sodium hydroxide solution (2 M). The alkaline solution is then acidified by treatment with acetic acid, and the solid which separates is collected by filtration, washed with water and dried, to give N-(3,5-dichloropyrid-4-yl)-3-cyclopentyloxy-4-methoxy-benzamide (2.09 g) in the form of a buff solid, m.p. 153–155° C.

EXAMPLE 7

Compound AP

By proceeding in a manner similar to that described hereinbefore in Example 1, but replacing the 2,6-difluoroaniline that is used as a starting material by the appropriate quantity of 4-amino-3,5-dimethylisoxazole, there is prepared N-(3,5-dimethylisoxazol-4-yl)-3-cyclopentyloxy-4-methoxy-benzamide, m.p. 150–152° C. [Elemental analysis: C,65.6; H,6.8; N,8.5%; calculated: C,65.4; 11,6.7; N,8.5% 11].

EXAMPLE 8

Compounds AO, AY, BC, BG, BL, BQ, BS, BX, AX, AZ, AW, BV, BW, DF, DG, DH, DI, DJ, DK, DL, DM and DN A suspension of sodium hydride (60% dispersion in oil; 2.2 g) in dry tetrahydrofuran (25 mL) at 15–20° C. is treated portionwise with a solution of 4-amino-3,5-dichloropyridine (4.5 g; that is prepared as described in Reference Example 5) in dry tetrahydrofuran (40 mL), with cooling. The mixture is stirred for a further 30 minutes, and then it is cooled to 10° C. and treated with a solution of 3-cyclopentyloxy-4-methoxybenzoyl chloride (6.4 g) in dry tetrahydrofuran (40 mL), dropwise, during 45 minutes at 10° C. The mixture is stirred at 10° C. for 30 minutes and is then treated with dilute hydrochloric acid (50 mL; 1 N), followed by dichloromethane (75 mL). The layers are separated and the aqueous layer is washed with a further quantity of dichloromethane (25 mL). The combined organic layers are washed with water (50 mL), with saturated aqueous sodium bicarbonate solution (100 mL), and with water (50 mL), dried over magnesium sulfate and evaporated to dryness. The resulting residue is recrystallized from isopropanol, to give N-(3,5-dichloropyrid-4-yl)-3-cyclopentyloxy-4-methoxybenzamide (7.0 g).

By proceeding in a similar manner, but using the appropriate quantities of the corresponding benzoyl halides and amines as starting materials, and optionally using dimethylformamide instead of tetrahydrofuran, there are prepared:

N-(3,5-dibromopyrid-4-yl)-3-cyclopentyloxy-4-methoxybenzamide, m.p. 160–162° C. [Elemental analysis: C,46.4; H,3.9; N,6.1%; calculated: C,46.0; H,3.9; N,6.0%];

N-(3,5-dimethylpyrid-4-yl)-3-cyclopentyloxy-4-methoxybenzamide, m.p. 77–80° C. [Elemental analysis: C,67.2; H,6.9; N,7.8%; calculated: C,67.0; H,7.3; N,7.8%];

N-(2,6-dichloro-4-cyanophenyl)-3-cyclopentyloxy-4-methoxybenzamide, m.p. 170–172° C. [Elemental analysis: C,59.1; H,4.5; N,7.0; Cl,17.5%; calculated: C,59.3; H,4.5; N,6.9; Cl,17.5%];

N-(2,6-dichloro-4-methoxycarbonylphenyl)-3-cyclopentyloxy-4-methoxybenzamide, m.p. 158–160° C. [Elemental analysis: C,57.4; H,4.9; N,3.2; Cl,16.4%; calculated: C,57.5; H,4.8; N,3.2; Cl,16.2%];

N-(2,3,5-trifluoropyrid-4-yl)-3-cyclopentyloxy-4-methoxybenzamide, m.p. 144–146° C. [Elemental analysis: C,59.3; H,4.9; N,7.5%; calculated: C,59.0; H,4.7; N,7.65%];

N-(2,6-dichloro-4-ethoxycarbonylphenyl)-3-cyclopentyloxy-4-methoxybenzamide, m.p. 164–166° C.; N-(2,6-dichloro-4-nitrophenyl)-3-cyclopentyloxy-4-methoxybenzamide, m.p. 154–156° C.;

N-(3,5-dichloropyrid-4-yl)-3-cyclohexyloxy-4-methoxybenzamide, m.p. 170° C. [Elemental analysis: C,57.8; H,5.1; N,7.0; Cl,17.8%; calculated: C,57.7; H,5.1; N,7.1; Cl,17.9%];

N-(3,5-dichloropyrid-4-yl)-3-butoxy-4-methoxybenzamide, m.p. 165–167° C. [Elemental analysis: C,55.1; H,4.8; N,7.6; Cl,19.2%; calculated: C,55.3; H,4.9; N,7.6; Cl,19.2%];

N-(3,5-dichloropyrid-4-yl)-3-(exo-8,9,10-trinorbornyl-2-oxy)-4-methoxybenzamide, m.p. 149–150° C. [Elemental analysis: C,58.8; H,4.9; N,6.7%; calculated: C,59.0; H,5.0; N,6.9%];

(R)-N-(3,5-dichloropyrid-4-yl)-3-(exo-8,9,10-trinorbornyl-2-oxy)-4-methoxybenzamide, m.p. 155–156° C. [Elemental analysis: C,58.8; H,5.0; N,6.8%];

(S)-N-(3,5-dichloropyrid-4-yl)-3-(exo-8,9,10-trinorbornyl-2-oxy)-4-methoxybenzamide, m.p. 156–157° C.;

3-cyclopentyloxy-N-(3,5-difluoropyrid-4-yl)-4-methoxybenzamide, m.p. 160–161° C. [Elemental analysis: C,61.7; H,5.2; N,8.0%; calculated: C,62.1; H,5.2; N,8.0%];

(R)-N-(2,6-dichlorophenyl)-3-(exo-8,9,10-trinorbornl-2-oxy)-4-methoxy-benzamide, m.p. 144–145° C. [Elemental analysis: C,61.7; H,5.1; N,3.3%; calculated: C,62.1; H,5.2; N,3.45%];

(S)-N-(2,6-dichlorophenyl)-3-(exo-8,9,10-trinorbornyl-2-oxy)-4-methoxy-benzamide, m.p. 143–144° C. [Elemental analysis: C,62.1; H,5.2; N,3.1%; calculated: C,62.1; H,5.2; N,3.45%];

3-cyclopentylmethoxy-N-(3,5-dichloropyrid-4-yl)-4-methoxybenzamide, m.p. 192–200° C. [Elemental analysis: C,58.1; H,5.1; N,7.1%; calculated: C,57.7; H,5.1; N,7.1%];

3-cyclopropylmethoxy-N-(3,5-dichloropyrid-4-yl)-4-methoxybenzamide, m.p. 226–230° C. [Elemental analysis: C,55.3; H,4.4; N,7.4%; calculated: C,55.6; H,4.4; N,7.6%];

N-(3-bromo-5-chloropyrid-4-yl)-3-cyclopentyloxy-4-methoxybenzamide, m.p. 132–134° C. [Elemental analysis: C,50.8; H,4.2; N,6.5%; calculated: C,50.8; H,4.3; N,6.6%];

N-(3,5-dichloropyrid-4-yl)-3-isopropoxy-4-methoxybenzamide. m.p. 175–176° C. [Elemental analysis: C,54.3; H,4.6; N,8.0%; calculated: C,54.1; H,4.5; N,7.9%];

3-tert-butoxy-N-(3,5-dichloropyrid-4-yl)-4-methoxybenzamide, m.p. 148–150° C. [Elemental analysis: C,55.3; H,4.95; N7.5%; calculated: C,55.3; H,4.9; N,7.6%]; and N-(3,5-dichloropyrid-4-yl)-4-methoxy-3-(pent-3-yloxy)benzamide m.p. 133–134° C. [Elemental analysis: C,56.5; H,5.25; N,7.3; Cl,18.4%; calculated: C,56.4; H,5.26; N,7.3; Cl,18.5%).

EXAMPLE 9

Compound AV

A stirred suspension of N-(3,5-dichloropyrid-4yl)-3-cyclopentyloxy-4-methoxybenzamide (2.0 g; that is prepared as described in Example 6) in glacial acetic acid (8 mL) is treated with an aqueous solution of hydrogen peroxide (6 mL; 27.5%). The mixture is stirred for 3 hours at 70–80° C. and then it is treated with a further portion of hydrogen peroxide solution (4 mL), and the solution is stirred for a further 12 hours. The solution is then cooled, basified by treatment with concentrated aqueous sodium hydroxide solution, and extracted with dichloromethane (2×30 mL). The organic extract is washed with brine (30 mL), dried over magnesium sulfate and evaporated. The resulting residue is recrystallized from ethyl acetate, to give 3,5-dichloro-4-(3-cyclopentyloxy-4-methoxybenzamido)pyridine-N-oxide (0.73 g), m.p. 118–120° C. [Elemental analysis: C,53.0; H,4.4; N,6.8%; calculated for $C_{18}H_{18}O_4N_2Cl_2 \cdot 0.5H_2O$: C,53.2; H, 4.7; N, 6.9%].

EXAMPLE 10

Compound BE

A stirred solution of N-(3,5-dichloropyrid-4yl)-3-cyclopentyloxy-4-methoxybenzamide (2.0 g; that is prepared as described in Example 6) in toluene (50 mL) is treated with 2,4-bis(4-methoxyphenyl)-1,3-dithia-2,4- diphosphetane-2,4-disulfide (3.0 g), and the mixture is heated at 100° C. for 2 hours. After cooling to room temperature and filtration, the filtrate is concentrated in vacuo, to give a yellow oil. This oil is subjected to flash chromatography on silica gel, using a mixture of pentane and ethyl acetate (8:2 v/v) as eluent, to give N-(3,5-dichloropyrid-4-yl)3-cyclopentyloxy-4-methoxy (thiobenzamide) (0.64 g) m.p. 118–119° C. [Elemental analysis: C,54.1; H,4.6; Cl,17.4; N,6.8%; calculated: C,54.4; H,4.6; Cl,17.85; N,7.05%].

EXAMPLE 11

Compound BI

A solution of N-(2,6-dichloro-4-nitrophenyl)-3-cyclopentyloxy-4-methoxybenzamide (1.5 g; that is prepared as described in Example 8) in glacial acetic acid (22 mL) is treated with iron pin dust (1.3 g) and the mixture is heated with stirring at 90° C. for 1 hour. The reaction mixture is cooled, basified to pH 8 by treatment with saturated aqueous sodium carbonate solution, and extracted with ethyl acetate (2×150 mL). The combined organic extract is dried over magnesium sulfate and concentrated in vacuo, to give a white solid. This solid is subjected to flash chromatography, eluting with a mixture of ethyl acetate and pentane (1:1 v/v), to give N-(2,6-dichloro-4-aminophenyl)-3-cyclopentyloxy-4-methoxybenzamide (0.8 g), m.p. 170–172° C. [Elemental analysis: C,54.8; H,5.04; N,6.5; Cl,17.4%; calculated: C,57.7; H,5.1; N,7.1; Cl,17.9%].

EXAMPLE 12

Compound BM

Acetic anhydride (10 mL) is treated with N-(2,6-dichloro-4-aminophenyl)-3-cyclopentyloxy-4-methoxybenzamide (0.8 g; that is prepared as described in Example 11), and the reaction mixture is stirred for 2 hours and left to stand overnight. It is then poured into water (100 mL), and extracted with ethyl acetate (100 mL) and then with dichloromethane (100 mL). The organic extracts are combined, dried over magnesium sulfate, and evaporated, to give N-(4-acetylamino-2,6-dichlorophenyl)-3-cyclopentyloxy-4-methoxybenzamide (0.4 g), m.p. 250–252° C. [Elemental analysis: C,57.6; H,5.05; N,6.3; Cl,16.1%; calculated: C,57.5; H,5.1; N,6.4; Cl,16.2%].

EXAMPLE 13

Compounds BN and BU

A stirred solution of N-(3,5-dichloropyrid-4-yl)-3-hydroxy-4-methoxybenzamide (2.0 g; that is prepared as described in Reference Example 12) in dimethylformamide (20 mL) at room temperature under nitrogen is treated portionwise with a suspension of sodium hydride (60% dispersion in oil; 0.26 g), and then it is stirred for a further hour at room temperature. It is then treated dropwise with 1-bromononane (1.2 mL) and stirred at 60° C. for 5 hours. The solution is then cooled to room temperature, diluted with water (60 mL), and extracted with ethyl acetate (2×100 mL). The combined organic extracts are dried over magnesium sulfate and evaporated, to give a white solid, which is subjected to flash chromatography on silica gel, eluting with t-butyl methyl ether, to give N-(3,S-dichloropyrid-4-yl)-3-nonyloxy-4-methoxybenzamide (0.56 g), m.p. 151–153° C. [Elemental analysis: C,60.3; H,6.45; N,6.3%; calculated: C,60.1; H,6.4; N,6.4%].

By proceeding in a similar manner, but using the appropriate quantity of 1-bromododecane, there is prepared N-(3,5-dichloropyrid-4-yl)-3-dodecyloxy-4-methoxybenzamide, m.p. 143–145° C.

EXAMPLE 14

Compound BO

A solution of N-(2,6-dichloro-4-hydroxymethylphenyl)-3-cyclopentyloxy-4-methoxybenzamide (4.4 g) in dichloromethane (30 mL) is treated with activated manganese dioxide (6.2 g), and the mixture is stirred at reflux for 24 hours. The mixture is filtered, the filtrate is evaporated, and the resulting residue is subjected to flash chromatography on silica gel, eluting with ethyl acetate, to give N-(2,6-dichloro-4-formylphenyl)-3-cyclopentyloxy-4-methoxybenzamide (2.4 g), m.p. 96–98° C. [Elemental analysis: C,59.0; H,5.1; N,3.1%; calculated: C,58.8; H,4.7; N,3.4%].

EXAMPLE 15

Compound BT

A stirred solution of N-(2,6-dichloro-4-ethoxycarbonylphenyl)-3-cyclopentyloxy-4-methoxybenzamide (6.1 g; that is prepared as described in Example 8) in dry tetrahydrofuran (80 mL) at room temperature under argon is treated dropwise with a solution of lithium borohydride in tetrahydrofuran (115 mL; 2 M). The mixture is stirred overnight and then it is treated portionwise with saturated brine (200 mL) and stirred for 30 minutes. The organic layer is then washed with water, dried over magnesium sulfate and evaporated. The resulting residue is subjected to flash chromatography on silica gel, to give N-(2,6-dichloro-4-hydroxymethylphenyl)-3-cyclopentyloxy-4-methoxybenzamide (4.4 g), m.p. 174–176° C. [Elemental analysis: C,57.1; H,5.4; N,2.9%; calculated $C_{20}H_{21}O_4NCl_2 \cdot 0.5H_2O$: C,57.3; H,5.3; N,3.3%].

EXAMPLE 16

Compound BR

A solution of N-(3,5-dichloropyrid-4-yl)-3-cyclopentyloxy-4-methoxybenzamide (3.8 g; that is prepared as described in Example 6) in dry tetrahydrofuran (25 mL) is treated with a suspension of sodium hydride (60% dispersion in oil; 0.40 g), and the mixture is stirred until effervescence has ceased and a solution has formed. This solution is evaporated in vacuo and the resulting residue is triturated with t-butyl methyl ether (20 mL). The resulting off-white solid is filtered off, quickly washed with t-butyl methyl ether (2×20 mL) and dried, to give the sodium salt of N-(3,5-dichloropyrid-4-yl)-3-cyclopentyloxy-4-methoxy-benzamide (3.5 g), m.p. 265–270° C. (with decomposition) [NMR(DMSO-$D_6$): 1.52–1.93(m,8H),4.77 (s,3H),4.75–4.80 (m,1H),6.98(d,1H),7.5 8(dd,1H), 7.60(s, 1H),8.20(s,2H); IR spectrum: strong peak at 1508 $cm^{-1}$, with no peaks at or near 1661 $cm^{-1}$ nor 3244 $cm^{-1}$, which would have been characteristics of the starting material].

EXAMPLE 17

Compounds AU BF and BP

By proceeding in a manner similar to that described in Example 5, but replacing the 4-chloropyrid-3-ylamine that is used as a starting material by the appropriate quantities of the corresponding aniline derivatives, there are prepared:

N-(2,4,6-trifluorophenyl)-3-cyclopentyloxy-4-methoxybenzamide, m.p. 160–162° C. [Elemental analysis: C,62.5; H,5.0; N,3.6%; calculated: C,62.5; H,5.0; N,3.8%]; and N-(2,6-dichloro-4-methoxyphenyl)-3-cyclopentyloxy-4-methoxybenzamide, m.p. 126–128° C. [Elemental analysis: C,57.9; H,4.9; N,3.2%; calculated: C,58.5; H,5.2; N,3.4%].

By again proceeding in a similar manner, but replacing the 4-chloropyrid-3-ylamine and the 3-cyclopentyloxy-4-methoxybenzoyl chloride by the appropriate quantities of 2,6-dichloroaniline and 3-(exo-8,9,10-trinorbornyl-2-oxy)-4-methoxybenzoyl chloride (that is prepared as described in Reference Example 14), there is prepared N-(2,6-dichlorophenyl)-3-(exo-8,9,10-trinorbornyl-2-oxy)-4-methoxybenzamide, m.p. 106–107° C. [Elemental analysis: C,61.8; H,5.2; N,3.2%; calculated: C,62.1; H,5.2; N,3.45%].

EXAMPLE 18

Compounds AQ, AS, AT, BD, BH, BJ and BK

By proceeding in a manner similar to that described in Example 6, but replacing the 4-amino-3,5-dichloropyridine that is used as a starting material by the appropriate quantities of the corresponding amines, there are prepared:

N-(4,6-dichloropyrimid-5-yl)-3-cyclopentyloxy-4-methoxybenzamide, m.p. 191–193° C. [Elemental analysis: C,53.1; H,4.4; Cl,18.6; N,10.9%; calculated: C,53.1; H,4.5; Cl,18.6; N,10.8%];

N-(2,3,5,6-tetrafluoropyrid-4-yl)-3-cyclopentyloxy-4-methoxybenzamide, m.p. 178–180° C. [Elemental analysis: C,56.0; H,4.1; N,7.2%; calculated: C,56.25; H,4.2; N,7.3%];

N-(3,5-dichloro-2,6-difluoropyrid-4-yl)-3-cyclopentyloxy-4-methoxybenzamide m.p. 188–190° C. [Elemental analysis: C,51.5; H,3.8; N,6.8; Cl,17.0%; calculated: C,51.8; H,3.9; N,6.7; Cl,17.0%];

N-(5-cyano-3-methylisothiazol-4-yl)-3-cyclopentyloxy-4-methoxybenzamide, m.p. 163–164° C. [Elemental analysis: C,60.0; H,5.3; N,11.7%; calculated: C,60.5; H,5.85; N,11.8%];

N-(2,6-dichloro-4-carbamoylphenyl)-3-cyclopentyloxy-4-methoxybenzamide, m.p. 245–247° [Elemental analysis: C,54.0; H,4.5; N,6.4%; calculated: C,54.4; H,5.0; N,6.35%]; and N-(3-chloro-2,5,6-trifluoropyrid-4-yl)-3-cyclopentyloxy-4-methoxybenzamide, m.p. 188–190° C. [Elemental analysis: C,53.7; H,3.95; N,6.81; Cl,8.9%; calculated: C,53.94; H,4.0; N,7.0; Cl,8.85%].

By again proceeding in a similar manner, but replacing the 4-amino-3,5-dichloropyridine and the 3-cyclopentyloxy-4-methoxybenzoyl chloride by the appropriate quantities of 4-amino-3,5-dibromopyridine and 3-butoxy-4-methoxybenzoyl chloride (that is prepared as described in Reference Example 3), there is prepared N-(3,5-dibromopyrid-4-yl)-3-butoxy-4-methoxybenzamide, m.p. 160–162° C. [Elemental analysis: C,44.6; H,3.9; N,6.1%; calculated: C,44.6; H,4.0; N,6.1%].

EXAMPLE 19

Compounds AR, BA and BB

By proceeding in a manner similar to that described in Example 1, but replacing the 2,6-difluoroaniline that is used as starting material by the appropriate quantities of the corresponding amines, there are prepared: N-(4-nitrophenyl)-3-cyclopentyloxy-4-methoxybenzamide, m.p. 178–180° C. [Elemental analysis: C,64.1; H,5.7; N,7.5%; calculated: C,64.0; H,5.7; N,7.9%];

N-(3-methyl-5-bromoisothiazol-4-yl)-3-cyclopentyloxy-4-methoxybenzamide, m.p. 160–162° C. [Elemental analysis: C,50.0; H,4.7; N,6.8%; calculated: C,49.6; H,4.7; N,6.8%]; and N-(3,5-dimethylisothiazol-4-yl)-(3-cyclopentyloxy-4-methoxybenzamide, m.p. 140–141° C. [Elemental analysis: C,62.4; H,6.35; N,8.0%; calculated: C,62.4; H,6.4; N,8.1%].

EXAMPLE 20

Compound BY

A solution of 4-amino-3,5-dichloropyridine (0.46 g) in dry dimethylformamide (20 mL) is treated with sodium hydride (0.23 g of a 60% dispersion in mineral oil; 2.8 mmol) and the mixture is stirred for 20 minutes. It is then treated with a solution of 3-cyclopentyloxy-4-(methylthio) benzoyl chloride (0.76 g; that is prepared as described in Reference Example 20 in dimethylformamide (10 mL) and stirred at 60° C. for 2 hours. The solution is then concentrated and the resulting residue is partitioned between water (30 mL) and ethyl acetate (50 mL). The aqueous layer is extracted with ethyl acetate (50 mL) and the combined organic layers are dried, concentrated, and subjected to flash chromatography on silica gel, eluting with a mixture of diethyl ether and pentane (1:1 v/v), to give N-(3,5-dichloropyrid-4-yl)-3-cyclopentyloxy-4-(methylthio) benzamide (0.7 g) in the form of a white crystalline solid, m.p. 157–159° C. [NMR (CDCl$_3$):8.57 (s,2H), 7.69 (bs,1H), 7.47 (dd,1H,J=8 Hz,J=2 Hz), 7.43 (d,1H,J=2 Hz), 7.17 (d,1H,J=8 Hz), 4.95 (m,1H), 2.46 (s,3H), 1.98–1.6(m,8H); Elemental analysis: C,54.0; H,4.5; N,7.0; Cl,17.8%; calculated: C,54.4; H,4.6; N,7.05; Cl,17.85%].

EXAMPLE 21

Compound BZ

As in Example 20 but using 4-amino-3,5-difluoropyridine instead of 4-amino-3,5-dichloropyridine, N-(3,5-difluoropyrid-4-yl)-3-cyclopentyloxy-4-(methylthio) benzamide is synthesized; m.p. 174–5° C. [Elemental analysis: C,59.4; H,5.1; N,7.6; S,8.3%; calculated: C,59.3; H,5.0; N,7.7; S,8.3%].

EXAMPLE 22

Compounds CA, CB and CC

A solution of 4-amino-3,5-dichloropyridine (1.6 g) in dry tetrahydrofuran (20 mL) at 0° C. under nitrogen is treated with sodium hydride (1 g of a 60% dispersion in mineral oil) and then stirred for a further 30 minutes at this temperature. It is then treated with a solution of 3-(exo)-8,9,10-trinorbornyl-2-oxy-4-(methylthio)benzoyl chloride (2.8 g, that is prepared as described in Reference Example 21) in dry tetrahydrofuran (20 mL) keeping the temperature below 10° C. The resulting mixture is further stirred in the cold for 1 hour, allowed to warm to room temperature and left to stand overnight. The mixture is then quenched with 10% aqueous ammonium chloride solution (150 mL), the layers separated and the aqueous layer further extracted with ethyl acetate (2×100 mL). The combined organic extracts are dried (Na$_2$SO$_4$) and evaporated to dryness. The resulting residue is subjected to flash chromatography on silica gel, eluting with ethyl acetate/pentane (gradient elution 1:4 v/v to 1:1 v/v) to give N-(3,5-dichloropyrid-4-yl)-3-(exo)-8,9,10-trinorbornyl-2-oxy-4-(methylthio)benzamide (2.0 g) as an off white solid, m.p. 175–177° C. (from isopropanol). [Elemental analysis: C,56.7; H,4.8; N,6.6%; calculated: C,56.7; H,4.8; N,6.6%].

By proceeding in a similar manner, but replacing the 3-(exo)-8,9,10-trinorbornyl-2-oxy-4-(methylthio)benzoyl chloride that is used as a starting material by the appropriate benzoyl chloride derivatives (that is prepared as described in Reference Example 21) there is prepared:

(R)-N-(3,5-dichloropyrid-4-yl)-3-(exo)-8,9,10-trinorbornyl-2-oxy-4-(methylthio)benzamide, m.p. 185–186° C. (from ethyl acetate/t-butylmethyl ether), $[a]_D^{21}$ −19.5° (c=0.91, $CH_2Cl_2$). [Elemental analysis: C,56.6; H,14.9; N,6.6%; Calculated: C,56.7; H,4.8; N,6.6%]; and (S)-N-(3,5-dichloropyrid-4-yl)-3-(exo)-8,9,10-trinorbornyl-2-oxy-4-(methylthio)benzamide, m.p. 188–189° C. (from ethyl acetate/heptane) $[a]_D^{20}$ +15.6° (c=1.24, $CH_2Cl_2$). [Elemental analysis: C,57.0; H,4.9; N,6.7%; Calculated: C,56.7; H,4.8; N,6.6%].

EXAMPLE 23

Compound CD

A solution of 4-amino-3,5-dichloropyridine (3.73 g) in dry tetralydrofuran (50 mL) under nitrogen at 5–10° C. is treated portionwise with sodium hydride (60% dispersion in oil; 1.87 g). After 30 minutes it is treated dropwise with a solution of 3-cyclopent-2-enyloxy-4-methoxybenzoyl chloride in dry tetrahydrofuran (50 mL; that is prepared, as described in Reference Example 30, from 5.89 g 3-cyclopent-2-enyloxy-4-methoxybenzoic acid). The resulting mixture is allowed to warm to room temperature and left to stand overnight. Most of the solvent is then removed under reduced pressure and the residue is partitioned between water (250 mL) and dichloromethane (250 mL) and the aqueous layer is further extracted with dichloromethane (2×250 mL). The combined organic layers are dried over sodium sulfate, the solvent is removed under reduced pressure, and the resulting residue is subjected to flash chromatography on silica gel, eluting with mixtures of ethyl acetate and pentane (3:7 to 1:1 v/v), to give a cream solid (1.25 g), which is recrystallized from a mixture of ethyl acetate and pentane, to give (±)-N-(3,5-dichloropyrid-4-yl)-3-cyclopent-2-enyloxy-4-methoxybenzamide (0.80 g), as a white solid, m.p. 177–178° C. [Elemental analysis: C,56.9; H,4.2; N,7.4; Cl,18.6%; calculated: C,57.0; H,4.3; N,7.4; C, 18.7%].

EXAMPLE 24

Compound CE

A solution of 4-amino-3,5-dichloropyridine (0.93 g) in dry tetrahydrofuran (56 mL) under nitrogen at 5–10° C. is treated portionwise with sodium hydride (60% dispersion in oil, 0.57 g). After 1 hour it is treated dropwise with a solution of 3-cyclopent-3-enyloxy-4-methoxybenzoyl chloride in dry tetrahydrofuran (30 mL) prepared as described in Reference Example 33 from 1.33 g 3-cyclopent-3-enyloxy-4-methoxybenzoic acid). The resulting mixture is allowed to warm to room temperature, stirred for a further 3 hours and then poured into 5% aqueous potassium carbonate (430 mL). The resulting emulsion is extracted with ethyl acetate (3×150 mL), the combined organic extracts washed with water (2×20 ml), followed by ice-cold 1M aqueous hydrochloric acid (2×20 mL) and dried over sodium sulfate. The solvent is removed under reduced pressure and the resulting residue subject to flash chromatography on silica gel, eluting with mixtures of t-butyl methyl ether and cyclohexane (2:3 to 7:3 v/v), to give a cream solid, which is recrystallized from acetonitrile to give N-(3,5-dichloropyrid-4-yl)-3-cyclopent-3-enyloxy-4-methoxybenzamide (0.54 g), as a white solid, m.p. 193–195° C. [Elemental analysis: C,56.7; H,4.2; N,7.3%; calculated: C,57.0; H,4.3; N,7.4%].

EXAMPLE 25

Compound CF

A solution of 4-amino-3,5-dichloropyridine (0.27 g) in tetrahydrofuran (7 mL) under nitrogen is treated with sodium hydride (60% dispersion in oil; 0.13 g; 3.2 mmol), portionwise, and stirred at room temperature for 15 minutes. It is then treated dropwise with a solution of 3-cyclopentyloxy-4-difluoromethoxy-benzoyl chloride (0.48 g; that is prepared as described in Reference Example 43) in tetrahydrofuran (5 mL) and the reaction mixture is stirred at room temperature for 3 hours. Tetrahydrofuran is evaporated off under reduced pressure and the crude residue is partitioned between water (40 mL) and ethyl acetate (40 mL). The organic layer is separated and the aqueous layer is extracted with a further quantity of ethyl acetate (40 mL). The combined ethyl acetate extracts are dried over magnesium sulfate, evaporated under reduced pressure and subjected to flash chromatography on silica gel, using a mixture of diethyl ether and pentane (2:3 v/v), to give N-(3,5-dichloropyrid-4-yl)-3-cyclopentyloxy-4-difluoromethoxybenzamide (0.51 g), in the form of a white solid, m.p. 127–129° C. [Elemental analysis: C,51.9; H,3.88; N,6.48%; calculated: C,51.82; H,3.86, N,6.71%].

EXAMPLE 26

Compound CG

A suspension of sodium hydride (60% dispersion in oil; 3.2 g; 80 mmol) in dry tetrahydrofuran (70 mL) under nitrogen at 4° C. is treated with 3,5-dichloro-4-aminopyridine (6.5 g) in dry tetrahydrofuran (80 mL) during 15 minutes and the solution is stirred at room temperature for 1 hour. After cooling to 5° C., it is treated with 3-cyclopentylthio-4-methoxybenzoyl chloride (that is prepared from 9.0 g of 3-cyclopentylthio-4-methoxybenzoic acid as described in Reference Example 47) in dry tetrahydrofuran (80 mL) during 45 minutes, and the temperature is allowed to rise to room temperature. The mixture is treated with a further quantity of tetrahydrofuran (200 mL) and then it is stirred for a further 6 hours. It is then treated with a saturated aqueous solution of ammonium chloride (300 mL), and concentrated in vacuo to low volume. The aqueous residue is extracted with ethyl acetate (2×200 mL). The combined extracts are washed with brine (2×200 mL), dried over magnesium sulfate, and concentrated. The resulting residue is subjected to flash chromatography on silica gel, using a mixture of ethyl acetate and petroleum ether (b.p. 60–80° C.) (1:1 v/v), to give 3-cyclopentylthio-N-(3,5-dichloropyrid-4-yl)-4-methoxybenzamide (2.5 g), in the form of a colorless solid, m.p. 198° C. [Elemental analysis: C,54.5, H,4.6; N,6.95; S,8.2%; calculated: C,54.4; H,4.6; N,7.05; S,8.1%].

EXAMPLE 27

Compound CH

By proceeding in the manner described in Example 26, but using the appropriate quantity of 3-isopropylthio-4- methoxybenzoyl chloride, there is prepared N-(3,5-dichloropyrid-4-yl)-3-isopropylthio-4-methoxybenzamide, in the form of a white solid, m.p. 150–152° C. [Elemental analysis: C,52.1; H,4.4; N,7.5%; calculated: C,51.8, H,4.3; N,7.55%].

EXAMPLE 28

Compound CI

A solution of N-(3,5-dichloropyrid-4-yl)-3-cyclopentyloxy-4-(methylthio)benzamide (1 g; that is prepared as described in Example 20) in dichloromethane (100 mL), containing molecular sieve 4A, under nitrogen, is treated with 2,6-di-tert-butyl-4-methylpyridine (1.28 g). The resulting mixture is stirred at room temperature for 1.5 hours, and then it is cooled to 0° C. (in an ice/salt bath) and treated with xenon difluoride (0.51 g) in one portion. After stirring for a further 2 hours in the cold, the mixture is filtered, and the filtrate is washed with saturated aqueous ammonium chloride solution. The organic phase is dried over sodium sulfate and evaporated. The resulting residue is subjected to flash chromatography, eluting with a mixture of ethyl acetate and pentane (2:3 v/v), to give impure N-(3,5-dichloropyrid-4-yl)-3-cyclopentyloxy-4-(fluoromethylthio)-benzamide (600 mg). It is further purified by reversed phase HPLC on octadecylsilyl silica gel, eluting with a mixture of methanol and water (7:3 v/v), to give N-(3,5-dichloropyrid-4-yl)-3-cyclopentyloxy-4-(fluoromethylthio)benzamide (519 mg), in the form of a white solid, m.p. 111–113° C. [Elemental analysis: C,51.50, H,4.12; N,6.74%; calculated: C,52.05; H,4.12; N,6.74%].

EXAMPLE 29

Compound CJ

A suspension of chromium trioxide (0.6 g) in dichloromethane (25 mL) is treated with 3,5-dimethylpyrazole (0.58 g), and stirred for 20 minutes. It is then treated with a solution of 1-(3-cyclopentyloxy-4-methoxyphenyl)-2-(2,6-dichlorophenyl)ethanol (1.4 g; that is prepared as described in Reference Example 61) in dichloromethane (10 mL) and the solution is stirred overnight at room temperature. It is then concentrated and the resulting residue is triturated with diethyl ether (200 mL) and filtered. The filtrate is evaporated to give a brown oil, which is subjected to flash chromatography, eluting with a mixture of diethyl ether and pentane (1:4 v/v), to give 3-cyclopentyloxy-4-methoxyphenyl 2',6'-dichlorobenzyl ketone (0.36 g), in the form of a white solid, m.p. 135–137° C. [NMR(CDCl$_3$): 7.73(dd,1H,J=8 Hz,J=2 Hz), 7.59(d,1H,J=8 Hz), 7.35(d,2H, J=8 Hz),7.18(t,1H,J=8 Hz),6.94(d,1H,J=8 Hz), 4.85(m,1H), 4.66(s,2H),3.95(s,3H),2.05–1.52(m,8H). Elemental analysis: C,62.9, H,5.3%; calculated: C,63.3,H,5.3%].

EXAMPLE 30

Compound CK

A solution of oxalyl chloride (5.3 mL) in dry dichloromethane (125 mL) at −60° C. is treated portionwise with dimethyl sulfoxide (9.1 mL) in dichloro-methane (20 mL), keeping the temperature below −50° C. The solution is then stirred at −70° C. for 20 minutes and is then treated with a suspension of 1-(3-cyclopentyloxy-4-methoxyphenyl)-2-(3,5-dichloropyrid-4-yl)ethanol (20.5 g; that is prepared as described in Reference Example 63) in dry dichloromethane (300 mL) during 20 minutes, keeping the temperature below −50° C. After stirring for 30 minutes, the solution is treated with triethylamine (35 mL) and allowed to rise to room temperature. It is then treated with water (250 mL) and extracted with ethyl acetate (2×100 mL). The combined organic extracts are washed with dilute sulfuric acid (100 mL; 1%), aqueous potassium carbonate solution (100 ml; 5%) and brine (100 mL), dried and concentrated and the resulting residue is recrystallized from a mixture of ethyl acetate and heptane, to give 3-cyclopentyloxy-4-methoxyphenyl 3,5-dichloropyrid-4-ylmethyl ketone (19.6 g), m.p. 119–120° C. [NMR(CDCl$_3$): 8.52(s,2H),7.69 (dd, 1H,J=8 Hz),7.57(d,1H,J=2 Hz), 6.95(d,1H,J=8 Hz),4.86 (m,1H),4.64(s,2H), 3.95(s,3H),2.05–1.58(m,8H). Elemental analysis: C,59.8,H,4.95,N,3.63%; calculated: C,60.0; H,5.0, N,3.7%].

EXAMPLE 31

Compound CL

Aqueous 27.5% hydrogen peroxide (0.32 mL) is added to a solution of 3-cyclopentyloxy-4-methoxyphenyl 3,5-dichloropyrid-4-ylmethyl ketone (990 mg) in glacial acetic acid (13 mL). The reaction is heated at 80° C. for 8 hours then allowed to stand overnight at room temperature. A further aliquot of aqueous 27.5% hydrogen peroxide (0.32 mL) is added and the mixture heated at 80° C. for 2 hours. The reaction mixture is diluted with ethyl acetate (200 mL) and washed with saturated aqueous sodium bicarbonate until the washings remained basic. The mixture is washed with brine (50 mL), dried (MgSO$_4$), concentrated and the residue recrystallized from a mixture of dichloromethane/ethyl acetate/heptane to give 3,5-dichloro-4-(2-(3-cyclopentyloxy4-methoxyphenyl)-2-oxoethyl)pyridine-N-oxide as a yellow solid, m.p. 179–180° C. [Elemental analysis: C,57.3; H,4.81; N,3.54; Cl,18.0%; calculated for C$_{19}$H$_{19}$Cl$_2$NO$_4$: C,57.59; H,4.83; N,3.53; Cl,1,17.89%.]

EXAMPLE 32

Compound CM

A solution of diisopropylamine (1.23 mL) in dry tetrahydrofuran (15 mL) is stirred and cooled to −70° C. under a nitrogen atmosphere. To this is added a 2.5 M solution of n-butyl lithium in hexanes (3.52 mL) at −70° C. The mixture is stirred for 30 minutes then a solution of 3-chloro-4-methylpyridine (1.02 g) in dry tetrahydrofuran (10 mL) is added. The mixture is stirred for a further 40 minutes. A solution of 3-cyclopentyloxy-4,N-dimethoxy-N-methylbenzamide (2.23 g) in dry tetrahydrofuran (10 mL) is added and the mixture stirred at −70° C. for 30 minutes, −40° C. for 30 minutes, 0° C. for 30 minutes, and room temperature for 1 hour. A mixture of ethanol and hydrochloric acid 19:1 (40 mL) is added and then the reaction mixture is partitioned between brine (40 mL) and diethyl ether (40 mL). The ethereal phase is dried over sodium sulfate and concentrated in vacuo to give a pale yellow solid (3.0 g). The solid is triturated with diethyl ether and then purified by flash chromatography (ethyl acetate eluent on a silica column) to give a solid (1.6 g). The solid is triturated with diethyl ether, collected and dried to afford 1-(3-cyclopentyloxy-4-methoxyphenyl)-2-(3-chloropyrid-4-yl)ethanone (1.35 g) as a cream solid m.p. 124–125° C. [Elemental analysis: C,66.2; H,5.89; N,4.12%; calculated for C$_{19}$H$_{20}$ClNO$_3$: C,65.99; H,5.83; N,4.05%.]

EXAMPLE 33

Compound CN

5% Palladium on carbon (53 mg) is added to a solution of 3-cyclopentyloxy-4-methoxyphenyl 3,5-dichloropyrid-4- ylmethyl ketone (1.9 g) in hot methanol (60 mL) under a nitrogen atmosphere. The mixture is brought to reflux, ammonium formate (1.6 g) is added portionwise during 10 minutes and then refluxing is continued for a further 45 minutes. More 5% palladium on carbon (53 mg) and ammonium formate (1 g) are added and the mixture refluxed for 10 minutes. The reaction mixture is partitioned between dichloromethane (250 mL) and water (100 mL). The organic phase is separated, washed with water (75 mL) and brine (100 mL) and dried over magnesium sulfate. Evaporation yields a yellow gum (1.3 g) which is purified by flash chromatography (ethyl acetate/methanol 19:1 v/v as eluent on a silica column) followed by recrystallization from cyclohexane to give 1-(3-cyclopentyloxy-4-methoxyphenyl)-2-(4-pyridyl) ethanone (0.55 g) as an off-white solid, m.p. 102–103° C. [Elemental analysis: C,72.6; H,6.63; N,4.23%; calculated for $C_{19}H_{21}NO_3$: C,73.29; H,6.80; N,4.50%.]

EXAMPLE 34

Compound CO

A solution of 3-cyclopentyloxy-4-methoxybenzonitrile (1.09 g) in dry tetrahydrofuran (3 mL) is added to a 2 M solution of benzylmagnesium chloride in tetrahydrofuran (5.0 mL) at room temperature under a nitrogen atmosphere. The mixture is refluxed for 3 hours, cooled in an ice bath and quenched with cold 4 M aqueous hydrochloric acid. More tetrahydrofuran (20 mL) is added and the reaction mixture is allowed to stand at room temperature for 48 hours. The tetrahydrofuran layer is decanted and evaporated. The residue is dissolved in cyclohexane (50 mL) and the solution washed successively with water (2×10 mL), 5% aqueous sodium bicarbonate (2×10 mL), water (2×10 mL) and brine (10 mL), and finally dried over magnesium sulfate. Concentration affords an amber oil (1.53 g) which is purified by flash chromatography (dichloromethane as eluant on silica column) to give a pale yellow viscous oil which crystallized on standing. The solid is recrystallized from methanol to afford 1-(3-cyclopentyloxy-4-methoxyphenyl)-2-phenylethanone as colorless crystals, m.p. 117–119° C. [Elemental analysis: C,77.7; H,7.2%; calculated for $C_{20}H_{22}O_3$: C,77.39; H,7.14%.]

EXAMPLE 35

Compound CP

By proceeding in a manner similar to that described in Example 51, but using as the starting material the appropriate quantity of 3-(3-methyl-2-butenyloxy)-4-methoxybenzoic acid, there is prepared 3-(3-methyl-2-butenyloxy)-N-(3,5-dichloropyrid-4-yl)-4-methoxybenzamide, in the form of a white solid, m.p. 173–174° C. [Elemental analysis: C,56.7; H,4.9; N,7.3%; calculated: C,56.7; H,7.8; N,7.35%].

EXAMPLE 36

Compound CQ

By proceeding in a manner similar to that described in Reference Example 47 (in the presence of a few drops of dimethylformamide) and Example 20, but using as the starting material the appropriate quantity of 3-[exobicyclo-(2.2.1)hept-5-en-2-yloxy]-4-methoxybenzoic acid, there is prepared N-(3,5-dichloropyrid-4-yl)-3-[exobicyclo(2.2.1)-hept-5-en-2-yloxy]-4-methoxybenzamide, in the form of white crystals, m.p. 175–176° C. [Elemental analysis: C,59.3; H,4.6; N,6.7; %; calculated: C,59.3; H,4.5; N,6.9%].

EXAMPLE 37

Compound CR

A stirred solution of 3-cyclopentyloxy-4-methoxyaniline (1 g) and triethylamine (0.69 mL) in dry dichloromethane (20 mL) at 0° C. is treated dropwise with 2,6-dichlorobenzoyl chloride (1.17 g). After stirring at this temperature for 30 minutes, the mixture is warmed to room temperature and stirred for a further 3 hours. The organic layer is washed with water (100 mL), dried and concentrated. The residue is recrystallized from a mixture of isopropanol and hexane, to give N-(3-cyclopentyloxy-4-methoxyphenyl)-2,6-dichlorobenzamide (0.6 g), m.p. 184–185° C. [Elemental analysis: C,60.2, H,5.0; N,3.6; Cl,18.9%; calculated: C,60.0; H,5.0; N,3.7; Cl,18.65%].

EXAMPLE 38

Compound CS

By proceeding in a similar manner to that described in Example 37, but using 2,6-difluorobenzoyl chloride, there is prepared N-(3-cyclopentyloxy-4-methoxyphenyl)-2,6-difluorobenzamide, m.p. 150–151° C. [Elemental analysis: C,65.4; H,5.6; N,3.95;F,10.8%; calculated: C,65.7; H,5.5; N,4.0;F,10.9%].

EXAMPLE 39

Compound CT

A stirred solution of 3-cyclopentyloxy-4-methoxyaniline (1 g) and triethylamine (0.69 mL) in dry dichloromethane (20 mL) is treated dropwise at 0–5° C. with a solution of 2,6-dichlorophenyl isocyanate (0.9 g) in dry dichloromethane (10 mL). The resulting mixture is stirred for 30 minutes at this temperature and then for 6 hours at room temperature. The precipitate which forms is collected and stirred with isopropanol (50 mL), with ice cooling. The resulting solid is collected and dried, to give N-(2,6-dichlorophenyl)-N'-(3-cyclopentyloxy-4-methoxyphenyl) urea (1.06 g), m.p. 203–204° C. [Elemental analysis: C,57.2; H,5.0; N,7.0; Cl,18.2%; calculated: C,57.7; H,5.1; N,7.1; Cl,18.0%].

EXAMPLE 40

Compound CU

A stirred solution of bis(trichloromethyl) carbonate (0.96 g) in dichloromethane (10 mL) at room temperature is treated with a solution of 3-cyclopentyloxy-4-methoxyaniline (2.0 g) in dichloromethane (10 mL) and then the mixture is stirred for a further 30 minutes during which time a thick precipitate forms. The mixture is diluted with dichloromethane, washed with water (50 mL), dried over magnesium sulfate, and filtered. The solvent is removed in vacuo, to give a light brown oil, which is dissolved in dry tetrahydrofuran (10 mL) to give "solution A".

A stirred solution of 4-amino-3,5-dichloropyridine (1.56 g) in dry tetrahydrofuran (20 mL) under nitrogen at room temperature is treated portionwise with an oil dispersion of sodium hydride (60%; 0.37 g; 10 mmol). After stirring for 15 minutes, the mixture is treated dropwise with "solution A" and then stirred for a further 2 hours, during which time a thick cream precipitate forms. This is filtered off, washed with diethyl ether (20 mL), and then with acetone (20 mL) and dried in vacuo. Recrystallization from methanol gives N-(3,5-dichloropyrid-4-yl)-N'-(3-cyclopentyloxy-4- methoxyphenyl)urea (0.68 g), m.p. 183–184° C. [Elemental analysis: C,54.4; H,4.8; N,10.4; Cl,17.7%; calculated: C,54.6; H,4.8; N,10.6; Cl,17.9%].

EXAMPLE 41

Compound CV

A stirred solution of 3-cyclopentyloxy-4-methoxyphenol (0.2 g) and triethylamine (1.35 mL) in dichloromethane (5 mL) is treated portionwise at 0–5° C. with 2,6-dichlorobenzoyl chloride (0.28 g), and the solution is warmed to room temperature and stirred for a further 2 hours. The reaction mixture is poured into hydrochloric acid (50 ml; 2 N) and is extracted with diethyl ether (3×50 mL). The combined organic extracts are then washed with water (100 mL), and brine (100 mL), dried over magnesium sulfate and concentrated. The residual oil is subjected to flash chromatography on silica gel, eluting with a mixture of pentane and ethyl acetate (4:1 v/v), to give (3-cyclopentyloxy-4-methoxyphenyl) 2,6-dichlorobenzoate (0.28 g), m.p. 100–101° C. [Elemental analysis: C,59.7; H,4.7%; calculated: C,59.9; H,4.8%].

EXAMPLE 42

Compound CW

A stirred solution of 3-cyclopentyloxy-4-methoxyphenol (0.5 g), potassium carbonate (0.4 g) and alpha 2,6-trichlorotoluene (0.56 g) in dimethylformamide (5 mL) is heated at 100° C. for 1 hour. The solution is then concentrated and the residue is subjected to flash chromatography, eluting with a mixture of dichloromethane and pentane (1:1 v/v), to give 3-cyclopentyloxy-4-methoxyphenyl-2,6-dichlorobenzyl ether (0.76 g), m.p. 96–98° C. [Elemental analysis: C,61.7; H,5.5%; calculated: C,62.1; H,5.5%].

EXAMPLE 43

Compound CX

A solution of 3-cyclopentyloxy-4-methoxybenzaldehyde (5 g) and 2-chloroaniline (2.5 mL) in toluene (60 mL) is heated at reflux under a Dean and Stark water trap for 3 hours. After concentration. the residue is dissolved in methanol (60 mL) and the stirred solution is treated at 0° C. with sodium cyanoborohydride (2.1 g). The temperature is allowed to rise to room temperature, and the stirring is continued for 2 hours, before dilution with ethyl acetate (100 mL) and washing with saline (100 mL). The organic layer is dried and concentrated, to give a brown oil. This oil is subjected to flash chromatography on silica gel, eluting with a mixture of ethyl acetate and hexane (1:4 v/v), to give N-(2-chlorophenyl)-3-cyclopentyloxy-4-methoxybenzylamine (0.64 g), in the form of an oil. [Elemental analysis: C,69.5; H,6.8; N,4.1; Cl,10.6%; calculated: C,68.8; H,6.7; N,3.2; Cl,10.7%].

EXAMPLE 44

Compound CY

A stirred suspension of 2,6-dichlorobenzyltriphenylphosphonium bromide (2.5 g) in dry tetrahydrofuran (30 mL) is treated dropwise with a solution of potassium t-butoxide (0.56 g) in dry tetrahydrofuran (32 mL) at 0° C. After stirring at this temperature for 1 hour, it is treated with a solution of 3-cyclopentyloxy-4-methoxybenzaldehyde (1.1 g) in dry tetrahydrofuran (15 mL). The reaction mixture is stirred from 0° C. to 5° C. for 1 hour and 30 minutes, and then allowed to warm to room temperature. After stirring overnight, the mixture is concentrated and the resulting residue is treated with ethyl acetate (200 mL). The resulting organic solution is filtered. The filtrate is concentrated and the resulting residue is subjected to flash chromatography, eluting with dichloromethane, to give trans-1-(3-cyclopentyloxy-4-methoxyphenyl)-2-(2,6-dichlorophenyl)ethene (1.16 g), m.p. 47–49° C. [Elemental analysis: C,66.4; H,5.6; Cl,19.4%, calculated: C,66.1; H,5.55; Cl,19.5%].

EXAMPLE 45

Compound CZ

By proceeding in a manner similar to that described in Example 44, but using 2,6-difluorobenzyltriphenylphosphonium bromide, there is prepared trans-1-(3-cyclopentyloxy-4-methoxyphenyl)-2-(2,6-difluorophenyl)ethene, m.p. 65–67° C. [Elemental analysis: C,73.0; H,6.1 %; calculated: C,72.7; H,6.1%]).

EXAMPLE 46

Compound DA

Pyridinium dichromate (3.6 g) in dry dichloromethane (40 mL) under nitrogen is treated with (±)-1-(3-cyclopentyloxy-4-methoxyphenyl)-2-(pyrid-4-yl)ethanol (2.0 g; that is prepared as described in Reference Example 67), in one portion. The resulting mixture is stirred for 1 hour and 30 minutes, and then filtered through a pad of diatomaceous earth, and the pad is washed with diethyl ether. The combined filtrate and ethereal washings are washed with saturated aqueous cupric sulfate solution (2×30 mL), followed by water (30 mL), and then dried over magnesium sulfate. The solvent is removed under reduced pressure, and the resulting oily residue is subjected to flash chromatography on silica gel, eluting with ethyl acetate, to give 1-(3-cyclopentyloxy-4-methoxyphenyl)-2-(pyrid- 4-yl)ethane-1, 2-dione (0.4 g), in the form of a yellow solid, m.p. 117–119° C. [Elemental analysis: C,70.1; H,6.0; N,4.1%; calculated: C,70.1; H,5.9; N,4.3%].

EXAMPLE 47

Compound DB

A stirred solution of diisopropylamine (3.6 mL) in dry tetrahydrofuran (132 mL) is treated with a solution of butyl lithium in hexanes (10.3 mL; 2.5 M), dropwise, under nitrogen, keeping the temperature below –65° C. The resulting mixture is then stirred for a further period of 20 minutes, at below –65° C. The stirred mixture, still maintained at below –65° C., is then treated dropwise with a solution of 3,5-dichloropyridine (3.5 g) in dry tetrahydrofuran (24 mL). The stirred mixture is maintained at below –65° C. for a further 30 minutes. The stirred mixture, still maintained at below –65° C., is then treated portionwise with 3-cyclopentyloxy-4-methoxyphenyldiazonium tetrafluoroborate (7.2 g), and it is stirred at below –65° C. for a further 45 minutes. The resulting mixture is then allowed to warm to room temperature overnight. It is then treated with water (600 mL), the layers are separated, and the aqueous layer is further extracted with diethyl ether (3×100 mL). The combined organic extracts are washed with saturated aqueous sodium chloride solution (100 mL), dried over magnesium sulfate, and then evaporated to dryness. The resulting residue is subjected to flash chromatography on silica gel, eluting with a mixture of pentane and diethyl ether (2:1 v/v), to give a red solid (3.1 g) which, on recrystallization from pentane, gives trans-1-(3-cyclopentyloxy-4-methoxyphenyl)2-(3,5-dichloropyrid-4-yl)diazene (2.2 g), in the form of a red-brown solid, m.p. 88–89° C. [Elemental analysis: C,56.0; H,4.8; N,11.3%; calculated: C,55.75; H,4.7; N,11.5%].

EXAMPLE 48

Compounds DC and DD

A solution of trans-1-(3-cyclopentyloxy-4-methoxyphenyl)-2-(3,5-dichloropyrid-4-yl)diazene (1.2 g; that is prepared as described in Example 47) in dichloromethane (24 mL) is treated portionwise with metachloroperbenzoic acid (0.6 g). The resulting mixture is stirred in the dark for 2 hours and 30 minutes, and then it is allowed to stand in the dark overnight. After the addition of a further quantity of dichloromethane (24 mL), the mixture is shaken with saturated aqueous sodium bicarbonate solution (12 mL). The layers are separated and the aqueous phase is further extracted with dichloromethane (3×6 mL). The combined organic extracts are washed with saturated aqueous sodium carbonate solution (6 mL), dried over magnesium sulfate, and evaporated to dryness. The resulting residual gum is dissolved in a mixture of dichloromethane and diisopropyl ether (1:2 v/v), and treated with activated carbon. After filtration, the solution is concentrated to low bulk. The resulting crystalline solid is filtered off and washed with diisopropyl ether and pentane, and dried in air. This material (0.71 g) is subjected to flash chromatography on silica gel, eluting initially with dichloromethane, and then with a mixture of dichloromethane and methanol (19:1 v/v), to give a solid (0.58 g), which is purified by reverse phase high pressure liquid chromatography on octadecylsilyl silica gel, eluting with a mixture of methanol and water (3:1 v/v).

1-(3-Cyclopentyloxy-4-methoxyphenyl)-c-1-oxo-r-2-(3,5-dichloro-1-oxopyrid-4-yl)diazene (0.17 g) is eluted first, in the form of a yellow solid, m.p. 139–141° C. [Elemental analysis: C,51.4; H,4.4; N,10.4%; calculated: C,51.3; H,4.3; N,10.6%].

Trans-1-(3-cyclopentyloxy-4-methoxyphenyl)-2-(3,5-dichloro-1-oxopyrid-4-yl)diazene (0.31 g) is eluted second, in the form of a red solid, m.p. 172–174° C. [Elemental analysis: C,53.4; H,4.5; N,10.9%; calculated: C,53.4; H,4.5; N,11.0%].

EXAMPLE 49

Compound DE

A stirred solution of N-(3-hydroxy-4-methoxyphenylsulfonyl)-2-chloroaniline, containing some N,N-bis(3-hydroxy-4-methoxyphenyl-sulfonyl)-2-chloroaniline (0.7 g; that is prepared as described in Reference Example 72) in dimethylformamide (20 mL) is treated portionwise with an oil dispersion of sodium hydride (60%; 0.11 g, 2.7 mmol) and the mixture is stirred at 60° C. for 1 hour. It is then treated dropwise with cyclopentyl bromide (0.32 mL) and the solution is stirred at 60° C. for a further period of 4 hours. After cooling, the mixture is treated with water (20 mL) and extracted with diethyl ether (2×75 mL). The organic extracts are combined, dried and evaporated, to give an oil which is subjected to flash chromatography on silica gel, eluting with diethyl ether, to give N-(2-chlorophenyl)-3-cyclopentyloxy-4-methoxybenzenesulfonamide (150 mg), m.p. 113–115° C. [NMR(CDCl$_3$): 7.68(dd,1H,J=8 Hz,J=2 Hz),7.37(dd,1H,J=8 Hz,J=2 Hz), 7.26(d,1H, J=2 Hz), 7.24(dt,1H,J=8 Hz,J=2 Hz), 7.13(d,1H,J=2 Hz),7.04(dt,1H, J=8 Hz,J=2 Hz),6.92 (bs,1H), 6.82(d,1H,J=8 Hz),4.65(m,1H), 3.86(s,3H), 1.92–1.55 (m,8H)].

EXAMPLE 50

Compound DO

Sodium hydride (0.14 g) is added to a solution of 3,5-dichloro-4-aminopyridine (0.28 g) in dimethylformamide (7 mL) under nitrogen and the mixture is stirred at room temperature for 15 minutes. A solution of 3-cyclopentyloxy-4-trifluoromethoxybenzoyl chloride (0.54 g) in dimethylformamide (3 mL) is then added dropwise and the mixture is stirred at room temperature for 3 hours. Water (50 mL) is added and the mixture is extracted with ethyl acetate (2×75 mL). The combined extracts are dried over magnesium sulfate and evaporated under reduced pressure, to give a brown oil, which is subjected to mplc, eluting with a mixture of diethyl ether and pentane (3:7 v/v), to give N-(3,5-dichloropyrid-4-yl)-3-cyclopentyloxy-4-trifluoromethoxybenzamide (0.6 g), in the form of a white solid. m.p. 129–131° C., Elemental analysis: C,50.0; H,3.5; N,6.6; Cl,16.3%; calculated: C,49.7; H,3.5; N,6.4; Cl,16.2%].

EXAMPLE 51

Compound DP

A stirred solution of 3-(4,4-difluoro-3-methylenecyclobut-1-enyloxy)-4-methoxybenzoic acid (0.7 g) in acetone (24 mL) is treated with triethylamine (0.4 mL) and cyanuric chloride (0.24 g) and the solution is stirred for 4 hours at room temperature. The precipitated solid is filtered off and the filtrate is evaporated to dryness in vacuo. The residue is treated with dry tetrahydrofuran (12 mL) and filtered, to give "solution A", containing 3-(4,4-difluoro-3-methylenecyclobut-1-enyloxy)-4-methoxy-benzoyl chloride.

A stirred solution of 3,5-dichloro-4-aminopyridine (0.42 g) in dry tetrahydrofuran (24 mL) at room temperature is treated with sodium hydride (60% dispersion in oil; 0.21 g), portionwise, under nitrogen and stirred for 2 hours. It is then treated, dropwise, with "solution A" and stirred at room temperature for 3 hours. The reaction mixture is diluted with water (100 mL) and extracted with ethyl acetate (2×50 mL). The extract is washed with water, dried over magnesium sulfate and concentrated. The residue is subjected to flash chromatography, eluting with a mixture of diethyl ether and pentane (1:1 v/v), to give N-(3,5-dichloropyrid-4-yl)-3-(4,4-difluoro-3-methylenecyclobut-1-enyloxy)-4-methoxybenzamide (0.44 g), m.p. 102–104° C. [Elemental analysis: C,52.4; H,3.15; Cl,16.8; N,6.7%; calculated: C,52.3; H,2.9; Cl,16.8; N,6.7%].

EXAMPLE 52

Compound DQ

By proceeding as described in Example 25, but using the appropriate quantities of 3-isopropoxy-4-difluoromethoxybenzoic acid and 4-amino-3,5-difluoropyridine, there is prepared N-(3,5-difluoropyrid-4-yl)-3-isopropoxy-4-difluoromethoxybenzamide, in the form of a white solid, m.p. 101–103° C., [Elemental analysis: C,53.7; H,4.0; N,7.7%; calculated: C,53.6; H,3.9; N,7.8%].

EXAMPLE 53

Compound DR

By proceeding as described in Example 9, but using the appropriate quantity of N-(3,5-difluoropyrid-4-yl)-3-isopropoxy-4-difluoromethoxy-benzamide, there is prepared N-(3,5-difluoro-1-oxido-4-pyridinio)-3-isopropoxy-4-difluoromethoxybenzamide in the form of a white solid, m.p. 55° C., [Elemental analysis: C,50.2; H,3.7; N,7.5%; calculated (for a form containing 0.5 molecules of water per molecule): C,50.1; H,4.0; N,7.3%].

EXAMPLE 54

Compound DS

By proceeding as described in Reference Example 3 and Example 25, but using the appropriate quantities of 3-isopropoxy-4-difluoromethoxybenzoic acid and 4-amino-3,5-dichloropyridine, there is prepared N-(3,5-dichloro-pyrid-4-yl)-3-isopropoxy-4-difluoromethoxybenzamide, in the form of a white solid, m.p. 113–114° C., [Elemental analysis: C,49.3; H,3.7; N,7.1%; calculated: C,49.1; H,3.6; N,7.1%].

EXAMPLE 55

Compound DT

By proceeding as described in Example 9, but using the appropriate quantity of N-(3,5-dichloropyrid-4-yl)-3-isopropoxy-4-difluoromethoxy-benzamide, there is prepared N-(3,5-dichloro-1-oxido-4-pyridinio)-3-isopropoxy-4-difluoromethoxybenzamide, in the form of a white solid, m.p. 138–140° C., [Elemental analysis: C,46.1; H,3.7; Cl,17.0; N,6.8%; calculated (for a form containing 0.5 molecules of water per molecule): C,46.2; H,3.6; Cl,17.0; N,6.7%].

EXAMPLE 56

Compound DU

By proceeding as described in Example 25, but using the appropriate quantity of 3-(exo)-8,9,10-trinorbom-2-yloxy-4-difluoro-methoxybenzoic acid, there is prepared N-(3,5-dichloro-4-pyridyl)-4-difluoromethoxy-3-(exo)-8,9,10-trinorborn-2-yloxybenzamide in the form of a white solid, m.p. 152–154° C., [Elemental analysis: C,54.4; H,4.1; N,6.3%; calculated: C,54.2; H,4.1; N,6.3%].

EXAMPLE 57

Compound DV

By proceeding as described in Example 9, but using the appropriate quantity of N-(3,5-dichloro-4-pyridyl)-4-difluoromethoxy-3-(exo)-8,9,10-tri-norborn-2-yloxybenzamide, there is prepared N-(3,5-dichloro-1-oxido-4-pyridinio)-4-difluoromethoxy-3-(exo)-8,9,10-trinorborn-2-yloxybenzamide, m.p. 101–103° C.

EXAMPLE 58

Compound DW

A suspension of 3-(2-fluorocyclopentyloxy)-4-methoxybenzoic acid (0.48 g) in toluene (20 mL) is treated with thionyl chloride (0.34 g) and then is heated at 60° C. for 3 hours, and cooled and evaporated to give 3-(2-fluorocyclopentyl-oxy)-4-methoxybenzoyl chloride.

A suspension of sodium hydride (0.3; 60% oil dispersion) in dimethylformamide (5 mL) is treated with 4-amino-3,5-dichloropyridine (0.62 g) and the mixture is stirred for 40 minutes. A solution of 3-(2-fluoro-cyclopentyloxy)-4-methoxybenzoyl chloride in dimethylformamide (12 mL) is added, and the mixture is stirred at 80–90° C. for 1 day. The solution is cooled, poured into water (75 mL) and extracted with dichloromethane (3×50 mL). The combined organic extracts are washed with brine (50 mL), dried over magnesium sulfate and concentrated. The residue is subjected to flash chromatography, eluting with a mixture of ethyl acetate and petroleum ether (1:3 v/v), to give N-(3,5-dichloropyrid-4-yl)-3-(2-fluorocyclopentyloxy)-4-methoxybenzamide (0.26 g), m.p. 167–169° C. [Elemental analysis: C,53.8; H,4.2; N,6.75; Cl,17.8%; calculated: C,54.15; H,4.3; N,7.0; Cl,17.8%].

EXAMPLE 59

Compound DX

By proceeding in a similar manner as in Example 58, but using the appropriate quantity of 3-(tetrahydrothiophen-3-oxy)-4-methoxybenzoic acid, there is prepared N-(3,5-dichloro-pyrid-4-yl)-3-(tetrahydrothiophen-3-oxy)-4-methoxybenzamide, in the form of a white solid, m.p. 160–162° C., [Elemental analysis: C,51.1; H,4.0; Cl,17.6; N,7.2%; calculated: C,51.1; H,4.0; Cl,17.8; N,7.0%].

EXAMPLE 60

Compound DY

By proceeding in a similar manner to Example 9, but using 3-cyclopentyloxy-N-(3,5-dichloropyrid-4-yl)-4-difluoromethoxy-benzamide as the starting material, there is prepared 3-cyclopentyloxy-N-(3,5-dichloro-1-oxido-4-pyridinio)-4-difluoromethoxybenzamide, in the form of a white solid (m.p. 119–121° C.).

EXAMPLE 61

Compound DZ

By proceeding in a manner similar to that described in Example 20, but using as the starting material the appropriate quantity of 3-isopropoxy-4-(methylthio)benzoyl chloride, there is prepared N-(3,5-dichloropyrid-4-yl)-3-isopropoxy-4-(methylthio)benzamide, in the form of a white solid, m.p. 146–148° C. [Elemental analysis: C,51.9; H,4.5; N,7.4; Cl,18.8; S,8.5%; calculated: C,51.7; H,4.3; N,7.5; Cl,19.1%].

EXAMPLE 62

Compound EA

By proceeding in a manner similar to that described in Example 20, but using as the starting material the appropriate quantities of 3-isopropoxy-4-(methylthio)benzoyl chloride and 4-amino-3,5-difluoropyridine, there is prepared N-(3,5-difluoropyrid-4-yl)-3-isopropoxy-4-(methylthio) benzamide, in the form of a white solid, m.p. 175–177° C. [Elemental analysis: C,56.6; H,4.8; N,8.2; S,9.7%; calculated: C,56.8; H,4.8; N,8.3; S,9.5%].

EXAMPLE 63

Compound EB

By proceeding in a manner similar to that described in Example 20, but using as the starting material the appropriate quantity of 3-(pent-3-yloxy)-4-(methylthio)benzoyl chloride, there is prepared N-(3,5-dichloropyrid-4-yl)-3-(pent-3-yloxy)-4-(methylthio)benzamide, in the form of a white solid, m.p. 154–155° C. [Elemental analysis: C,53.8; H,4.9; N,7.0; S,7.8%; calculated: C,54.14; H,5.05; N,7.0; S,8.0%].

EXAMPLE 64

Compound EC

By proceeding in a manner similar to that described in Example 30, but using as the starting material the appropriate quantity of rac-1-[3-{(exo)-8,9,10-trinorbornyl-2-oxy}-4-methoxyphenyl]-2-(3,5-dichloropyrid-4-yl)ethanol there is prepared, after flash chromatography, eluting with a mixture of ethyl acetate and pentane (1:2 v/v), (±)-1-[3-{(exo)-8,9,10-trinorbornyl-2-oxy}-4-methoxyphenyl]-2-(3,5-dichloropyrid-4-yl)ethanone, in the form of a white solid, m.p. 113–114° C. [Elemental analysis: C,61.9; H,5.2; N,3.4%; calculated: C,62.1; H,5.2; N,3.4%].

EXAMPLE 65

Compound ED

By proceeding in a manner similar to that described in Example 30, but using as the starting material the appropriate quantity of 1-(3-cyclopentyloxy-4-methoxyphenyl)-2-(3,5-dichloropyrid-4-yl)ethanol, there is prepared 1-[3-cyclopentyloxy-4-(methylthio)phenyl]-2-(3,5-dichloropyrid-4-yl)ethanone in the form of a yellow solid, m.p. 110–111° C. [Elemental analysis: C,57.6; H,4.8; Cl,17.8; N,3.4;%; calculated: C,57.6; H,4.8; Cl,17.9; N,3.5%].

EXAMPLE 66

Compound EE

By proceeding in a manner similar to that described in Example 30, but using as the starting material the appropriate quantity of 1-(4-methoxy-3-prop-2-yloxyphenyl)-2-(3,5-dichloropyrid-4-yl)ethanol, there is prepared 1-(4-methoxy-3-prop-2-yloxyphenyl)-2-(3,5-dichloropyrid-4-yl)ethanone, in the form of a buff solid, m.p. 153–155° C. [Elemental analysis: C,56.9; H,4.83; N,3.85%; calculated: C,57.64; H,4.84; N,3.95%].

EXAMPLE 67

Compound EF

By proceeding in a manner similar to that described in Example 30, but using as the starting material the appropriate quantity of 1-(4-methylthio-3-prop-2-yloxyphenyl)-2-(3,5-dichloropyrid-4-yl)ethanol, there is prepared 1-(4-methylthio-3-prop-2-yloxyphenyl)-2-(3,5-dichloropyrid-4-yl)ethanone, in the form of a white solid, m.p. 116–117° C. [Elemental analysis: C,55.0; H,4.59; Cl,19.1; N,3.68; S,8.6%; calculated: C,55.14; H,4.63; Cl,19.2; N,3.78; S,8.7%].

EXAMPLE 68

Compound EG

Hydrogen peroxide (8 mL) is added to a stirred suspension of 1-(4-methoxy-3-prop-2-yloxyphenyl)-2-(3,5-dichloropyrid-4-yl)ethanone (5.97 g) in glacial acetic acid (17 mL). The mixture is stirred at 70–80° C. for 3 hours. After cooling, the mixture is basified by treatment with aqueous sodium hydroxide (6 M), and extracted with ethyl acetate. The extracts are washed with brine, dried over magnesium sulfate and evaporated, to give a white solid which is triturated with pentane and dried at 80° C., to give 1-(4-methoxy-3-prop-2-yloxyphenyl)-2-(3,5-dichloro-1-oxido-4-pyridinio)ethanone, in the form of a white solid, m.p. 167–169° C. [Elemental analysis: C,55.4; H,4.61; Cl,19.3; N,3.72%, calculated: C,55.15; H,4.63; Cl,19.2; N,3.78%].

EXAMPLE 69

Compound EH

By proceeding in a manner similar to that described in Example 30, but using as the starting material the appropriate quantity of 1-(3-cyclopentyloxy-4-difluoromethoxyphenyl)-2-(3,5-dichloropyrid-4-yl)-ethanol, there is prepared 1-(3-cyclopentyloxy-4-difluoromethoxyphenyl)-2-(3,5-dichloropyrid-4-yl)ethanone, in the form of a white solid, m.p. 80–82° C. [Elemental analysis: C,55.1; H,4.1; N,3.2; %; calculated: C,54.8; H,4.1; N,3.4%].

EXAMPLE 70

Compound EI

By proceeding in a manner similar to that described in Example 9, but using as the starting material the appropriate quantity of 1-(3-cyclopentyloxy-4-difluoromethoxyphenyl)-2-(3,5-dichloropyrid-4-yl)ethanone, there is prepared 1-(3-cyclopentyloxy-4-difluoromethoxy-phenyl)-2-(3,5-dichloro-1-oxido-4-pyridinio)ethanone, in the form of a white solid, m.p. 178–179° C. [Elemental analysis: C,53.1; H,4.1; N,3.1;%; calculated: C,52.8; H,4.0; N,3.2%].

EXAMPLE 71

Compound EJ

By proceeding in a manner similar to that described in Example 30, but using as the starting material the appropriate quantity of 2-(3,5-dichloro-pyrid-4-yl)-1-[3-{exobicyclo(2.2.1)hept-5-en-2-yloxy}-4-methoxyphenyl]ethanol, there is prepared 2-(3,5-dichloropyrid-4-yl)-1-[3-{exobicyclo(2.2.1)hept-5-en-2-yloxy}-4-methoxyphenyl]ethano in the form of a white solid, m.p. 89–91° C. [Elemental analysis: C,62.6; H,4.75; N,3.4%; calculated: C,62.4; H,4.7; N,3.5%].

EXAMPLE 72

Compound EK

By proceeding in a manner similar to that described in Example 30, but using as the starting material the appropriate quantity of 2-(3,5-dichloro-4-pyridyl)-1-[4-difluoromethoxy-3-(exo)-8,9,10-trinorborn-2-yloxyphenyl] ethanol, there is prepared 2-(3,5-dichloro-4-pyridyl)-1-(4-difluoromethoxy-3-(exo)-8,9,10-trinorborn-2-yloxyphenyl) ethanone, in the form of a white solid, m.p. 120–122° C.

EXAMPLE 73

Compound EL

By proceeding in a manner similar to that described in Example 9, but using as the starting material the appropriate quantity of 2-(3,5-dichloro-4-pyridyl)-1-[4-difluoromethoxy-3-(exo)-8,9,10-trinorborn-2-yloxyphenyl] ethanol, there is prepared 2-(3,5-dichloro-1-oxido-4-pyridinio)-1-[4-difluoromethoxy-3-(exo)-8,9,10-trinorbom-2-yloxyphenyl]ethanone, in the form of a white solid, m.p. 59–61° C.

EXAMPLE 74

Compound EM

By proceeding in a manner similar to that described in Example 30, but using as the starting material the appropriate quantity of 2-(3,5-dichloro-4-pyridyl)-1-[4-methoxy-3-(3-methyl-2-butenyloxy)-phenyl]ethanol, there is prepared 2-(3,5-dichloro-4-pyridyl)-1-[4-methoxy-3-(3-methyl-2-butenyloxy)-phenyl]ethanone, in the form of a white solid, m.p. 115–117° C.

EXAMPLE 75

Compound EN

By proceeding in a manner similar to that described in Example 30, but using as the starting material the appropriate quantity of 2-(3,5-dichloro-4-pyridyl)-1-(4-difluoromethoxy-3-isopropoxyphenyl)-ethanol, there is prepared 2-(3,5-dichloro-4-pyridyl)-1-(4-difluoromethoxy-3-isopropoxyphenyl)ethanone in the form of a white solid, m.p. 85–87° C. [Elemental analysis: C,52.7; H,3.85; N,3.6%; calculated: C,52.3; H,3.9; N,3.6%].

EXAMPLE 76

Compound EO

By proceeding in a manner similar to that described in Example 9, but using as the starting material the appropriate quantity of 2-(3,5-dichloro-4-pyridyl)-1-(4-difluoromethoxy-3-isopropoxyphenyl)-ethanone there is prepared 2-(3,5-dichloro-1-oxido-4-pyridinio)-1-(4-difluoromethoxy-3-isopropoxyphenyl)-ethanone, in the form of a white solid, m.p. 138–140° C. [Elemental analysis: C,50.3; H,3.7; N,3.2; Cl,17.6%; calculated: C,50.2; H,3.7; N,3.45; Cl,17.45%].

EXAMPLE 77

Compound EP

By proceeding in a manner similar to that described in Example 42, but using as the starting material the appropriate quantity of 4-bromomethyl-3,5-dichloropyridine, there is prepared 3,5-dichloro-4-(3-cyclopentyloxy-4-methoxyphenoxymethyl)pyridine, in the form of a white solid, m.p. 75–77° C.

EXAMPLE 78

Compound EQ

By proceeding in a manner similar to that described in Example 9, but using as the starting material the appropriate quantity of N-(3,5-dichloro-pyrid-4-yl)-3-(exo)-8,9,10-trinorborn-2-yloxybenzamide, there is prepared N-(3,5-dichloro-1-oxido-4-pyridinio-4-methoxy-3-(exo)-8,9,10-trinorborn-2-yloxy-benzamide, m.p. 130–132° C.

Reference Example 1

A stirred solution of 3-hydroxy-4-methoxybenzaldehyde (2.00 g) in dry dimethylformamide (20 mL) is treated portionwise with sodium hydride (60% dispersion in oil; 0.56 g) and the mixture is then heated for 1 hour at 50° C. It is then treated dropwise with cyclopentyl bromide (2.36 g) and is stirred and heated at 50° C. for 22 hours. The solution is diluted with water (100 mL) and extracted with diethyl ether (2×100 mL). The ethereal extracts are combined, dried over magnesium sulfate and concentrated, to give 3-cyclopentyloxy-4-methoxybenzaldehyde (1.65 g) in the form of a golden oil.

By proceeding in a similar manner, but using the appropriate quantities of cyclohexyl bromide, butyl bromide and propyl bromide, respectively, there are prepared:

3-cyclohexyloxy-4-metboxybenzaidehyde in the form of a golden oil [Elemental analysis: C,71.8; H,7.8%; Calculated: C,71.8; H,7.7%];

3-butoxy-4-methoxybenzaldehyde in the form of a light brown oil [NMR(CDCl$_3$): 1.0(t,3H),1.5(m,2H), 1.9(m, 2H), 3.96(s,3H), 4.1 (t,2H),6.96(d,1H),7.4(m,2H),9.8 (s,1H)]; and 3-propoxy-4-methoxybenzaldehyde [NMR(CDCl$_3$): 9.85 (s,1H),7.4(dd,1H),7.4(d,1H), 7.0(d,1H),4.05(t,2H), 4.0 (s,3H),1.9(m,2H),1.06(t,3H)].

Reference Example 2

A stirred saturated aqueous solution of potassium permanganate (100 mL) is treated with 3-cyclopentyloxy-4-methoxybenzaldehyde (7.4 g; that is prepared as described hereinbefore in Reference Example 1) and sodium carbonate (3.4 g) and the mixture is stirred at 50° C. for 1 hour, and then cooled to room temperature. The reaction mixture is acidified by treatment with concentrated hydrochloric acid and then it is treated with aqueous sodium bisulfite solution until a colorless solution is obtained. The reaction mixture is extracted with dichloromethane (2×100 mL) and the organic extracts are dried over magnesium sulfate and concentrated. The resulting residue is recrystallized from diethyl ether, to give 3-cyclopentyloxy-4-methoxybenzoic acid (4.78 g) in the form of white crystals. [NMR(CDCl$_3$): 1.7(s,2H), 1.8–2.2 (m,6H),3.95(s,3H),4.85(s,1H),6.9(bs,1H) 7.6(bs, 1H), 7.8(s,1H),9.8(s,1H); Elemental analysis: C,65.6; H,6.8%; Calculated: C,66.1; H,6.8%].

By proceeding in a similar manner, but using the appropriate quantities of the corresponding benzaldehyde derivatives, prepared as described hereinbefore in Reference Example 1, there are prepared:

3-cyclohexyloxy-4-methoxybenzoic acid in the form of a white solid, m.p. 158–160° C. [NMR(CDCl$_3$): 1.2–2.1 (m,10H),3.94(s,3H), 4.3(m,1H),6.9(d,1H), 7.6(s,1H), 7.76 (d,1H)];

3-butoxy-4-methoxybenzoic acid in the form of a white solid, m.p. 130–1 32° C. [NMR(CDCl$_3$): 1.0 (t,3H), 1.5 (m,2H), 1.85(m,2H),3.95(s,3H),4.1(t,2H),6.92(d,2H), 7.6(s,1H),7.75(d,1H)]; and 3-propoxy-4-methoxybenzoic acid [(NMR(CDCl$_3$): 7.76 (dd,1H),7.6(d,1H),6.9(d,1H),4.04(t,2H), 3.94(s,3H), 1.9 (m,2H), 1.05(t,3H)].

Reference Example 3

Stirring thionyl chloride (20 mL) is treated portionwise with 3-cyclopentyloxy-4-methoxybenzoic acid (5.0 g; that is prepared as described hereinbefore in Reference Example 2) and the solution is then heated at 85° C. for 3 hours. Toluene (50 mL) is added and the mixture is concentrated to give 3-cyclopentyloxy-4-methoxybenzoyl chloride (4.12 g) in the form of an oil which slowly crystallized. [NMR(CDCl$_3$):

1.6–1.7 (m,2H),1.8–1.95(m,4H),1.94–2.05(m,2H),3.94(s, 3H),4.85 (m,1H), 6.9(d,1H),7.55(d,1H),7.8(q,1H); Elemental analysis: C,61.3; H,5.94; Cl,13.9%; Calculated: C,61.3; H,5.94; Cl,13.92%].

By proceeding in a similar manner, but using the appropriate quantities of the corresponding benzoic acid derivatives, that are prepared as described hereinbefore in Reference Example 2, there are prepared:

3-cyclohexyloxy-4-methoxybenzoyl chloride in the form of a colorless solid;

3-butoxy-4-methoxybenzoyl chloride in the form of a light brown oil; and 3-propoxy-4-methoxybenzoyl chloride [(NMR(CDCl$_3$): 7.82 (dd,1H),7.53(d,1H), 6.92(d,1H),4.03(t,2H),3.96(s, 3H),1.89 (m,2H), 1.06(t,3H)].

Reference Example 4

A stirred solution of 4-aminopyridine (40 g) in concentrated hydrochloric acid (500 mL) at 80° C. is treated dropwise with aqueous hydrogen peroxide solution (200 mL; 15% w/w), while keeping the temperature between 80° C. and 85° C. The solution is then cooled and basified by dropwise treatment with aqueous sodium hydroxide solution (50% w/w), while keeping the temperature below 15° C. The resulting white flocculent precipitate is recrystallized from toluene, to give 4-amino-3,5-dichloropyridine (61.5 g), m.p. 161.5–162.5° C.

Reference Example 5

A solution of 4-aminopyridine (47 g) in concentrated hydrochloric acid (355 mL) is treated portionwise at 80° C. with an aqueous solution of sodium hypochlorite (550 mL; 15% w/v). The mixture is cooled to 30° C. and basified by treatment with aqueous sodium hydroxide solution (300 mL; 35% w/v) during 20 minutes. The mixture is stirred and cooled for a further 30 minutes and then it is filtered. The solid is washed well with water and dried at 60° C. to give 4-amino-3,5-dichloropyridine (69.5 g).

Reference Example 6

A solution of 3-cyclopentyloxy-4-methoxybenzaidehyde (66 g) and sulfamic acid (39.6 g) in glacial acetic acid (500 mL) is treated dropwise during 1 hour with a solution of sodium chlorite (35 g) in water (150 mL). The mixture is stirred at 20° C. during 1 hour and then it is treated with water (500 mL) dropwise during 30 minutes. The resulting solid is filtered, washed with water and dried, to give 3-cyclopentyloxy-4-methoxybenzoic acid (60.9 g) in the form of white crystals [Elemental analysis: C,65.8; H,6.7%; calculated: C,66.1; H,6.8%].

Reference Example 7

A solution of triphenylphosphine (17.5 g) in dry tetrahydrofuran (50 mL) under nitrogen is treated with a solution of diisopropyl azodicarboxylate (13.5 g) in dry tetrahydrofuran (50 mL). The solution is stirred is treated with a solution of endo-8,9,10-trinorbomeol (5.0 g) in dry tetrahydrofuran (50 mL) followed by a solution of 3-hydroxy-4-methoxybenzaldehyde (10.2 g) in dry tetrahydrofuran (50 mL). The solution is heated at reflux for 15 hours, cooled, poured into water (600 mL), and extracted with diethyl ether (300 mL). The extract is washed with water (100 mL), with aqueous sodium hydroxide solution (2×100 mL; 1 M) and with water (2×100 mL), dried over magnesium sulfate and evaporated, to give an oil, which is subjected to flash chromatography on silica gel, eluting with a mixture of pentane and ethyl acetate (95:5 v/v) to give 3-(exo-8,9,10-trinorbornyl-2-oxy)-4-methoxybenzaldehyde (8.2 g), m.p. 56–61° C.

Reference Example 8

A stirred suspension of 3-hydroxy-4-methoxybenzaldehyde (50 g) in water (200 mL) at between 0 and 5° C. is treated dropwise with an aqueous solution of sodium hydroxide (200 mL; 20% w/v), followed at between 0 and 5° C. by benzoyl chloride (38 mL). The reaction mixture is stirred at between 0 and 5° C. for 1 hour and then it is allowed to warm to room temperature and is stirred for a further period of 2 hours. The resulting solution is extracted with dichloromethane (2×200 mL) and the combined extract is washed with water (200 mL), dried over magnesium sulfate and concentrated, to give 2-methoxy-5-formylphenyl benzoate (35.2 g), m.p. 70–72° C.

Reference Example 9

A stirred solution of potassium permanganate (28 g) in acetone (200 mL) is treated with 2-methoxy-5-formylphenyl benzoate (35.2 g; that is prepared as described in Reference Example 8), and the resulting vigorously reacting mixture is cooled in an ice bath. It is then stirred at room temperature for 3 hours. The mixture is then concentrated and the residue is treated with saturated aqueous sodium metabisulfite solution (300 mL). The resulting white solid is filtered off, washed well with water (200 mL), and dried, to give 3-benzoyloxy-4-methoxy-benzoic acid (29.3 g), m.p. 180–183° C.

Reference Example 10

A solution of 3-benzoyloxy-4-methoxybenzoic acid (29.3 g; that is prepared as described in Reference Example 9) in toluene (300 mL) is treated with thionyl chloride (30 mL) and heated on the steam bath for 6 hours. It is then cooled, filtered and concentrated, to give 3-benzoyloxy-4-methoxybenzoyl chloride (28.7 g), m.p. 120–122° C.

Reference Example 11

By proceeding in a manner similar to that described in Example 8, but using 3-benzoyloxy-4-methoxybenzoyl chloride (that is prepared as described in Reference Example 10) and 4-amino-3,5-dichloropyridine (that is prepared as described in Reference Example 4) as starting materials, there is prepared N-(3,5-dichloropyrid-4-yl)-3-benzoyloxy-4-methoxybenzamide, m.p. 191–192° C.

Reference Example 12

A solution of N-(3,5-dichloropyrid-4-yl)-3-benzoyloxy-4-methoxybenzamide (13.4 g; that is prepared as described in Reference Example 11) in methanol (160 mL) and water (60 mL) is treated with anhydrous potassium carbonate (18 g), and stirred overnight at room temperature. It is then brought to pH 7 by treatment with dilute hydrochloric acid (2 N), and concentrated. The residue is treated with water (100 mL) and filtered, and the resulting solid is dried, to give N-(3,5-dichloropyrid-4-yl)-3-hydroxy-4-methoxybenzamide (8.8 g), m.p. 227–228° C.

Reference Example 13

By proceeding in a manner similar to that described in Reference Example 2, but using the appropriate quantities of 3-(exo-8,9,10-trinorbornyl-2-oxy)-4-methoxybenzaldehyde (that is prepared as described in Reference Example 7) and (R)-3-(exo-8,9,10-trinorbornyl-2-oxy)-4-methoxybenzaldehyde and (S)-3-(exo-8,9,10-trinorbornyl-2-oxy)-4-methoxybenzaldehyde [that are similarly prepared from (R)-endo-8,9,10-trinorborneol and (S)-endo-8,9,10-trinorborneol or as described in the specification of European Patent Publication No. 0428302A2] there are prepared:

- 3-(exo)-8,9.10-trinorbornyl-2-oxy-4-methoxybenzoic acid, m.p. 155–156° C.;
- (R)-3-(exo)-8,9,10-trinorbornyl-2-oxy-4-methoxybenzoic acid, m.p. 155–156° C.; and
- (S)-3-(exo)-8,9,10-trinorbornyl-2-oxy-4-methoxybenzoic acid, m.p. 155–156° C.

Reference Example 14

By proceeding in a manner similar to that described in Reference Example 3, but using the appropriate quantities of the corresponding benzoic acid derivatives (that are prepared as described hereinbefore in Reference Example 13) there are prepared:

- 3-(exo)-8,9,10-trinorboryl-2-oxy-4-methoxybenzoyl chloride;
- (R)-3-(exo)-8,9,10-trinorbornyl-2-oxy-4-methoxybenzoyl chloride; and
- (S)-3-(exo)-8,9,10-trinorbornyl-2-oxy-4-methoxybenzoyl chloride; each in the form of oils.

Reference Example 15

A solution of methyl 4-chloro-3-nitrobenzoate (28 g) in acetone (250 mL) is treated portionwise with sodium thiomethoxide (10 g) and the mixture is stirred overnight at room temperature. After filtration, the solution is concentrated and water (300 mL) is added to the residue. The yellow solid is filtered off and subjected to flash chromatography eluting with a mixture of diethyl ether and pentane (1:4 v/v), to give methyl 4-methylthio-3-nitrobenzoate (18.5 g), in the form of a yellow solid, m.p. 118–120° C.

Reference Example 16

A stirred solution of methyl 4-methylthio-3-nitrobenzoate (6.82 g) in methanol (350 mL) is hydrogenated using a 5% w/w palladium on charcoal catalyst (0.8 g) at room temperature for 48 hours. After filtration the solution is concentrated, to give methyl 3-amino-4-(methylthio)benzoate (3.5 g), in the form of a pale yellow solid m.p. 63–65° C.

Reference Example 17

A stirred solution of concentrated hydrochloric acid (3.2 mL) in water (3.6 mL) at from 0° C. to 5° C. is treated with methyl 3-amino-4-(methylthio)benzoate (1.97 g), followed by a solution of sodium nitrite (0.82 g) in water (2 mL), at such a rate that the temperature remained from 0° C. to 5° C. The mixture is then allowed to warm to room temperature and it is stirred for a further period of 1 hour. The reaction mixture is treated with water (30 mL) and then heated to 55–60° C., until the evolution of nitrogen ceased (4 hours). The mixture is extracted with dichloromethane (2×100 mL) and the combined organic extracts are dried and concentrated. The resulting brown oil is subjected to flash chromatography, eluting with a mixture of diethyl ether and pentane (1:4 v/v), to give methyl 3-hydroxy-4-(methylthio)benzoate (0.6 g) in the form of a yellow solid.

Reference Example 18

A stirred solution of methyl 3-hydroxy-4(methylthio)benzoate (1.98 g) in dry dimethylformamide (40 mL) is treated with sodium hydride (0.44 g; 60% dispersion in mineral oil; 11 mmol) and the solution is stirred for a further 25 minutes. The reaction mixture is treated with cyclopentyl bromide (1.64 g), stirred at 60° C. for 3 hours. and then concentrated. The resulting residue is partitioned between dichloromethane (50 mL) and water (50 mL), the aqueous layer is extracted with dichloromethane (50 mL), and the combined organic layers are dried and concentrated, to give a red oil. The oil is subjected to flash chromatography, eluting with a mixture of diethyl ether and pentane (1:9 v/v), to give methyl 3-cyclopentyloxy-4-(methylthio)benzoate (1.9 g), m.p. 53–55° C.

Reference Example 19

A suspension of methyl 3-cyclopentyloxy-4-(methylthio)benzoate (0.8 g) in methanol (10 mL) and water (5 mL) is treated with potassium carbonate (0.48 g) and the mixture is heated at reflux for 7 hours. The mixture is concentrated, and the resulting residue is partitioned between diethyl ether (20 mL) and water (20 mL). The aqueous layer is separated, acidified to pH 1 by treatment with dilute hydrochloric acid (2 N), and extracted with dichloromethane (2×25 mL). The combined organic extracts are dried and concentrated, to give 3-cyclopentyloxy-4-(methylthio)benzoic acid (0.7 g) in the form of a white solid m.p. 150–152° C.

Reference Example 20

3-Cyclopentyloxy-4-(methylthio)benzoic acid (0.7 g) is dissolved in toluene (20 mL) and heated at 80° C. for 1 hour 30 minutes in the presence of thionyl chloride (5 mL). The reaction mixture is concentrated to give 3-cyclopentyloxy-4-(methylthio)benzoyl chloride (0.76 g), in the form of a yellow oil.

Reference Example 21

A cold (0° C.) solution of diisopropyl azodicarboxylate (5.1 g) in dry tetrahydrofuran (10 mL) is treated with a solution of triphenylphosphine (6.6 g) in dry tetrahydrofuran (10 mL). The resulting creamy precipitate is stirred in the cold for a further 0.5 hours, and treated with a solution of endo-8,9,10-trinorborneol (1.4 g) in dry tetrahydrofuran (10 mL), followed by a solution of methyl 3-hydroxy-4-(methylthio)benzoate (5.0 g) in dry tetrahydrofuran (10 mL) (that is prepared as described in Reference Example 17). The resulting mixture is then heated at reflux for 17 hours, cooled, poured into water (300 mL) and extracted with diethylether (2×250 mL). The combined ethereal extracts are dried over sodium sulfate and evaporated under reduced pressure to give an oil, which is subjected to flash chromatography on silica gel with dichloromethane/pentane (gradient elution 1:4 v/v to 3:1 v/v) to give methyl 3-(exo)-8,9,10-trinorbornyl-2-oxy-4-(methylthio)benzoate (3.0 g) as a colorless oil.

By proceeding in a similar manner, but replacing endo-8,9,10-trinorborneol used as starting material by the appropriate quantities of (R)-endo-8,9,10-trinorborneol and (S)-endo-8,9,10-trinorborneol [that are prepared as described in European Patent Publication No. 0 428 302 A2] there are prepared:

(R) methyl 3-(exo)-8,9,10-trinorbornyl-2-oxy-4-(methylthio)benzoate, m.p. 63–64° C. (from heptane), $[a]_D^{22}$ −12.9° (c=0.72, $CH_2Cl_2$); and (S) methyl 3-(exo)-8,9,10-trinorbornyl-2-oxy-4-(methylthio)benzoate, m.p. 65–66° C. (from heptane), $[a]_D^{22}$ +31.5° (c=1.20, CH$_2$Cl$_2$).

Reference Example 22

By proceeding in a manner similar to that described in Reference Example 19, but using the appropriate quantities of methyl 3-(exo)-8,9,10, trinorbornyl-2-oxy-4-(methylthio)benzoate, (R) methyl 3-(exo)-8,9,10-trinorbornyl-2-oxy-4-(methylthio)benzoate and (S) methyl 3-(exo)-8,9,10-trinorbornyl-2-oxy-4-(methylthio)benzoate (that are prepared as described in Reference Example 21) there are prepared:

3-(exo)-8,9,10-trinorbornyl-2-oxy-4-(methylthio)benzoic acid;

(R)-(exo)-8,9,10-trinorbornyl-2-oxy-4-(methylthio)benzoic acid, m.p. 151–152° C. (from heptane/toluene), $[a]_D^{22}$ +10.9° (c=0.92, CH$_2$Cl$_2$); and (S)-(exo)-8,9,10-trinorbornyl-2-oxy-4-(methylthio)benzoic acid, m.p. 167–168° C. (from heptane/toluene), $[a]_D^{20}$ +23.8° (c=1.48, CH$_2$Cl$_2$).

Reference Example 23

To 3-(exo)-8,9,10-trinorbornyl-2-oxy-4-(methylthio)benzoic acid (2.7 g), that is prepared as in Reference Example 22) in dry dichloromethane (30 mL) is added oxalyl chloride (1.3 mL). The resulting mixture is stirred at room temperature for 2 hours and then concentrated to give 3-(exo)-8,9,10-trinorbornyl-2-oxy-4-(methylthio)benzoyl chloride as an off yellow oil (2.8 g).

By proceeding in a similar manner but replacing 3-(exo)-8,9,10-trinorbornyl-2-oxy-4-(methylthio)benzoic acid used as starting material by the appropriate quantities of (R) 3-(exo)-8,9,10-trinorbornyl-2-oxy-4-(methylthio)benzoic acid and (S) 3-(exo)-8,9,10-trinorbornyl-2-oxy-4-(methylthio)benzoic acid (that are prepared as described in Reference Example 22) there are prepared:

(R)-3-(exo)-8,9,10-trinorbornyl-2-oxy-4-(methylthio)benzoyl chloride; and (S)-3-(exo)-8,9,10-trinorbornyl-2-oxy-4-(methylthio)benzoyl chloride.

Reference Example 24

Concentrated sulfuric acid (27 6 g) is slowly added to a stirred suspension of 3-hydroxy-4-nitrobenzoic acid (54.9 g, 0.3 mol) in methanol (135 mL) at ambient temperature. The resulting yellow slurry is stirred at reflux giving a complete solution after 30 minutes and the stirring at reflux is continued for 3 hours. The mixture is allowed to cool then diluted with water (600 mL) and the resulting mixture is then extracted with toluene (2×250 mL). The combined organic extract is washed with saturated aqueous sodium hydrogen carbonate solution (1×300 mL) and then dried (MgSO$_4$). The solvent is then removed under reduced pressure to give a yellow solid residue (54.9 g, 92.8%) which is identified as methyl 3-hydroxy-4-nitrobenzoate m.p. 92–94° C. [Elemental analysis: C,49.1; H,3.57; N,7.3%; calculated: C,48.74; H,3.58; N,7.1%].

Reference Example 25

Cyclopentyl bromide (20 g, 134 mmol) is added slowly (over 30 minutes) to a stirred suspension of potassium carbonate (27.6 g, 200 mmol) in N,N'-dimethylimidazolidinone (75 mL) containing 3-hydroxy-4-nitrobenzoic acid (9.15 g, 50 mmol) at 85° C. and then stirring is continued for 14 hours. The mixture is allowed to cool and then filtered. The filtrate is diluted with water (100 mL) then extracted with toluene (2×100 mL). The combined organic extract is dried over magnesium sulfate and then the solvent is removed under reduced pressure to give a brown mobile oil. This oil is subjected by flash chromatography on silica gel (dichloromethane as eluent) and the eluent evaporated under reduced pressure to give cyclopentyl 3-cyclopentyloxy-4-nitrobenzoate (10.2 g, 81.6%) as a yellow solid m.p. 45.5–46.5° C. [Elemental analysis: C,63.7; H,6.66; N,4.37%; calculated: C,63.93; H,6.63; N, 4.39%].

Reference Example 26

Cyclopentyl bromide (38.7 g, 0.26 mol) is added slowly (over 1 hour) to a stirred suspension of potassium carbonate (41.4 g, 0.3 mol) in N,N-dimethylformamide (200 mL) containing methyl 3-hydroxy-4-nitrobenzoate (39.4 g, 0.2 mol) at 65° C. and then the stirring is continued for 4 hours. The mixture is allowed to cool and then filtered. The filtrate is diluted with water (700 mL) containing sodium chloride (50 g) and then extracted with toluene (3×200 mL). The combined organic extract is washed with 1N sodium hydroxide solution (1×200 mL) and then water (2×200 mL) and then evaporated under reduced pressure to give methyl 3-cyclopentyloxy-4-nitrobenzoate (54.2 g, 100%) as a pale green solid which is used without further purification.

Reference Example 27

Sodium thiomethoxide (8.05 g, 0.115 mol) is added portionwise to a stirred solution of methyl 3-cyclopentyloxy-4-nitrobenzoate (26.5 g, 0.1 mol) in N,N'-dimethylimidazolidinone (200 mL) at ambient temperature under an atmosphere of nitrogen and stirring continued for 4 hours. The mixture is then diluted with water (1200 mL) containing sodium chloride (200 g) and extracted with ethyl acetate (2×300 mL). The combined extract is washed with saturated brine (2×300 mL) and then evaporated under reduced pressure to give methyl 3-cyclopentyloxy-4-(methylthio)benzoate (24.4 g, 91.7%) as an orange brown solid which is used without further purification.

Reference Example 28

Sodium thiomethoxide (0.177 g, 2.5 mmol) is added portionwise to a stirred solution of cyclopentyl 3-cyclopentyloxy-4-nitrobenzoate (0.64 g, 2 mmol) in N,N'-dimethylimidazolidinone (10 mL) at ambient temperature under an atmosphere of nitrogen and stirring continued for 4 hours. The mixture is then diluted with water (100 mL) containing sodium chloride (15 g) and extracted with ethyl acetate (2×50 mL). The combined extract is washed with saturated brine (1×100 mL) and then dried over magnesium sulfate and evaporated under reduced pressure to give cyclopentyl 3-cyclopentyloxy-4-(methylthio)benzoate (0.52 g, 81%) as a brown viscous oil which is used without further purification.

Reference Example 29

Method 1

A solution of methyl 3-cyclopentyloxy-4-(methylthio)benzoate (24.3 g, 91.4 mmol) in water (200 mL) and ethanol (50 mL) containing sodium hydroxide (18.3 g, 460 mmol) is heated under reflux for 3 hours. The solution is then poured into water (750 mL) and 1N acetic acid is added dropwise with stirring to between pH 5–6. The solid which separates is collected by filtration, washed with water (4×100 mL) and dried giving 3-cyclopentyloxy-4-(methylthio)benzoic acid (21.1 g, 91.7%) as a cream solid m.p. 158–160° C. [Elemental analysis: C,61.5; H,6.31%; calculated: C,61.88; H,6 39%].

Method 2

A solution of cyclopentyl 3-cyclopentyloxy-4-(methylthio)benzoate (0.5 g, 1.5 mmol) in water (30 mL) and methanol (10 mL) containing sodium hydroxide (1 g, 25 mmol) is heated under reflux for 3 hours. The solution is then poured into water (60 mL) and acetic acid is added dropwise with stirring to between pH 5–6. The solid which separates is collected by filtration, washed with water (5×10 mL) and dried giving 3-cyclopentyloxy-4-(methylthio) benzoic acid (0.35 g, 88.6%) as a cream solid m.p. 158–160° C.

Reference Example 30

A solution of 3-hydroxy-4-methoxybenzaldehyde (14.20 g) in dry dimethylformamide (300 mL) is treated portionwise with sodium hydride (60% dispersion in oil; 3.70 g) at room temperature under nitrogen. 3-Chlorocyclo-pentene (9.6 mL) is added and the resulting mixture is stirred overnight. The solvent is then removed under reduced pressure and the residue is partitioned between water (500 mL) and dichloromethane (500 mL) and the aqueous layer is further extracted with dichloromethane (500 mL). The combined organic extracts are dried and evaporated under reduced pressure and the residue is subjected to flash chromatography on silica gel, eluting with a mixture of ethyl acetate and pentane (1:1 v/v), to give 3-cyclopent-2-enyloxy-4-methoxybenzaldehyde, in the form of a pale brown oil (11.2 g).

Reference Example 31

A solution of 3-cyclopent-2-enyloxy-4-methoxybenzaldehyde (7.70 g) in t-butanol (160 mL) and 2-methyl-2-butene (40 mL) is treated dropwise with an aqueous solution (150 mL) containing sodium chlorite (80% technical grade; 4.39 g) and sodium dihydrogen phosphate (38.49 g), and left to stand overnight. The resulting mixture is extracted with dichloromethane (2×250 mL), and the combined organic layers are dried over sodium sulfate, the solvent is removed under reduced pressure and the resulting residue is recrystallized from ethyl acetate, to give 3-cyclopent-2-enyloxy-4-methoxybenzoic acid (5.89 g), in the form of a colorless solid. m.p. 160–163° C. [Elemental analysis: C,66.4; H,6.0%; calculated: C,66.7; H,6.0%].

Reference Example 32

A solution of 3-cyclopent-2-enyloxy-4-methoxybenzoic acid (5.89 g) in dry dichloromethane (50 mL) under nitrogen at room temperature is treated with triethylamine (10.50 mL), followed by oxalyl chloride (2.40 mL). The resulting mixture is stirred for 2.5 hours, then most of the solvent is removed under reduced pressure, and the resulting residue is taken up in dry tetrahydrofuran (50 mL) and filtered through a pad of diatomaceous earth. The resulting solution, containing 3-cyclopent-2-enyloxy-4-methoxybenzoyl chloride, is used immediately without further purification.

Reference Example 33

A stirred suspension of sodium hydride (60% in oil, 0.88 g) in dry dimethylformamide (44 mL) under nitrogen at between 5–10° C. is treated with a solution of 3-hydroxy-4-methoxy benzaldehyde (3.35 g) in dry dimethylformamide (6.3 mL). The resulting mixture is allowed to warm to room temperature and stirred for 40 minutes before recooling to between 5–10° C. A solution of 4-(p-toluenesulfonoxy) cyclopentene (5.24 g) in dry dimethylformamide (12.6 mL) is added dropwise maintaining the temperature below 10° C. The resulting mixture is allowed to warm to room temperature, left to stand for 46 hours, and then poured into 5% aqueous potassium carbonate (305 mL). t-Butyl methyl ether is added (150 mL), and the layers are thoroughly stirred and separated. The aqueous layer is further extracted with t-butyl methyl ether (2×75 mL), the combined organic extracts are washed with water (3×30 mL) and dried over magnesium sulfate. The solvent is removed under reduced pressure and the resulting residue is subjected to flash chromatography on silica gel, eluting with mixtures of ethyl acetate and pentane (1:10 to 3:10), to give 3-cyclopent-3-enyloxy-4-methoxybenzaldehyde as a pale amber viscous oil that slowly crystallizes on standing (1.75 g). Recrystallization of a portion (0.5 g) from cyclohexane gives an analytically pure sample (0.4 g), m.p. 60–62° C. [Elemental analysis: C,71.8; H,6.5%; calculated: C,71.5; H,6.8%].

Reference Example 34

A stirred solution of 3-cyclopent-3-enyloxy-4-methoxybenzaldehyde (1.75 g) in t-butanol (36.5 mL) and 2-methyl-2-butene (9.0 mL) is treated dropwise with an aqueous solution (34 mL) containing sodium chlorite (80% technical grade; 1.0 g) and sodium dihydrogen phosphate (8.75 g). The resulting mixture is further stirred for 5 hours, the layers are separated and the aqueous layer is extracted with t-butyl methyl ether (3×30 mL). The combined organic layers are washed with water (2×15 mL), dried over sodium sulfate and the solvent removed under reduced pressure. The resulting residue is recrystallized from ethyl acetate to give 3-cyclopent-3-enyloxy-4-methoxybenzoic acid (1.31 g), in the form of a colorless solid, m.p. 171–173° C. [Elemental analysis: C,66.6; H,6.0%; calculated: C,66.7; H,6.0%].

Reference Example 35

A solution of 3-cyclopent-3-enyloxy-4-methoxybenzoic acid (1.33 g) in dry tetrahydrofuran (20 mL) under nitrogen at room temperature is treated with triethylamine (2.36 mL), followed by oxalyl chloride (0.70 mL). The resulting mixture is stirred for 1 hour and then filtered through a pad of diatomaceous earth. The solid collected is washed with dry tetrahydrofuran (10 mL). The resulting combined filtrates, containing 3-cyclopent-3-enyloxy-4-methoxybenzoyl chloride, is used immediately without further purification.

Reference Example 36

A stirred solution of sodium hydroxide (16.8 g) in water (32 mL) at 20° C. is treated with dimethyl sulfoxide (560 mL). It is then treated with 3,4-dihydroxy-benzaldehyde (56.9 g), portionwise during 5 minutes, while keeping the temperature at 20° C. It is then treated with benzyl bromide (49.7 mL), portionwise, at 20° C. The solution is then heated at 80° C. for 6 hours and then allowed to stand at room temperature overnight. After dilution with ice-water (2240 mL) the solution is extracted with diethyl ether (1×1000 mL, 2×250 mL). The combined ether extracts are washed with water, dried over magnesium sulfate and concentrated, to give an oily solid, which is recrystallized from a mixture of ethyl acetate and isopropanol, to give 4-benzyloxy-3-hydroxybenzaldehyde (60.9 g), in the form of pale yellow crystals, m.p. 118–120° C.

Reference Example 37

A stirred solution of 4-benzyloxy-3-hydroxybenzaldehyde (60.9 g; that is prepared as described in Reference Example 36) in dry dimethylformanide (270 mL) under nitrogen is treated portionwise with potassium carbonate (79.5 g). After stirring at room temperature for 45 minutes, it is treated with cyclopentyl bromide (34.3 mL), and the resulting suspension is heated at 60° C. for 8 hours. After cooling, the solution is evaporated to low bulk under reduced pressure, to give an oil. This oil is treated with water (250 mL) and diethyl ether (300 mL), and the aqueous layer is washed with further quantities of diethyl ether (2×50 mL). The combined ethereal extracts are washed with brine (1×50 mL) and with water (3×50 mL), dried over magnesium sulfate and evaporated. The resulting residue is crystallized from methanol, to give 4-benzyloxy-3-cyclopentyloxybenzaldehyde (79 g), m.p. 55–56° C. [Elemental analysis: C,77.1; H,6.9%; calculated: C,77.0; H,6.8%].

Reference Example 38

A rapidly stirred solution of 4-benzyloxy-3-cyclopentyloxybenzaldehyde (10.5 g; that is prepared as described in Reference Example 37) in glacial acetic acid (100 mL) is treated with sulfamic acid (4.85 g) and stirred at room temperature for 10 minutes. The solution is then cooled in an ice bath and treated with a solution of sodium chlorite (4.2 g) in water (100 mL) during 15 minutes at 13–15° C. During the addition a white precipitate forms and, because stirring becomes difficult, a further quantity of glacial acetic acid (60 mL) is added. After warming to room temperature, the solution is stirred for a further 6 hours and further quantities of sodium chlorite (1.6 g) and sulfamic acid (1.7 g) are added. The mixture is poured onto water and the resulting solid is filtered off and dried, to give 3-cyclopentyloxy-4-benzyloxybenzoic acid (10 g).

Reference Example 39

A solution of 3-cyclopentyloxy-4-benzyloxybenzoic acid (5.1 g; that is prepared as described in Reference Example 38) in methanol (150 mL) and concentrated sulfuric acid (1 mL) is heated at reflux for 6 hours, and then it is cooled and concentrated in vacuo. The resulting residue is treated with ethyl acetate (150 mL) and saturated aqueous sodium bicarbonate solution (50 mL). The organic layer is collected, dried and evaporated. The resulting oil is subjected to flash chromatography on silica gel, using a mixture of ethyl acetate and pentane (1:4 v/v) as eluent, to give methyl 3-cyclopentyloxy-4-benzyloxybenzoate (4.8 g), in the form of a white solid, m.p. 58–59° C.

Reference Example 40

A solution of methyl 3-cyclopentyloxy-4-benzyloxybenzoate (2.64 g; that is prepared as described in Reference Example 39) in methanol (120 mL) is treated with palladium on charcoal (5%,0.5 g) and ammonium formate (2.0 g) and heated at reflux for 45 minutes. The catalyst is filtered off through a pad of diatomaceous earth and washed with methanol. The filtrate and washings are evaporated under reduced pressure, and the resulting residue is subjected to flash chromatography on silica gel using a mixture of diethyl ether and pentane 1:1 v/v), to give methyl 3-cyclopentyloxy-4-hydroxybenzoate (1.8 g), in the form of a cream solid, m.p. 73–75° C.

Reference Example 41

A solution of methyl 3-cyclopentyloxy-4-hydroxybenzoate (0.7 g; that is prepared as described in Reference Example 40) in dimethylformamide (15 mL) is treated with potassium carbonate (0.28 g) and potassium iodide (0.2 g). Chlorodifluoromethane is then bubbled through the reaction mixture at a very slow rate and the reaction mixture is heated at 70–75° C. for 5 hours. The mixture is then treated with water (50 mL) and extracted with ethyl acetate (2×50 mL). The combined ethyl acetate extracts are dried over magnesium sulfate, evaporated under reduced pressure, and subjected to flash chromatography on silica gel using a mixture of diethyl ether and pentane (1:1 v/v), to give methyl 3-cyclopentyloxy-4-difluoromethoxybenzoate, in the form of a pale yellow oil (0.65 g).

Reference Example 42

A solution of methyl 3-cyclopentyloxy-4-difluoromethoxybenzoate (0.6 g; that is prepared as described in Reference Example 41) in methanol (10 mL) is treated with potassium carbonate (0.35 g) and water (4 mL), and then it is heated at reflux for 3 hours. Methanol is evaporated off under reduced pressure, and the residue is dissolved in water (40 mL). The solution is washed with diethyl ether (40 mL), acidified with concentrated hydrochloric acid, and extracted with ethyl acetate (3×40 mL). The combined ethyl acetate extracts are dried over magnesium sulfate and evaporated under reduced pressure, to give 3-cyclopentyloxy-4-difluoromethoxybenzoic acid (0.47 g), in the form of a white solid, m.p. 126–128° C.

Reference Example 43

A mixture of 3-cyclopentyloxy-4-difluoromethoxybenzoic acid (0.47 g; that is prepared as described in Reference Example 42) and thionyl chloride (4 mL) in toluene (10 mL) is heated at 80° C. for 2 hours, and then evaporated under reduced pressure, to give 3-cyclopentyloxy4-difluoromethoxybenzoyl chloride (0.48 g), in the form of a pale yellow low melting solid, which is used without further purification.

Reference Example 44

A stirred solution of chlorosulfonic acid (90 mL) at room temperature is treated with p-anisic acid (40 g), portionwise, during 30 minutes. When the addition is complete, the mixture is stirred at 90° C. for 75 minutes, then it is cooled and poured onto ice. The white precipitate is collected and dissolved in ethyl acetate (300 mL). The organic extract is washed with brine (2×250 mL) dried over magnesium sulfate, and concentrated, to give 3-chlorosulfonyl-4-methoxybenzoic acid (34 g), in the form of a white solid m.p. 168–170° C.

Reference Example 45

A stirred solution of 3-chlorosulfonyl-4-methoxybenzoic acid (58 g; that is prepared as described in Reference Example 44) in glacial acetic acid (250 mL) at 40° C. is treated during 15 minutes with a solution of stannous chloride (107 g) in concentrated hydrochloric acid. The mixture is heated at reflux for 2 hours and the hot mixture is then poured into water (2 L) with vigorous stirring. The resulting solid is filtered off and dried, to give crude 3-mercapto-4-methoxybenzoic acid (34 g).

Reference Example 46

A solution of 3-mercapto-4-methoxybenzoic acid (that is prepared as described in Reference Example 45 from 58 g of 3-chlorosulfonyl-4-methoxybenzoic acid) in dimethylformamide (400 mL) is treated with potassium carbonate (120 g) and cyclopentyl bromide (60 g). The solution is heated at 50° C. for 3 hours, and then it is cooled and poured into water (3 L) containing concentrated hydrochloric acid (250 mL). The resulting solid is filtered off and dried, to give 3-cyclopentylthio-4-methoxybenzoic acid (10.5 g), in the form of a white crude solid.

Reference Example 47

A solution of 3-cyclopentylthio-4-methoxybenzoic acid (9 g; that is prepared as described in Reference Example 46) in dry dichloromethane (90 mL) under nitrogen is treated with oxalyl chloride (6.2 mL). After stirring at room temperature for 2 hours, the mixture is evaporated and dried under high vacuum, to give 3-cyclopentylthio-4-methoxybenzoyl chloride.

Reference Example 48

A mixture of 3-chlorosulfonyl-4-methoxybenzoic acid (4.76 g; that is prepared as described in Reference Example 44) in dry toluene (500 mL) stirred at room temperature is treated with triphenylphosphine (19.9 g) in one portion. The mixture is stirred and heated at 80° C. overnight, and then it is cooled, and treated with water (25 mL) and dioxane (25 mL), and the resulting solution is heated on a steam bath for 1 hour. The reaction mixture is allowed to cool to room temperature, and the organic layer is collected and concentrated. The resulting residue is partitioned between ethyl acetate (200 mL) and aqueous sodium hydroxide solution (500 mL; 2 N). The aqueous layer is separated, acidified by treatment with concentrated hydrochloric acid, and extracted with ethyl acetate (100 mL). The extract is washed with water (100 mL), dried over magnesium sulfate and concentrated, to give 3-mercapto-4-methoxybenzoic acid in the form of a white solid (3.4 g), m.p. 208–210° C.

Reference Example 49

A stirred solution of 3-mercapto-4-methoxybenzoic acid (3.34 g; that is prepared as described in Reference Example 48) in tetrahydrofuran (80 mL) at room temperature under nitrogen is treated portionwise with sodium hydride (60% dispersion in oil; 1.58 g; 40 mmol). The mixture is cautiously warmed to 50° C., and vigorous effervescence ensues. After hydrogen evolution has ceased, the mixture is treated dropwise with 2-bromopropane (2.2 g) and the solution is stirred at 50° C. for 2 hours. Dimethylformamide (40 mL) is added and the reaction mixture is stirred for a further 1 hour at 50° C. The solution is concentrated and the residue is treated with water (100 mL). The resulting solution is acidified by treatment with concentrated hydrochloric acid, and extracted with ethyl acetate (2×100 mL). The combined organic extract is washed with water (100 mL), dried over magnesium sulfate and concentrated to give, after trituration with pentane, 3-isopropylthio- 4-methoxybenzoic acid (2.6 g), in the form of a pale cream solid, m.p. 159–161° C. [Elemental analysis: C,58.4; H,6.25%; calculated: C,58.3 8; H,6.2%].

Reference Example 50

A solution of 3-isopropylthio-4-methoxybenzoic acid (2.5 g; that is prepared as described in Reference Example 49) in toluene (25 mL) and dimethylformamide (0.2 mL) is treated with thionyl chloride (2.5 mL) and the solution is stirred at 60° C. for 3 hours. The solution is concentrated, treated with toluene (10 mL) and again evaporated to dryness, to give 3-isopropylthio-4-methoxybenzoyl chloride (2.7 g), in the form of a light brown oil.

Reference Example 51

A solution of methyl 4-chloro-3-nitrobenzoate (28 g) in acetone (250 mL) is treated portionwise with sodium thiomethoxide (10 g) and the mixture is stirred overnight at room temperature. After filtration, the solution is concentrated and water (300 mL) is added to the residue. The yellow solid is filtered off and subjected to flash chromatography eluting with a mixture of diethyl ether and pentane (1:4 v/v), to give methyl 4-methylthio-3-nitrobenzoate (18.5 g), in the form of a yellow solid, m.p. 118–120° C.

Reference Example 52

A stirred solution of methyl 4-methylthio-3-nitrobenzoate (6.82 g; that is prepared as described in Reference Example 51) in methanol (350 mL) is hydrogenated using a 5% w/w palladium on charcoal catalyst (0.8 g) at room temperature for 48 hours. After filtration the solution is concentrated, to give methyl 3-amino-4-(methylthio)benzoate (3.5 g), in the form of a pale yellow solid, m.p. 63–65° C.

Reference Example 53

A stirred solution of concentrated hydrochloric acid (3.2 mL) in water (3.6 mL) at from 0° C. to 5° C. is treated with methyl 3-amino-4-(methylthio)benzoate (1.97 g; that is prepared as described in Reference Example 52), followed by a solution of sodium nitrite (0.82 g) in water (2 mL), at such a rate that the temperature remains from 0° C. to 5° C. The mixture is then allowed to warm to room temperature and it is stirred for a further period of 1 hour. The reaction mixture is treated with water (30 mL) and then heated to 55–60° C., until the evolution of nitrogen ceased (4 hours). The mixture is extracted with dichloromethane (2×100 mL) and the combined organic extracts are dried and concentrated. The resulting brown oil is subjected to flash chroma-tography, eluting with a mixture of diethyl ether and pentane (1:4 v/v), to give methyl 3-hydroxy-4-(methylthio)benzoate (0.6 g) in the form of a yellow solid.

Reference Example 54

A stirred solution of methyl 3-hydroxy-4-(methylthio) benzoate (1.98 g; that is prepared as described in Reference Example 53) in dry dimethyl-formamide (40 mL) is treated with sodium hydride (0.44 g of a 60% dispersion in mineral oil; 11 mmol) and the solution is stirred for a further 25 minutes. The reaction mixture is treated with cyclopentyl bromide (1.64 g), stirred at 60° C. for 3 hours and then concentrated. The resulting residue is partitioned between dichloromethane (50 mL) and water (50 mL), the aqueous layer is extracted with dichloromethane (50 mL), and the combined organic layers are dried and concentrated, to give a red oil. The oil is subjected to flash chromatography, eluting with a mixture of diethyl ether and pentane (1:9 v/v), to give methyl 3-cyclopentyloxy-4-(methylthio)benzoate (1.9 g), m.p. 53–55° C.

Reference Example 55

A suspension of methyl 3-cyclopentyloxy-4-(methylthio) benzoate (0.8 g; that is prepared as described in Reference Example 54) in methanol (10 mL) and water (5 mL) is treated with potassium carbonate (0.48 g) and the mixture is heated at reflux for 7 hours. The mixture is concentrated, and the resulting residue is partitioned between diethyl ether (20 mL) and water (20 mL). The aqueous layer is separated, acidified to pH 1 by treatment with dilute hydrochloric acid (2 N), and extracted with dichloromethane (2×25 mL). The combined organic extracts are dried and concentrated, to give 3-cyclopentyloxy-4-(methylthio)benzoic acid (0.7 g) in the form of a white solid m.p. 150–152° C.

Reference Example 56

3-Cyclopentyloxy-4-(methylthio)benzoic acid (0.7 g; that is prepared as described in Reference Example 55) is dissolved in toluene (20 mL) and heated at 80° C. for 1 hour 30 minutes in the presence of thionyl chloride (5 mL). Concentration gave 3-cyclopentyloxy-4-(methylthio) benzoyl chloride (0.76 g), in the form of a yellow oil.

Reference Example 57

A solution of 4-amino-3,5-dichloropyridine (0.46 g; that is prepared as described in Reference Example 4) in dry dimethylformanide (20 mL) is treated with sodium hydride (0.23 g of a 60% dispersion in mineral oil; 2.8 mmol) and the mixture is stirred for 20 minutes. It is then treated with a solution of 3-cyclopentyl-oxy-4-(methylthio)benzoyl chloride (0.76 g; that is prepared as described in Reference Example 20) in dimethylformamide (10 mL) and stirred at 60° C. for 2 hours. The solution is then concentrated and the resulting residue is partitioned between water (30 mL) and ethyl acetate (50 mL). The aqueous layer is extracted with ethyl acetate (50 mL) and the combined organic layers are dried, concentrated, and subjected to flash chromatography on silica gel, eluting with a mixture of diethyl ether and pentane (1:1 v/v), to give N-(3,5-dichloropyrid-4-yl)-3-cyclopentyloxy-4-(methylthio)benzamide (0.7 g) in the form of a white crystalline solid, m.p. 157–59° C. [NMR (CDCl$_3$]: 8.57 (s,2H), 7.69 (bs,1H), (dd,1H,J=8 Hz,J=2 Hz), 7.43 (d,1H,J=2 Hz), 7.17 (d,1H,J=8 Hz), 4.95 (m,1H), 2.46 (s,3H), 1.98–1.6(m,8H); Elemental analysis: C,54.0; H,4.5; N,7.0; Cl,17.8%; calculated: C,54.4; H,4.6; N,7.05; Cl,17.85%].

Reference Example 58

A suspension of 2-methoxyphenylbenzoate (212.5 g) in glacial acetic acid (1 L) is treated dropwise during 1 hour with a solution of bromine (51.5 mL) in glacial acetic acid (150 mL). The mixture is stirred for a further 1 hour, then it is concentrated and the residue is dissolved in t-butyl methyl ether (1500 mL). The solution is washed with water (500 mL) and with saturated aqueous sodium bicarbonate solution. The solution is then dried, filtered and concentrated, to give 2-benzoyloxy-4-bromoanisole (205.8 g), in the form of a white solid, m.p. 73–75° C.

Reference Example 59

A solution of 2-benzoyloxy-4-bromoanisole (5 g) and sodium hydroxide (3 g) in water (5 mL) and ethanol (50 mL) is heated at reflux for 1 hour 30 minutes. It is then evaporated and the residue is triturated with water (20 mL) and concentrated hydrochloric acid (10 mL) and extracted with dichloromethane (150 mL). The organic solution is washed with saturated aqueous sodium bicarbonate solution (3×25 mL), dried, and concentrated, to give 5-bromo-2-methoxyphenol (3.25 g), in the form of a white crystalline solid, m.p. 67–68° C.

Reference Example 60

A stirred solution of 5-bromo-2-methoxyphenol (74 g) and anhydrous potassium carbonate (73.6 g) in dry dimethylformamide (500 mL) is treated with cyclopentyl bromide (80.5 g) and the solution is heated at 60° C. for 16 hours. It is then concentrated, and the resulting residue is triturated with water (250 mL), and extracted with dichloromethane (3×250 mL). The combined extracts are dried and evaporated, to give 3-cyclopentyloxy-4-methoxyphenyl bromide (95.5 g), in the form of a light brown oil.

Reference Example 61

A solution of butyl lithium in hexane (5.1 mL; 2.5 M) is treated with a solution of 3-cyclopentyloxy-4-methoxyphenyl bromide (3.45 g) in dry tetrahydrofuran (30 mL) at −70° C. and the solution is then stirred at −70° C. for 1 hour. It is then treated dropwise with 2,6-dichlorophenylacetaldehyde (2.4 g), while keeping the temperature below −60° C. When the addition is complete the temperature is allowed to rise to room temperature and the solution is stirred for a further 2 hours. The reaction mixture is treated with aqueous ammonium chloride solution (50 mL) and the solution is extracted with diethyl ether (2×200 mL). The combined extracts are dried and concentrated, to give a yellow oil, which is subjected to flash chromatography, eluting with a mixture of diethyl ether and pentane (1:8 v/v), to give 1-(3-cyclopentyloxy-4-methoxyphenyl)-2-(2,6-dichlorophenyl)ethanol (1.6 g), in the form of a white solid, m.p. 87–89° C.

Reference Example 62

A solution of diisopropylamine (10.5 mL) in dry tetrahydrofuran (150 mL) is cooled to −75° C. and treated with a solution of butyl lithium in hexane (30 mL; 2.5 M) during 10 minutes. After stirring for 1 hour at −75° C. the mixture is treated with a solution of 3,5-dichloropyridine (10.8 g) in dry tetrahydrofuran (55 mL) and stirred for a further 30 minutes. It is then treated with methyl iodide (4.7 mL) in dry tetrahydrofuran (10 mL) during 10 minutes, and the solution is allowed to rise gradually to room temperature. After stirring for 2 hours, the mixture is treated with saturated aqueous sodium bicarbonate solution (50 mL), followed by diethyl ether (100 mL). The organic layer is washed with brine, dried and evaporated. and the resulting residue is subjected to flash chromatography, to give 3,5-dichloro-4-methylpyridine (10.6 g), m.p. 46–47° C.

Reference Example 63

A stirred solution of diisopropylamine (9.75 mL) in dry tetrahydrofuran (200 mL) at −70° C. is treated dropwise with a solution of butyl lithium in hexane (27.2 mL; 2.5 M) and the solution is stirred for 30 minutes. It is then treated with a solution of 3,5-dichloro-4-methylpyridine (10.25 g) in dry tetrahydrofuran (60 mL) during 30 minutes. while keeping the temperature below −75° C., and the solution is then stirred for a further 30 minutes. It is then treated with 3-cyclopentyloxy-4-methoxybenzaldehyde (13.92 g) in dry tetrahydrofuran (60 mL) during 15 minutes, and stirred for a further 1 hour 30 minutes at −75° C. The solution is treated with aqueous ammonium chloride solution and extracted with ethyl acetate (3×100 mL). The organic layers are combined, washed with brine, dried and concentrated to low volume. The resulting precipitate is filtered off, to give 1-(3-cyclopentyloxy-4-methoxyphenyl)-2-(3 5-dichloropyrid-4-yl)ethanol (20.5 g), m.p. 124–125° C.

Reference Example 64

Oxalyl chloride (2 mL) is added to a stirred solution of 3-cyclopentyloxy-4-methoxybenzoic acid (2.36 g) in dry dichloromethane (50 mL) under a nitrogen atmosphere, and the mixture stirred for 3 hours. The reaction mixture is concentrated in vacuo and the residue dissolved in fresh dry dichloromethane (50 mL). N,O-dimethylhydroxylamine hydrochloride (1.12 g) and 2,4,6-collidine (2.9 mL) are added and the mixture stirred for 4 hours. The mixture is diluted with dichloromethane (100 mL) and washed with saturated aqueous sodium bicarbonate (2×30 mL), 2 M aqueous hydrochloric acid (2×30 mL) and water (20 mL). The dried (MgSO$_4$) solution is concentrated to an orange oil (3 g) which is purified by flash chromatography (gradient elution ethyl acetate/pentane (2:3 v/v) to ethyl acetate/pentane (2:1 v/v) on silica column) to give 3-cyclopentyloxy-4,N-dimethoxy-N-methylbenzamide (2.5 g) as a yellow syrup.

Reference Example 65

Hydroxylamine hydrochloride (3.82 g) is added to a solution of 3-cyclopentyloxy-4-methoxybenzaldehyde (11.0 g) in acetic anhydride (30 mL) and the suspension heated in an oil bath at 100° C. until refluxing starts. The heating is then removed while the exothermic reaction refluxes gently. Heating at 100° C. is then continued for a further 1 hour. The dark solution is concentrated and the crude product dissolved in cyclohexane (200 mL). The solution is washed with 5% sodium bicarbonate solution (2×50 mL), water (2×50 mL) and brine (50 mL), and dried over magnesium sulfate. Upon evaporation, an amber oil (11.8 g) that is purified by flash chromatography (dichloromethane as eluant on silica column) gives 3-cyclopentyloxy-4-methoxybenzonitrile (8.6 g) as a pale yellow oil. [Elemental analysis: C,71.7; H,6.93; N,6.47%; calculated for $C_{13}H_{15}NO_2$: C,71.87; H,6.96; N,6.45%.].

Reference Example 66

A stirred solution of 5-amino-2-methoxyphenol (10 g) in dry dioxane (150 mL) is treated portionwise with an oil suspension of sodium hydride (60%; 3 g; 75 mmol) and the mixture is then warmed at 60° C. for 30 minutes. It is then treated dropwise with a solution of cyclopentyl bromide (9.2 mL) and potassium iodide (50 mg) in dry dimethylformamide (20 mL) and heated at reflux for 5 hours. The mixture is then concentrated and the residue is treated with ethyl acetate (200 mL) and water (200 mL). The organic layer is then separated, washed with water (100 mL), aqueous sodium hydroxide solution (250 mL; 1 N), and with water (100 mL), and dried over magnesium sulfate. The concentration of the reaction mixture gives a dark oil, which is subjected to flash chromatography, eluting with a mixture of n-hexane and ethyl acetate (1:1 v/v), to give 3-cyclopentyloxy-4-methoxyaniline (4.43 g), in the form of an oil.

Reference Example 67

A stirred solution of diisopropylamine (14 mL) in dry tetrahydrofuran (150 mL), is treated dropwise with a solution of butyl lithium in hexanes (40 mL; 2.5 M), under nitrogen, while keeping the temperature at below −70° C. The resulting mixture is then stirred for a further period of 30 minutes at below −70° C. The stirred mixture, while it is still maintained at below −70° C., is then treated dropwise with a solution of 4-picoline (9.3 g) in dry tetrahydrofuran (20 mL). The stirred mixture is maintained at below −70° C. for a further 45 minutes. The stirred mixture, while it is still maintained at below −70° C., is then treated with a solution of 3-cyclopentyloxy-4-methoxybenzaldehyde (22.0 g) in dry tetrahydrofuran (100 mL), and it is stirred at below −70° C. for a further 30 minutes. The resulting mixture is then allowed to warm to room temperature overnight, and then treated with saturated aqueous ammonium chloride solution (200 mL). The layers are separated and the aqueous layer is further extracted with ethyl acetate (3×300 mL). The combined organic extracts are dried over magnesium sulfate and evaporated to dryness. The resulting residue is recrystallized from ethyl acetate, to give (±)-1-(3-cyclopentyloxy-4-methoxyphenyl)-2-(pyrid-4-yl)ethanol (28.5 g), in the form of a cream solid, m.p. 102–103° C.

Reference Example 68

A stirred solution of concentrated hydrochloric acid (1.7 mL) in water (5 mL) from 0° C. and 5° C. is treated with 3-cyclopentyloxy-4-methoxyaniline (0.83 g), followed by a solution of sodium nitrite (0.29 g) in water (0.6 mL), at such a rate that the temperature remains from 0° C. and 5° C. The resulting solution is stirred for a further 10 minutes, while keeping the temperature below 5° C. The stirred solution, while still maintained at below 5° C., is then treated dropwise with a solution of sodium tetrafluoroborate (0.88 g) in water (1.8 mL). The resulting precipitate is filtered off, washed with cold water (3 mL) and dried in vacuo, to give 3-cyclopentyloxy-4-methoxyphenyldiazonium tetrafluoroborate (1.24 g) in the form of a gray solid, m.p. 120° C.

Reference Example 69

A stirred solution of 2-methoxyphenyl benzoate (10 g) in dichloromethane (100 mL) from 0–5° C. is treated dropwise with chlorosulfonic acid (2.9 mL) and the solution is then stirred for 3 hours from 0–5° C. The precipitate which forms is filtered off, washed with cold dichloromethane, and dried in vacuo, to give 3-benzoyloxy-4-methoxybenzenesulfonic acid (11.45 g), in the form of a white solid, m.p. 139–140° C.

Reference Example 70

A solution of 3-benzoyloxy-4-methoxybenzenesulfonic acid (7.69 g) in dry toluene (70 mL) is treated with thionyl chloride (9 mL), and the mixture is heated at reflux for 6 hours. Concentration gives 3-benzoyloxy-4-methoxybenzenesulfonyl chloride (8.4 g), in the form of a brown oil.

Reference Example 71

A stirred solution of 2-chloroaniline (3.3 g) and triethylamine (3.6 mL) in dichloromethane (50 mL) is treated, portionwise, with a solution of 3-benzoyloxy-4-methoxybenzenesulfonyl chloride (8.4 g) in dichloromethane (50 mL). The reaction mixture is stirred for 6 hours at room temperature, and then it is washed with water. The organic solution is dried and concentrated in vacuo, to give an oil, which is subjected to flash chromatography on silica gel, eluting with diethyl ether, to give a mixture of N-(3-benzoyloxy-4-methoxyphenylsulfonyl)-2-chloroaniline and N,N-bis(3-benzoyloxy-4-methoxyphenylsulfonyl)-2-chloroaniline.

Reference Example 72

A solution of potassium hydroxide (1.27 g) in water (5 mL) and methanol (10 mL) is treated with a mixture of N-(3-benzoyloxy-4-methoxyphenylsulfonyl)-2-chloroaniline and N,N-bis(3-benzoyloxy-4-methoxyphenylsulfonyl)-2-chloroaniline (2.39 g; that is prepared as described in Reference Example 71) and heated at reflux for 7 hours. After cooling, the solution is neutralized by treatment with dilute hydrochloric acid (1 N), and the mixture is extracted with dichloromethane (2×75 mL). The combined organic extracts are dried and concentrated, to give a waxy solid. This solid is subjected to flash chromatography on silica gel, eluting with diethyl ether, to give a mixture of N-(3-hydroxy-4-methoxyphenylsulfonyl)-2-chloroaniline and N,N-bis(3-hydroxy-4-methoxyphenylsulfonyl)-2-chloroaniline (0.7 g), which is used directly in Example 49.

Reference Example 73

Vigorously stirred aqueous ammonia solution (70 mL; 32% w/w) is treated dropwise with warm molten 3-cyclopentyloxy-4-methoxybenzoyl chloride (25.7 g) during a period of 20 minutes, keeping the temperature below 20° C. Stirring is continued at 20° C. for 2 hours, and then the suspension is filtered. The resulting solid is washed with water until free of ammonia, and is then dried under vacuum at 40–45° C., to give 3-cyclopentyloxy-4-methoxybenzamide (21.78 g), in the form of a buff solid.

Reference Example 74

A solution of 4-amino-2,3,5-trifluoropyridine [23.1 g; that is prepared as described in J.Med.Chem.30, 340–347, (1987)] and hydrazine hydrate (113 mL) in ethanol (925 mL) is stirred and heated at 100° C. for 2 days. The solution is then evaporated to low volume and the resulting 4-amino-3,5-difluoro-2-hydrazino-pyridine (22.5 g) is filtered off in the form of a cream solid.

This damp solid is added portionwise to a stirred solution of cupric sulfate (132 g) in water (462 mL) below 25° C., and the reaction mixture is stirred at room temperature for 48 hours. The reaction mixture is basified by treatment with aqueous potassium hydroxide solution (2 N) and extracted with dichloromethane (1500 mL). The organic layer is filtered through diatomaceous earth, dried over magnesium sulphate, and concentrated to give an off-white solid (13.72 g). This solid is subjected to mplc, using diethyl ether as eluent, to give 4-amino-3,5-difluoropyridine (3.4 g), m.p. 99–101° C. [NMR (CDCl3): 4.32(bs,2H),8.1(s,2H)].

Reference Example 75

By proceeding in a manner similar to that described in Reference Example 3, but using the appropriate quantities of the corresponding carboxylic acids, there are prepared:

3-cyclopentylmethoxy-4-methoxybenzoyl chloride, in the form of a light brown oil;

3-cyclopropylmethoxy-4-methoxybenzoyl chloride, in the form of a light brown oil;

3-isopropoxy-4-methoxybenzoyl chloride, in the form of a golden oil;

3-tert-butoxy-4-methoxybenzoyl chloride in the form of a light brown oil; and 4-methoxy-3-(pent-3-yloxy)benzoyl chloride, in the form of a golden oil.

Reference Example 76

By proceeding in a manner similar to that described in Reference Example 6, but using the appropriate quantities of the corresponding aldehydes, there are prepared:

3-cyclopentylmethoxy-4-methoxy-benzoic acid, in the form of a white solid, m.p. 148–152° C.;

3-cyclopropylmethoxy-4-methoxybenzoic acid, in the form of a white solid, m.p. 158–162° C.;

3-isopropoxy-4-methoxybenzoic acid, in the form of a white solid, m.p. 133–135° C.; and 4-methoxy-3-(pent-3-yloxy)benzoic acid, in the form of a white solid, m.p. 137–139° C. [Elemental analysis: C,65.9; H,7.7%; calculated: C,65.5; H,7.6%].

Reference Example 77

A solution of methyl 3-tert-butoxy-4-methoxy benzoate (4.93 g) in methanol (100 mL) is treated with a solution of potassium carbonate (3.5 g) in water (40 mL), and the solution is stirred for 4 hours at reflux. The solution is evaporated to low volume, the residue is dissolved in water (150 mL), washed with diethyl ether (100 mL) and brought to pH 4 by treatment with glacial acetic acid. The resulting mixture is extracted with ethyl acetate (2×100 mL). The combined organic extracts are washed with water (50 mL), dried over magnesium sulfate, and concentrated to give 3-tert-butoxy-4-methoxybenzoic acid (1.1 g) in the form of a white solid, m.p. 177–178° C. [NMR (CDCl3): 7.88(dd, 1H),7.76(d,1H), 6.94(d,1H),3.89(s,3H),1.39(s,9H)].

Reference Example 78

A stirred solution of 3-hydroxy-4-methoxy-benzaldehyde (5.74 g) in dry dimethylformamide (50 mL) is treated with cyclopentylmethyl bromide (7.34 g) and potassium carbonate (15 g), and the solution is heated at 60° C. for 24 hours. After cooling and filtration, the solution is evaporated to low bulk and dissolved in ethyl acetate (100 mL). The organic solution is washed with aqueous sodium hydroxide solution (4×50 mL; 2 N) and water (2×50 mL), dried over magnesium sulfate, and evaporated to give 3-cyclopentylmethoxy-4-methoxybenzaldehyde (6.5 g) in the form of a light brown oil.

By proceeding in a similar manner, but using the appropriate quantity of isopropyl bromide, there is prepared 3-isopropoxy-4-methoxybenzaldehyde, in the form of a light golden oil. [NMR (CDCl3): 9.85(s,1H), 7.46(dd,1H), 7.43 (d,1H), 6.98(d,1H), 4.65(m1H), 3.94(s,3H), 1.41(d,6H)].

Reference Example 79

By proceeding in a manner similar to that described in Reference Example 1, but using the appropriate quantity of cyclopropylmethyl bromide, there is prepared 3-cyclopropylmethoxy-4-methoxy-benzaldehyde, m.p. 55–58° C. [Elemental analysis: C,70.0; H,6.85%; calculated: C,69.9; H,6.8%].

By proceeding in a similar manner, but using the appropriate quantity of 3-bromopentane, there is prepared 4-methoxy-3-(pent-3-yloxy)benzaldehyde, in the form of a golden oil.

Reference Example 80

A stirred solution of isobutylene (33 mL) in dichloromethane (60 mL) at −70° C. is treated dropwise with a cooled solution of methyl 3-hydroxy-4-methoxybenzoate (6 g) in dichloromethane (60 mL), followed by trifluoromethanesulfonic acid (0.3 mL). The reaction mixture is vigorously stirred at −70° C. for 3 hours and then between −70° C. and −50° C. overnight. It is then treated with triethylamine (0.6 mL) and allowed to warm to room temperature. The resulting yellow solution is concentrated, and the residue is subjected by mplc, using diethyl ether as eluent, to give methyl 3-tert-butoxy-4-methoxybenzoate (4.93 g), m.p. 98–100° C. [Elemental analysis: C,65.7; H,7.8%; calculated: C,65.5; H,7.6%].

Reference Example 81

A solution of 3-[exobicyclo(2.2.1)hept-5-en-2-yloxy]-4-methoxy-benzaldehyde (8 g) and aqueous potassium hydroxide solution (1 mL; 50% w/v) in methanol (35 mL), is stirred vigorously on an oil bath at 50° C. The mixture is then treated, dropwise, with an aqueous solution of potassium hydroxide (8 mL; 50% w/v) in methanol (35 mL) with hydrogen peroxide (21 mL; 35% w/v), to give a slightly exothermic reaction. The solution is stirred for 2 hours at 50° C. and then is evaporated to low volume. The solution is diluted with water (100 mL), adjusted to pH 5 by treatment with concentrated hydrochloric acid and filtered to give 3-[exobicyclo(2.2.1)-hept-5-en-2-yloxy]-4-methoxybenzoic acid (6.42 g), m.p. 161–163° C. [NMR (CDCl$_3$): 1.31(d,1H);1.39(d,1H);1.57(ddd,1H); 1.65(d,1H);2.68(bs,1H); 2.83(bs,1H);3.67(s,3H);4.09(d,1H); 5.78(dd,1H);6.06(dd,1H);6.66 (d,1H); 7.30(s,1H);7.42(d,1H].

Reference Example 82

Thionyl chloride (4 mL) is added to a solution of 3-cyclopentyloxy-4-trifluoromethoxybenzoic acid (0.5 g) in dry toluene (10 mL) and the mixture is heated at 80° C. for 2 hours. Toluene is evaporated off under reduced pressure, to give 3-cyclopentyloxy-4-trifluoro-methoxybenzoyl chloride (0.54 g), in the form of a yellow oil, which was used without further purification.

Reference Example 83

Potassium carbonate (0.43 g) and water (2 mL) are added to a solution of methyl 3-cyclopentyloxy-4-trifluoromethoxybenzoate (0.78 g) in methanol (10 mL) and the mixture is heated under reflux for 2 hours. Methanol is evaporated off under reduced pressure, and the crude material is partitioned between water (75 mL) and ethyl acetate (75 mL). The organic layer is separated, and the aqueous layer is acidified with hydrochloric acid (2 N) and extracted with ethyl acetate (2×75 mL). The combined organic extracts are dried over magnesium sulfate and evaporated under reduced pressure, to give 3-cyclopentyloxy-4-trifluoromethoxybenzoic acid (0.53 g), in the form of a white solid, m.p. 116–118° C. [NMR (CDCl$_3$): 7.72(d,1H,J=2 Hz); 7.7(dd,1H,J=8 Hz, 2 Hz); 7.3(d,1H,J=8 Hz); 4.9(m,1H,);2.0–1.6(m,8H)].

Reference Example 84

Diisopropyl azodicarboxylate (0.61 mL) is added to a solution of methyl 3-hydroxy-4-trifluoromethoxybenzoate (0.74 g), cyclopentanol (0.19 g) and triphenylphosphine (0.81 g) in tetrahydrofuran (10 mL) and the mixture is heated overnight at reflux. Solvent is evaporated off under reduced pressure and the resulting yellow oil is triturated with diethyl ether. The white solid thus formed is filtered off, and the filtrate is evaporated under reduced pressure and subjected to mplc, to give methyl 3-cyclopentyloxy-4-trifluoromethoxy-benzoate in the form of a pale yellow oil (0.6 g).

Reference Example 85

Methyl 3-amino-4-trifluoromethoxybenzoate (2.3 g) is dissolved in a mixture of concentrated hydrochloric acid (5 mL) and water (10 mL), with slight warming. The solution is then cooled to −5° C. and a solution of sodium nitrite (0.8 g) in water (2 mL) is added dropwise at that temperature and the resulting yellow solution is stirred at 0° C. for 30 minutes. A small amount of undissolved solid material is filtered off, and a solution of sodium tetrafluoroborate (1.52 g) in water (2 mL) is added and the mixture is stirred at 0° C. for another 30 minutes. The white solid thus formed is filtered off, washed with water and diethyl ether, and dried over phosphorus pentoxide under vacuum (yield=2.25 g). A portion (0.5 g) of this solid is then added to a solution of cupric nitrate (150 g) in water (100 mL). The mixture is extracted with dichloromethane (2×100 mL), and the extracts are dried over magnesium sulfate and evaporated under reduced pressure, to give a pale yellow solid (1.4 g), which is subjected to mplc, eluting with a mixture of diethyl ether and pentane (1:4 v/v), to give methyl 3-hydroxy-4-trifluoromethoxybenzoate (1.0 g), in the form of a white solid, m.p. 95–97° C.

Reference Example 86

A solution of potassium carbonate (7.4 g) in water (72 mL) is added, dropwise, to a stirred solution of methyl 3-(tetrahydrothiophen-3-oxy)-4-methoxybenzoate (11.8 g) in methanol (200 mL) at room temperature. After the addition is complete, the solution is stirred and heated at 60–70° C. for 5 hours and allowed to stand at room temperature overnight. The solution is evaporated, the residue is dissolved in water, acidified with glacial acetic acid and the precipitate formed is collected and dried, to give 3-(tetrahydrothiophen-3-oxy)-4-methoxybenzoic acid (7.4 g). m.p. 177–179° C. [Elemental analysis: C,55.3; H,5.5; calculated: C,56.7; H,5.55%].

Reference Example 87

By proceeding as described in Reference Example 7, but using the appropriate quantities of 3-hydroxythiophane and isovanillic acid methyl ester, there was prepared methyl 3-(tetrahydrothiophen-3-oxy)-4-methoxy-benzoate, in the form of a golden oil. [Elemental analysis: C,55.2; H,6.8; S,8.1%; calculated: C,58.2; H,6.0; S,11.95%].

Reference Example 88

A solution of methyl 3-(4,4-difluoro-3-methylenecyclobut-1-enyloxy)-4-methoxybenzoate (1.39 g) in methanol (22 mL) is treated with a solution of potassium carbonate (0.83 g) in water (8 mL) and the solution is heated at 60–70° C. for 8 hours, cooled and evaporated. The residue is dissolved in water (30 mL), extracted with diethyl ether (50 mL) and acidified to pH 4 by treatment with glacial acetic acid. The precipitated solid is extracted with ethyl acetate (2×75 mL). The combined organic extracts are dried over magnesium sulfate and concentrated, to give 3-(4,4-difluoro-3-methylene-cyclobut-1-enyloxy)-4-methoxybenzoic acid, in the form of a white solid, m.p. 163–165° C.

Reference Example 89

A stirred solution of methyl 3-hydroxy-4-methoxybenzoate (1.72 g), potassium iodide (0.1 g), and potassium carbonate (1.55 g) in dimethylformamide (50 mL) is treated with 1-chloromethyl-2,2,3,3-tetrafluorocyclobutane (2.0 g), and the solution is stirred at 70–80° C. for 6 hours. After cooling, the reaction mixture is diluted with water (100 mL) and extracted with ethyl acetate (2×50 mL). The organic extracts are combined, dried over magnesium sulfate and concentrated, to give a golden oil.

The oil is subjected to flash chromatography, using diethyl ether as eluent, to give methyl 3-(4,4-difluoro-3-methylenecyclobut-1-enyloxy)-4-methoxybenzoate, m.p. 60–62° C. [Elemental analysis: C,59.5; H,4.3%; calculated: C,52.2; H,4.4%].

Reference Example 90

By proceeding in a similar manner to Reference Example 6, but using 3-(2-fluorocyclopentyloxy)-4-methoxybenzaldehyde as the starting material, there is prepared 3-(2-fluorocyclopentyloxy)-4-methoxybenzoic acid. Mass spectrum m/z 254($M^+$).

Reference Example 91

By proceeding in a similar manner to Reference Example 7, but using 2-transfluorocyclopentanol as the starting material, there is prepared 3-(2-fluorocyclopentyloxy)-4-methoxybenzaldehyde. Mass spectrum m/z 238($M^+$).

Reference Example 92

By proceeding in a manner similar to that described in Reference Example 20, but using as the starting material the appropriate quantity of 3-isopropoxy-4-(methylthio)benzoic acid, there is prepared 3-isopropoxy-4-(methylthio)benzoyl chloride, in the form of a yellow oil.

Reference Example 93

By proceeding in a manner similar to that described in Reference Example 19, but using as the starting material the appropriate quantity of methyl 3-isopropoxy-4-(methylthio) benzoate, there is prepared 3-isopropoxy-4-(methylthio) benzoic acid, in the form of a white solid, m.p. 127–129° C. [Elemental analysis: C,58.5; H,6.3; S,14.5%; calculated: C,58.4; H,6.2; S,14.2%].

Reference Example 94

A solution of methyl 3-isopropoxy-4-nitrobenzoate (5.7 g) in N,N'-dimethylimidazolidinone (35 mL) is treated with sodium thiomethoxide (2 g), and the mixture is stirred at room temperature for 4 hours. The mixture is then diluted with water (250 mL) containing sodium chloride (47 g), and is extracted with ethyl acetate (2×100 mL). The combined organic extracts are washed with brine (100 mL), dried over magnesium sulfate and evaporated in vacuo, to give a brown oil. The oil is subjected to flash chromatography, eluting with a 1.9 v/v mixture of diethyl ether and pentane, to give methyl 3-isopropoxy-4-(methylthio)benzoate (4.0 g), in the form of a cream solid, m.p. 41–43° C.

Reference Example 95

A solution of methyl 3-hydroxy-4-nitrobenzoate (5.9 g) in dimethylformamide (40 mL) is treated with potassium carbonate (6.2 g) and 2-bromopropane (3.7 g), and the stirred solution is heated at 60–65° C. for 4 hours. After cooling, water (100 mL) is added and the solution is extracted with toluene (2×100 mL). The combined organic extracts are dried over magnesium sulfate and evaporated in vacuo, to give methyl 3-isopropoxy-4-nitrobenzoate, in the form of a pale yellow solid (5.9 g), m.p. 46–48° C.

Reference Example 96

By proceeding in a manner similar to that described in Reference Example 63, but using as the starting material the appropriate quantity of (±)-3-[(exo)-8,9,10-trinorbornyl-2-oxy]-4-methoxybenzaldehyde, there is prepared, after flash chromatography, eluting with a mixture of ethyl acetate and pentane (1:2v/v), rac-1-[3-{(exo)-8,9,10-trinorbornyl-2-oxy}-4-methoxyphenyl]-2-(3,5-dichloropyrid-4-yl) ethanone, in the form of a yellow oil.

Reference Example 97

By proceeding in a manner similar to that described in Reference Example 63, but using as the starting material the appropriate quantity of 3-cyclopentyloxy-4-(methylthio) benzaldehyde, there is prepared 1-[3-cyclo-pentyloxy-4-(methylthiophenyl)-2-(3,5-dichloropyrid-4-yl)ethanol, in the form of a white solid, m.p. 122–123C. [Elemental analysis: C,57.3; H,5.3; Cl,17.6; N,3.4; S,8.4%; calculated: C,57.3; H,5.3; Cl,17.8; N,3.5; S,8.1%].

Reference Example 98

A solution of 4-bromo-2-cyclopentyloxy-1-(methylthio) benzene (13.2 g) in dry tetrahydrofuran (100 mL) under nitrogen is treated at –70° C. with a solution of butyllithium in hexane (20.24 mL; 2.5 M) and the resulting solution is stirred for 1 hour at this temperature. It is then treated with dimethylformamide (7.12 mL), followed by boron trifluoride diethyl etherate (11.32 mL), keeping the temperature at –65° C. When the addition is complete the reaction mixture is allowed to warm to room temperature and is then poured into ice-water (450 ml,) and extracted with dichloromethane (3×400 mL). The combined extracts are dried over magnesium sulfate and concentrated to give an oil, which is subjected to flash chromatography, eluting with a mixture of dichloromethane and cyclohexane (3:7 v/v), to give 3-cyclopentyloxy-4-(methylthio)-benzaldehyde (6.2 g). [NMR(DMSO): 9.91(S,1H),7.53(dd,1H),7.36(d,1H), 7.33 (d,1H),5.01 (m,1H),2.44(s,3H),2.0–1.5(m,8H)].

Reference Example 99

A stirred solution of 4-bromo-2-hydroxythioanisole (15.9 g) and cyclopentyl bromide (16.05 g) in dry dimethylformamide (170 mL) is treated with anhydrous potassium carbonate (14.7 g) and the mixture is heated at 60° C. for 1 day. After cooling, the solution is diluted with water (250 mL) and extracted with ethyl acetate (3×100 mL). The combined extracts are dried over magnesium sulfate and concentrated. The residue is subjected to flash chromatography, eluting with a mixture of ethyl acetate and pentane (5:95 v/v), to give 4-bromo-2-cyclopentyloxy-1-(methylthio)benzene, in the form of an oil (17.2 g). [NMR (DMSO): 7.14–7.03(m,3H),4.93(m,1H), 2.33(s,3H), 2.0–1.53(m,8H)].

Reference Example 100

By proceeding in a manner similar to that described in Reference Example 63, but using as the starting material the appropriate quantity of 4-methoxy-3-prop-2-yloxybenzaldehyde, there is prepared 1-(4-methoxy-3-prop-2-yloxyphenyl)-2-(3,5-dichloropyrid-4-yl)ethanol, in the form of a buff solid, m.p. 132–133° C. [Elemental analysis: C,57.2; H,5.37; Cl,19.8; N,3.80%; calculated: C,57.32; H,5.38; Cl,19.9; N,3.93%].

Reference Example 101

A mixture of 3-hydroxy-4-methoxybenzaldehyde (20.0 g), anhydrous potassium carbonate (26.2 g) and 2-bromopropane (18.3 mL) in dry dimethylformamide (300 mL) is stirred and heated at 55–65° C. for 24 hours. The cooled mixture is poured into water and extracted with ethyl acetate. The extract is dried over magnesium sulfate and concentrated in vacuo at 40° C., to give 4-methoxy-3-prop-2-yloxybenzaldehyde, in the form of an oil (24.2 g).

Reference Example 102

By proceeding in a manner similar to that described in Example 63, but using as the starting material the appropriate quantity of 4-methylthio-3-prop-2-yloxybenzaldehyde, there is prepared 1-(4-methylthio-3-prop-2-yloxyphenyl)-2-(3,5-dichloropyrid-4-yl)ethanol, in the form of a buff solid, m.p. 106–108° C. [Elemental analysis: C,55.1; H,5.23; N,3.73%; calculated: C,54.84; H,5.14; N,3.76%].

Reference Example 103

A solution of n-butyllithium in hexanes (14.82 mL; 2.5M) is added to a solution of 4-bromo-2-prop-2-yloxythioanisole (8.8 g) in dry tetrahydrofuran (70 mL), whilst cooling the mixture to −70° C. under nitrogen. The mixture is stirred for 1 hour at −70° C. Dry dimethylformamide (5.22 mL) and boron trifluoride diethyl etherate (8.29 mL) are added sequentially and the mixture is allowed to warm to room temperature. The mixture is poured into water and the product is extracted with dichloromethane. The extract is dried over magnesium sulfate and concentrated in vacuo, and the residue is subjected to flash chromatography on silica gel, eluting with a mixture of pentane and ethyl acetate (9:1 v/v) to give 4-methylthio-3-prop-2-yloxybenzaldehyde, in the form of a soft yellow solid, m.p. 50–54° C.

Reference Example 104

By proceeding in a manner similar to that described in Reference Example 99, but using as the starting material the appropriate quantity of 2-bromopropane, there is prepared 4-bromo-2-prop-2-yloxythioanisole, in the form of a colourless oil.

Reference Example 105

By proceeding in a manner similar to that described in Reference Example 63, but using as the starting material the appropriate quantity of 3-cyclopentyloxy-4-difluoromethoxybenzaldehyde, there is prepared 1-(3-cyclopentyloxy-4-difluoromethoxyphenyl)-2-(3,5-dichloropyrid-4-yl)ethanol, in the form of a pale yellow solid, m.p. 121–123° C. [Elemental analysis: C,55.2; H,4.6; N,3.3; Cl,16.7%; calculated: C,54.6; H,4.6; N,3.35; Cl,16.95%].

Reference Example 106

A solution of 3-cyclopentyloxy-4-hydroxybenzaldehyde (5.1 g) in dimethylformamide (50 mL) is treated with potassium carbonate (4.83 g) and potassium iodide (1.2 g) and the solution is heated at 70–75° C. whilst difluorochloromethane is bubbled though it at a slow rate, during 5 hours. Water (100 mL) is added and the mixture is extracted with ethyl acetate (2×100 mL). The combined organic extracts are dried over magnesium sulfate and concentrated to give a brown oil. The oil is subjected to flash chromatography, eluting with a mixture of diethyl ether and pentane (1:4 v/v), to give 3-cyclopentyloxy-4-difluoromethoxybenzaldehyde, in the form of a pale yellow oil (4.7 g). [NMR (CDCl$_3$): 9.92(s,1H);7.5–7.24(m,3H); 6.34–5.96(t,1H); 4.9(m,1H);2.0–1.6(m,8H)].

Reference Example 107

By proceeding in a manner similar to that described in Reference Example 63, but using as the starting material the appropriate quantity of 3-[exobicyclo(2.2.1)hept-5-en-2-yloxy]-4-methoxy-benzaldehyde, there is prepared 2-(3,5-dichloropyrid-4-yl)-1-[3-{exobicyclo(2.2.1)hept-5-en-2-yloxy}-4-methoxyphenyl]ethanol. [NMR (CDCl$_3$): 1.2–1.4 (m,1H); 1.45–1.6(m,1H); 1.65–1.8(m,1H); 1.9(m,1H); 2.1 (bs,1H); 2.9(bs,1H); 3.05(bd,J=14 Hz,1H); 3.25(dd,J=5 Hz,J=12 Hz,1H); 3.4–3.5(m,1H);3.84(s,3H); 4.28(bm,1H) ;5.05(m,1H); 6.02(m,1H); 6.3(m,1H);6.8–6.95(m,3H),8.42 (s,2H)].

Reference Example 108

By proceeding in a manner similar to that described in Example 63, but using as the starting material the appropriate quantity of 4-difluoromethoxy)-3-isopropoxybenzaldehyde there is prepared 2-(3,5-dichloro-4-pyridyl)-1-(4-difluoromethoxy-3-isopropoxyphenyl)ethanol, in the form of a white solid, m.p. 125–126° C. [Elemental analysis: C,52.3; H,4.4; N,3.5; Cl,18.1%; calculated: C,52.1; H,4.4; N,3.6; Cl,18.1%].

Reference Example 109

A cold (0° C.) solution of 4-hydroxymethyl-3,5-dichloropyridine (3.0 g) and N-bromosuccinimide (6.1 g) in dry dimethylformamide (100 mL) is treated with triphenylphosphine (8.9 g), portionwise, during 5 minutes. The resulting red solution is stirred at 0° C. for 45 minutes, and then treated with methanol (5 mL), followed by water (300 mL). The mixture is extracted with diethyl ether (4×200 mL), the combined organic washings dried over sodium sulfate, and the solvent removed under reduced pressure. The resulting residue is chromatographed on silica gel, eluting with a mixture of diethyl ether and pentane (1:2 v/v), to give 4-bromomethyl-3,5-dichloropyridine (3 g), in the form of an off-white solid, m.p. 40–44° C.

Reference Example 110

A cold (0° C.) solution of 4-formyl-3,5-dichloro-pyridine (3.0 g) in ethanol (50 mL) is treated with sodium borohydride (0.7 g), portionwise, during 5 minutes. The resulting mixture is stirred at 0° C. for 10 minutes, and then treated with aqueous hydrochloric acid (5 mL; 2 M), followed by basification to pH 7 by treatment with saturated aqueous sodium hydrogen carbonate solution. The mixture is diluted with water (500 mL) and extracted with ethyl acetate (4×150 mL). The combined organic washings are dried over magnesium sulfate, and the solvent removed under reduced pressure. The resulting residue is recrystallised from t-butyl methyl ether to give 4-hydroxymethyl-3,5-dichloropyridine (2.0 g), in the form of a white solid, m.p. 87–88° C.

Reference Example 111

By proceeding in a manner similar to that described in Reference Example 62, but using instead of methyl iodide the appropriate quantity of dimethylformamide, there is prepared 4-formyl-3,5-dichloropyridine, in the form of an off-white solid, m.p. 73–75° C.

The compounds of formula I exhibit useful pharmacological activity and accordingly are incorporated into pharmaceutical compositions and used in the treatment of patients suffering from certain medical disorders. More especially, they are cyclic AMP phosphodiesterase inhibitors, in particular type IV cyclic AMP phosphodiesterase inhibitors. The present invention provides compounds of formula I, and compositions containing compounds of formula I, which are of use in a method for the treatment of a patient suffering from, or subject to, conditions which can be ameliorated by the administration of an inhibitor of cyclic AMP phosphodiesterase. For example, compounds within the present invention are useful as bronchodilators and asthma-prophylactic agents and agents for the inhibition of eosinophil accumulation and of the function of eosinophils, e.g. for the treatment of inflammatory airways disease, especially reversible airway obstruction or asthma, and for the treatment of other diseases and conditions characterized by, or having an etiology involving, morbid eosinophil accumulation. As further examples of conditions which can be ameliorated by the administration of inhibitors of cyclic AMP phosphodiesterase such as compounds of formula I there may be mentioned inflammatory diseases, such as atopic dermatitis, urticaria, allergic rhinitis, psoriasis, rheumatic arthritis, ulcerative colitis, Crohn's disease, adult respiratory distress syndrome and diabetes insipidus, other proliferative skin diseases such as keratosis and various types of dermatitis, conditions associated with cerebral metabolic inhibition, such as cerebral senility, multi-infarct dementia, senile dementia (Alzheimer's disease), and memory impairment associated with Parkinson's disease, and conditions ameliorated by neuroprotectant activity, such as cardiac arrest, stroke, and intermittent claudication. A special embodiment of the therapeutic methods of the present invention is the treating of asthma.

The compounds are also inhibitors of tumor necrosis factor, especially a-TNF. Thus, the present invention provides compounds of formula I, and compositions containing compounds of formula I, which are of use in a method for treating a patient suffering from, or subject to, conditions which can be ameliorated by the administration of an inhibitor of a-TNF. For example compounds of the present invention are useful in joint inflammation, arthritis, rheumatoid arthritis and other arthritic conditions such as rheumatoid spondylitis and osteoarthritis. Additionally, the compounds are useful in treatment of sepsis, septic shock, gram negative sepsis, toxic shock syndrome, acute respiratory distress syndrome, asthma and other chronic pulmonary diseases, bone resorption diseases, reperfusion injury, graft vs. host reaction and allograft rejection. Furthermore, the compounds are useful in the treatment of infections such as viral infections and parasitic infections, for example malaria such as cerebral malaria, fever and myalgias due to infection, HIV, AIDS, cachexia such as cachexia secondary to AIDS or to cancer. Other disease states that may be treated with the compounds of the present invention include Crohn's disease, ulcerative colitis, pyresis, systemic lupus erythematosus, multiple sclerosis, type I diabetes mellitus, psoriasis, Beghet's disease, anaphylactoid purpura nephritis, chronic glomerulonephritis, inflammatory bowel disease and leukemia. A special embodiment of the therapeutic methods of the present invention is the treating of joint inflammation.

According to a further feature of the invention there is provided a method for the treatment of a human or animal patient suffering from, or subject to, conditions which can be ameliorated by the administration of an inhibitor of cyclic AMP phosphodiesterase or of TNF, especially a-TNF, for example conditions as hereinbefore described, which comprises the administration to the patient of an effective amount of compound of formula I or a composition containing a compound of formula I. "Effective amount" is meant to describe an amount of compound of the present invention effective in inhibiting cyclic AMP phosphodiesterase and/or TNF and thus producing the desired therapeutic effect.

The present invention also includes within its scope pharmaceutical formulations which comprise at least one of the compounds of formula I in association with a pharmaceutically acceptable carrier or coating.

In practice compounds of the present invention may generally be administered parenterally, rectally or orally, but they are preferably administered by inhalation.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

Compounds within the scope of the present invention exhibit marked pharmacological activities according to tests described in the literature which tests results are believed to correlate to pharmacological activity in humans and other mammals. The following pharmacological test results are typical characteristics of compounds of the present invention.

1. Inhibitory Effects of Compounds on PDE Activity.
1.1 Preparation of PDE Isozymes from Pig Aorta.

The method is described fully by Souness and Scott (*Biochem. J.*, 291, 389–395,1993). Briefly, aortas of freshly slaughtered pigs are placed in Hepes buffered krebs solution extraneous tissue on the outside of the aorta is trimmed off and the endothelial layer on the intimal surface is removed by rubbing with a cotton swab. Smooth muscle strips are plucked from the aorta and 25 g are homogenized using a Waring Blender in homogenization buffer (20 mM Tris/HCl, pH 7.5, 2 mM $MgCl_2$, 1 mM dithiothreitol, 5 mM EDTA and 1 mg/ml aprotinin). The homogenate is further homogenized with an Ultra-Turrax and then centrifuged (3000 g, 5 minutes). The supernatant is removed, and the pellet is sonicated in a small volume (25–50 mL) of homogenization buffer. The sonicate is centrifuged (3000 g, 5 minutes), the pellet discarded and the supernatant is pooled with that from the first centrifugation step. The pooled supernatants are centrifuged (100,000 g, 1 hour), the resulting high-speed supernatant is filtered (0.45 $\mu$m) and then applied to a DEAE-trisacryl (IBF) column (50×2.44 cm) preequilibrated in column buffer (20 mM Tris/HCl, pH 7.5, 2 mM $MgCl_2$, 1 mM dithiothreitol, 20 $\mu$M TLCK). The column is washed with 500–700 mL of column buffer and PDE activities are eluted with 2 successive linear gradients of NaCl (0–200 mM, 400 mL and 200–300 mM, 200 mL) in column buffer. The fractions in the separated peaks of activity corresponding to the different PDE isozymes are pooled and stored at −20° C. in 30% (v/v) ethylene glycol.

1.2 Measurement of PDE Activity.

PDE activity is determined by the two-step radioisotopic method of Thompson et al., *Adv. Cyclic Nucl. Res.*, 10, 69–92 (1979). The reaction mixture contains 20 mM Tris/HCl (pH 8.0), 10 mM $MgCl_2$, 4 mM 2-mercaptoethanol, 0.2 mM EGTA and 0.05 mg of BSA/mL. The concentration of substrate is 1 $\mu$M.

The $IC_{50}$ values for the compounds examined are determined from concentration-response curves in which concentrations range from 0.1 nM to 40 $\mu$M.

1.3 Results.

Compounds within the scope of the invention produce up to about 50% inhibition of porcine aortic cyclic AMP-specific phosphodiesterase (PDE IV) at concentrations from about $10^{-9}$ M up to about $10^{-5}$ M, preferably from about $10^{-9}$ up to about $10^{-8}$ M. The compounds of the invention are from about 10,000-fold to about 50-fold more selective for cyclic AMP phosphodiesterase IV than cyclic nucleotide phosphodiesterase types I, III or V.

2. Inhibitory Effects of Compounds on Eosinophil Superoxide Generation.
2.1 Preparation of Guinea-pig Eosinophils.

The Method is Described Fully in Souness et al (*Biochem. Pharmacol.* 42, 937–945, 1991).

2.2 Measurement of Superoxide Generation.

Superoxide anion generation is determined as the superoxide dismutase inhibitable reduction of p-iodonitrotetrazolium violet (INTV) (Souness et al, *Biochem. Pharmacol.* 42, 937–945, 1991). Briefly, cells are incubated in 96 well microtitre plates in 0.25 mL of Hanks buffered salt solution (HBSS) containing INTV (0.5 mg/mL) plus other additions for 45 minutes at 37° C. The cells are then centrifuged at 500 g for 5 minutes and the supernatant is aspirated. The pellet is solubilized by incubation overnight at room temperature in DMSO containing 0.6 M HCl and the absorbance of the reduced dye is measured at 492 nm. The results are expressed in absorbance units.

2.3 Results.

Compounds within the scope of the invention produce up to about 50% inhibition of superoxide generation from eosinophiis harvested from the peritoneal cavities of guinea-pigs at concentrations from about $10^{-8}$ M to about $10^{-5}$ M, preferably from about $10^{-8}$ M up to about $10^{-7}$ M.

3. Effects of Compounds on Tracheal Smooth Muscle Contractility.
3.1 Preparation of Guinea-pig Tracheal Strips and Contractility Studies.

Organ bath studies are performed essentially according to Tomkinson et al (*Br. J. Pharmacol.* 108 57–61, 1993). Briefly, tracheas are removed from male, Dunkin-Hartley guinea-pigs (400–500 g) are placed in Krebs Ringer Bicarbonate (KRB) solution and fat and connective tissue are dissected away. Epithelium is removed by mechanical abrasion and the tracheal strips are suspended under an applied load, such that they are at their optimal length, derived from preliminary experiments, and equilibrated for 90 minutes, washing at 15 minute intervals.

Cumulative concentration-response curves to spasmogens are constructed and the concentration producing 30% of maximum contraction ($EC_{30}$) is determined by computerized linear regression analysis. For relaxant studies, tissues are contracted with spasmogens (such as methacholine, histamine, leukotriene $D_4$) ($EC_{30}$) and when the response plateaus, PDE inhibitors (10 nM-100 $\mu$M) or vehicle control (DMSO) are added cumulatively. The concentration of relaxant producing 50% inhibition ($IC_{50}$) of the agonist response is calculated by linear regression. Alternatively, PDE inhibitors, as above, may be added to tissues under basal tone and the concentration producing 50% relaxation ($EC_{50}$) calculated as above.

3.2 Results.

Compounds within the scope of the invention produce about 50% relaxation of guinea-pig tracheal strips (under basal tone or which had been contracted by treatment with spasmogens) at concentrations from about $5\times10^{-9}$ M to about $10^{-5}$ M, preferably from about $5\times10^{-9}$ M to about $10^{-7}$ M.

4. In vivo Bronchodilator Actions of Compounds.

4.1 Measurement of Bronchodilatation.

Bronchorelaxant activity is measured in in vivo tests in the anaesthetized guinea-pig or rat according to the method described in Underwood et al., *Pulm. Pharmacol.* 5, 203–212, (1992) in which the effects on bronchospasm induced by histamine (or other spasmogens such as methacholine or leukotriene $D_4$) is determined. Nebulized aerosols generated from aqueous solutions of compounds of the invention are each administered for one minute to the anaesthetized animals. Alternatively, dry powder formulations made up from compounds of the invention and lactose are blown into the airways of the anaesthetized guinea-pigs or rats by the method described in Underwood et al., *J. Pharm. Methods*, 26 203–210, 1991.

4.2 Results.

Compounds within the scope of the invention produce from about 30% up to about 90% decrease in bronchospasm when administered at effective doses of about 4 to about 1000 μg/kg, preferably about 4 to about 50 μg/kg, without any significant effect on blood pressure.

5. In vivo Actions of Compounds on Antigen (ovalbamin)-induced Eosinophilia in Guinea-pigs.

5.1 Treatment of Animals and Measurement of Eosinophil Numbers.

Male Dunkin-Hartley guinea-pigs weighing 200–250 g are sensitized using 10 μg ovalbumin in 1 mL of a 100 mg/mL suspension of aluminium hydroxide, i.p.

Sensitized guinea-pigs are anaesthetised and dry powder formulations of PDE inhibitors or lactose are administered (i.t.) into the airways. In some cases PDE inhibitors are administered orally. 23 hours later the procedure is repeated and 60 minutes later the guinea-pigs are challenged with nebulised saline or ovalbumin (1% in saline) for 15 seconds. 24 hours after challenge the guinea-pigs are killed and the lungs are lavaged with warm saline. Total and differential cell counts are made.

5.2 Results.

Compounds within the scope of the invention, administered one hour before challenge, inhibit by at least 50% ovalbumin-induced eosinophilia in guinea-pigs which is measured 24 hours after challenge, at oral doses of about 1 to about 50 mg/kg, preferably about 1 to 10 mg/kg and inhaled doses of about 4 to 1000 μg/kg, preferably 0.4 to 50 μg/kg.

6. In Vitro Inhibitory Effects on TNF-a Release by Human Monocytes.

The effects of compounds on TNF-a production by human peripheral blood monocytes (PBMs) are examined as follows:

6.1. Preparation of Blood Leukocytes.

Blood is drawn from normal donors, mixed with dextran, and the erythrocytes allowed to sediment for 35 minutes at 37° C. Leukocytes are fractionated by centrifugation through a discontinuous (18, 20 and 22%) metrizamide gradient. The mononuclear cell fraction comprising 30–40% PBMs is suspended in HBSS and stored at 4° C. until use.

6.2. Measurement of TNFa.

Cells from the PBM-rich metrizamide fraction are spun down (200 g for 10 minutes at 20° C.), resuspended at $10^6$ PBMs/mL of medium; RPMI 1640 containing 1% v/v FCS, 50 U/mL penicillin and 50 mg/mL streptomycin (Gibco, U.K.), then plated out in 96 well plates at $2\times10^5$ cells/well. The medium (200 μL) is changed to remove any non-adherent cells and the remaining, adherent PBMs left in the incubator overnight (18 hours). One hour prior to challenge, the medium is changed to that containing compound for test or drug vehicle. Control treatments and compounds for test are assayed in quadruplicate wells. Compounds are tested within the concentration range of $3\times10^{-10}$ M to $3\times10^{-6}$ M. Medium (50 μL) with or without 10 ng/ml LPS (*E. Coli*, 055 B5 from Sigma, U.K.) is then added. The incubation is then continued for a further 4 hours. Cell supernatants are removed for storage at −20° C.

TNFa levels in cell supernatants are quantified using a standard sandwich ELISA technique. ELISA plates (Costar, U.K.) are coated overnight at 4° C. with 3 mg/mL polyclonal goat anti-human TNFa antibody (British Biotechnology, U.K.) in pH 9.9 bicarbonate buffer. Rabbit polyclonal anti-human TNFa antiserum (Janssen Biochimicha, Belgium) at 1/500 dilution is used as the second antibody and polyclonal goat anti-rabbit IgG horseradish peroxidase (Calbiochem, U.S.A.) at 1/8000 dilution is used as the detection antibody. Color development is measured by absorbance at 450 nm using a Titertek plate reader.

TNF-a levels are calculated by interpolation from a standard curve using recombinant human TNF-a (British Biotechnology U.K.)(0.125–8 ng/mL). Data (log-conc. vs. log-resp) are fitted by linear regression (p>0.99) using a Multicalc (Wallac Pharmacia, U.K.) software program. Basal TNF-a levels are less than 100 pg/mL whilst LPS stimulation of the PBMs increases TNF-a levels to 3–10 ng/mL.

6.3 Results.

Compounds within the scope of the invention produce 50% inhibition of LPS-induced TNF-a release from human PBMs at concentrations within the range of about $10^{-9}$ M to about $10^{-6}$ M., preferably about $10^{-9}$ M to about $10^{-8}$ M.

7. Inhibitory Effects of Compounds on Antigen-induced Bronchoconstriction in the Conscious Guinea-pig.

7.1. Sensitisation of Guinea-pigs and Measurement of Antigen-induced Bronchoconstriction.

Male, Dunkin-Hartley guinea-pigs (550–700 g) are sensitized as above. Specific airways resistance (SRaw) is measured in conscious animals by whole body plethysmography using a variation of the method of Pennock et al., (*J. Appl. Physiol.*, 46, 399, 1979). Test compounds or vehicle (lactose carrier) are instilled into the airways as dry powders through a metal gavage needle. 30 minutes later, the animals are injected with mepyramine (30 mg/kg i.p.) to prevent anaphylactic collapse and placed into the plethysmography chambers where SRaw is determined at 1 minute intervals. Resting SRaw is then determined. Animals are challenged with an aerosol of ovalbumin and SRaw is determined every 5 minutes for 15 minutes.

7.2. Results.

Compounds within the scope of the invention inhibit antigen-induced bronchoconstriction by up to 80% at doses of between about 1 to about 1000 μg/kg (i.t.), preferably about 1 to about 20 μg/kg (i.t.).

8. Inhibitory Effects of Compounds on Serum TNF-a Levels in LPS-challenged Mice.

8.1. Treatment of Animals and Measurement of Murine TNF-a.

Female Balb/c mice (age 6–8 weeks, weight 20–22 g from Charles River, U.K.) in groups of five or more animals are dosed p.o. with compounds suspended in 1.5% (w/v) carboxymethyl cellulose then challenged after a minimum period of 30 min with 30 mg of LPS i.p. After 90 min the animals are killed by $CO_2$ asphyxiation and bled by cardiac puncture. Blood is allowed to clot at 4° C., centrifuged (12,000 g for 5 minutes) and serum taken for TNF-a analysis.

TNF-a levels are measured using a commercially available murine TNF-a ELISA kit, purchased from Genzyme (Cat. no. 1509.00), as recommended by the manufacturer. Values for TNF-a are calculated from a recombinant murine TNF-a standard curve.

8.2 Results.

Compounds within the scope of the invention inhibit LPS-induced serum TNF-a at doses between about 10 and about 10,000 mg/kg, preferably about 10 to about 250 μg/kg.

The value of the compounds of the invention is enhanced by their very low mammalian toxicity levels.

The following Composition Examples illustrate pharmaceutical compositions according to the present invention.

Composition Example 1

N-(2,6-Difluorophenyl)-3-cyclopentyloxy-4-methoxybenzamide (1 g) (mean particle size 3.5 microns) and lactose (99 g) (mean particle size 72 microns) were blended together for 30 minutes in a mechanical shaker/mixer. The resulting blend was filled, to a fill weight of 25 mg, into No. 3 hard gelatin capsules, to give a product suitable for use, for example, with a dry powder inhaler.

Composition Example 2

N-(3,5-Dichloropyrid-4-yl)-3-cyclopentyloxy-4-methoxybenzamide (1 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatin capsules, to give a product suitable for use, for example, with a dry powder inhaler.

Composition Example 3

No. 2 size gelatin capsules each containing:

| | |
|---|---|
| N-(3,5-dichloropyrid-4-yl)-3-cyclopentyloxy-4-methoxybenzamide | 20 mg |
| lactose | 100 mg |
| starch | 60 mg |
| dextrin | 40 mg |
| magnesium stearate | 1 mg | are prepared in accordance with the usual procedure.

Composition Example 4

N-(3,5-Dichloropyrid-4-yl)-3-cyclopentyloxy-4-(methylthio)benzamide (1 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatin capsules, to give a product suitable for use, for example, with a dry powder inhaler.

Composition Example 5

No. 2 size gelatin capsules each containing:

| | |
|---|---|
| N-(3,5-dichloropyrid-4-yl)-3-cyclopentyloxy-4-(methylthio)benzamide | 20 mg |
| lactose | 100 mg |
| starch | 60 mg |
| dextrin | 40 mg |
| magnesium stearate | 1 mg | are prepared in accordance with the usual procedure.

Composition Example 6

(±)-N-(3,5-dichloropyrid-4-yl)-3-cyclopent-2-enyloxy-4-methoxybenzamide (1 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatin capsules, to give a product suitable for use, for example, with a dry powder inhaler.

Composition Example 7

No. 2 size gelatin capsules each containing:

| | |
|---|---|
| (±)-N-(3,5-dichloropyrid-4-yl)-3-cyclopent-2-enyloxy-4-methoxybenzamide | 20 mg |
| lactose | 100 mg |
| starch | 60 mg |
| dextrin | 40 mg |
| magnesium stearate | 1 mg | are prepared in accordance with the usual procedure.

Composition Example 8

N-(3,5-Dichloropyrid-4-yl)-3-cyclopentyloxy-4-difluoromethoxybenzamide (1 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatin capsules, to give a product suitable for use, for example, with a dry powder inhaler.

Composition Example 9

No. 2 size gelatin capsules each containing:

| | |
|---|---|
| N-(3,5-dichloropyrid-4-yl)-3-cyclopentyloxy-4-difluoromethoxybenzamide | 20 mg |
| lactose | 100 mg |
| starch | 60 mg |
| dextrin | 40 mg |
| magnesium stearate | 1 mg | are prepared in accordance with the usual procedure.

Composition Example 10

3-Cyclopentyloxy-4-methoxyphenyl-2',6'-dichlorobenzyl ketone (1 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatin capsules, to give a product suitable for use, for example, with a dry powder inhaler.

Composition Example 11

3-Cyclopentyloxy-4-methoxyphenyl-3,5-dichloropyrid-4-ylmethyl ketone (1 g) (mean particle size 3.5 microns) and lactose (99 g) (mean particle size 72 microns) are blended together for 30 minutes in a mechanical shaker/mixer. The resulting blend is filled to a fill weight of 25 mg, into No. 3 hard gelatin capsules, to give a product suitable for use, for example, with a dry powder inhaler.

Composition Example 12

No. 2 size gelatin capsules each containing:

| | |
|---|---|
| 3-cyclopentyloxy-4-methoxyphenyl-2',6'-dichlorobenzyl ketone | 20 mg |
| lactose | 100 mg |
| starch | 60 mg |
| dextrin | 40 mg |
| magnesium stearate | 1 mg | are prepared in accordance with the usual procedure.

Composition Example 13

No. 2 size gelatin capsules each containing:

| | |
|---|---|
| 3-cyclopentyloxy-4-methoxyphenyl-3,5-dichloropyrid-4-ylmethyl ketone | 20 mg |
| lactose | 100 mg |
| starch | 60 mg |
| dextrin | 40 mg |
| magnesium stearate | 1 mg | are prepared in accordance with the usual procedure.

Composition Example 14

3-Cyclopentyloxy-4-methoxyphenyl-2',6'-dichlorobenzyl ketone (1 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatin capsules, to give a product suitable for use, for example, with a dry powder inhaler.

Composition Example 15

3-Cyclopentyloxy-4-methoxyphenyl 3,5-dichloropyrid-4-ylmethyl ketone (1 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatin capsules, to give a product suitable for use, for example, with a dry powder inhaler.

Composition Example 16

No. 2 size gelatin capsules each containing:

| | |
|---|---|
| 3-cyclopentyloxy-4-methoxyphenyl-2',6'-dichlorobenzyl ketone | 20 mg |
| lactose | 100 mg |
| starch | 60 mg |
| dextrin | 40 mg |
| magnesium stearate | 1 mg | are prepared in accordance with the usual procedure.

Composition Example 17

No. 2 size gelatin capsules each containing:

| | |
|---|---|
| 3-cyclopentyloxy-4-methoxyphenyl-3,5-dichloropyrid-4-ylmethyl ketone | 20 mg |
| lactose | 100 mg |
| starch | 60 mg |
| dextrin | 40 mg |
| magnesium stearate | 1 mg | are prepared in accordance with the usual procedure.

Composition Example 18

3-Cyclopentyloxy-4-methoxyphenyl-2,6-dichlorobenzamide (1 g) (mean particle size 3.5 microns) and lactose (99 g) (mean particle size 72 microns) are blended together for 30 minutes in a mechanical shaker/mixer. The resulting blend is filled. to a fill weight of 25 mg, into No. 3 hard gelatin capsules, to give a product suitable for use, for example, with a dry powder inhaler.

Similar compositions are prepared from other compounds of formula I.

Composition Example 19

No. 2 size gelatin capsules each containing:

| | |
|---|---|
| 3-cyclopentyloxy-4-methoxyphenyl-2,6-dichlorobenzamide | 20 mg |
| lactose | 100 mg |
| starch | 60 mg |
| dextrin | 40 mg |
| magnesium stearate | 1 mg | are prepared in accordance with the usual procedure.

Similar compositions are prepared from other compounds of formula I.

Composition Example 20

N-(3,5-difluoropyrid-4-yl)-3-cyclopentyloxy-4-methoxybenzamide (1 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatin capsules. to give a product suitable for use, for example, with a dry powder inhaler.

Composition Example 21

No. 2 size gelatin capsules each containing:

| | |
|---|---|
| N-(3,5-difluoropyrid-4-yl)-3-cyclopentyloxy-4-methoxybenzamide | 20 mg |
| lactose | 100 mg |
| starch | 60 mg |
| dextrin | 40 mg |
| magnesium stearate | 1 mg | are prepared in accordance with the usual procedure.

The present invention may be embodied in other specific forms without departing from the spirit or essential attributes thereof.

What is claimed is:
1. A compound of formula I

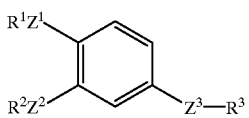

wherein
$R^1$ is optionally substituted lower alkyl;
$R^2$ is optionally halo substituted $C_3$–$C_{15}$ alkyl, optionally substituted alkenyl, or alkyl substituted by cycloalkyl or cycloalkenyl and further optionally substituted by halo;
$R^3$ is optionally substituted heteroaryl or optionally substituted aryl wherein said aryl is phenyl or naphthyl, either of which may be substituted with one or more aryl group substituents which may be the same or different, selected from the group consisting of hydrogen, alkyl, aryl, aralkyl, hydroxy, hydroxyalkyl, alkoxy, aryloxy, aralkoxy, carboxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, arylthio, aralkylthio, $Y^1Y^2N—$, $Y^1Y^2NCO—$ or $Y^1Y^2NSO_2—$, where $Y^1$ and $Y^2$ are independently selected from the group consisting of hydrogen, alkyl, aryl, and aralkyl;
Z, $Z^1$ and $Z^2$ are independently oxygen or sulfur; and
$Z^3$ is —CZNH—, or
an N-oxide thereof or a pharmaceutically acceptable salt thereof.
2. A compound of formula

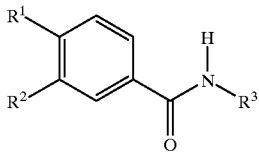

wherein
$R^1$ is $C_1$–$C_4$-alkoxy which is completely or partially substituted by fluorine,
$R^2$ is $C_3$–$C_5$-cycloalkylmethoxy, and
$R^3$ is 2-bromophenyl, 2,6-dichloro-4-ethoxycarbonylphenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2,3,5,6-tetrafluoropyrid-4-yl, 3-chloro-2,5,6-trifluoropyrid-4-yl, or
an oxide thereof or a pharmaceutically acceptable salt thereof.
3. The compound according to claim 1 wherein $Z^1$ and $Z^2$ are oxygen, or $Z^1$ is sulfur and $Z^2$ is oxygen.
4. The compound according to claim 1 wherein $R^1$ is lower alkyl substituted by halo.
5. The compound according to claim 4 wherein $R^1$ is substituted by one or more halo on positions of $R^1$ that are adjacent to the position of $R^1$ that is attached to $Z^1$.
6. The compound according to claim 1 wherein $R^3$ is phenyl substituted on the 2-position or on both the 2- and 6-positions.
7. The compound according to claim 1 wherein $R^3$ is heteroaryl substituted on one or both of the positions adjacent to the position of $R^3$ that is attached to $Z^3$.
8. The compound according to claim 1 wherein $R^3$ is a 3,5-dihalo-pyrid-4-yl.
9. The compound according to claim 1 wherein $R^2$ is alkenyl, $C_3$–$C_{15}$ alkyl, or alkyl substituted by cycloalkyl or cycloalkenyl and further optionally substituted by halo.
10. The compound according to claim 1 wherein $R^3$ is substituted aryl or substituted heteroaryl, each of which is substituted by aralkoxy, aralkylthio, carboxy, aralkyloxycarbonyl, $Y^1Y^2N—$, $Y^1Y^2NCO—$ or $Y^1Y^2NSO_2—$ where $Y^1$ and $Y^2$ are independently hydrogen, alkyl, aryl or aralkyl, provided that one or both of $Y^1$ and $Y^2$ is aryl or aralkyl.
11. The compound according to claim 1 which is:
N-(2,6-difluorophenyl)-3-butoxy-4-methoxybenzamide;
N-(2,6-difluorophenyl)-3-propoxy-4-methoxybenzamide;
N-(3,5-dichloropyrid-4-yl)-3-butoxy-4-methoxybenzamide;
N-(3,5-dibromopyrid-4-yl)-3-butoxy-4-methoxybenzamide;
N-(2,6-dichloropyrid-4-yl)-3-nonyloxy-4-methoxybenzamide;
N-(3,5-dichloropyrid-4-yl)-3-isopropylthio-4-methoxybenzamide;
3-(3-methyl-2-butenyloxy)-N-(3,5-dichloropyrid-4-yl)-4-methoxybenzamide;
N-(3,5-dichloropyrid-4-yl)-3-isopropoxy-4-methoxybenzamide;
3-tert-butoxy-N-(3,5-dichloropyrid-4-yl)-4-methoxybenzamide;
N-(3,5-dichloropyrid-4-yl)-4-methoxy-3-(pent-3-yloxy)benzamide;
N-(3,5-difluoropyrid-4-yl)-3-isopropoxy-4-difluoromethoxybenzamide;
N-(3,5-difluoro-1-oxido-4-pyridinio)-3-isopropoxy-4-difluoromethoxybenzamide;
N-(3,5-dichloropyrid-4-yl)-3-isopropoxy-4-difluoromethoxybenzamide;
N-(3,5-dichloro-1-oxido-4-pyridinio)-3-isopropoxy-4-difluoromethoxybenzamide;
N-(3,5-dichloropyrid-4-yl)-3-isopropoxy-4-(methylthio)benzamide;
N-(3,5-difluoropyrid-4-yl)-3-isopropoxy-4-(methylthio)benzamide;
N-(3,5-dichloropyrid-4-yl)-3-(pent-3-yloxy)-4-(methylthio)benzamide; or
an N-oxide thereof or a pharmaceutically acceptable salt thereof.
12. A compound which is 3-cyclopentylmethoxy-N-(3,5-dichloropyrid-4-yl)-4-methoxybenzamide, or an N-oxide thereof or a pharmaceutically acceptable salt thereof.
13. A compound which is 3-cyclopropylmethoxy-N-(3,5-dichloropyrid-4-yl)-4-methoxybenzamide, or an N-oxide thereof or a pharmaceutically acceptable salt thereof.
14. A pharmaceutical composition comprising an effective amount of the compound according to claim 1 and a pharmaceutically acceptable carrier.
15. A method for treating a disease state capable of being modulated by inhibiting production of TNF comprising administering to a patient suffering from said disease state an effective amount of the compound according to claim 1.
16. The method of claim 15 wherein the disease state is an inflammatory disease or autoimmune disease.

17. The method of claim 16 wherein the disease state is selected from the group consisting of joint inflammation, arthritis, rheumatoid arthritis, rheumatoid spondylitis and osteoarthritis, sepsis, septic shock, gram negative sepsis, toxic shock syndrome, acute respiratory distress syndrome, asthma, bone resorption diseases, reperfusion injury, graft vs host reaction, allograft rejection malaria, myalgias, HIV, AIDS, cachexia, Crohn's disease, ulcerative colitis, pyresis, systemic lupus erythematosus, multiple sclerosis, type I diabetes mellitus, psoriasis, Beghet's disease, anaphylactoid purpura nephritis, chronic glomerulonephritis, inflammatory bowel disease and leukemia.

18. The method of claim 17 wherein the disease state is joint inflammation.

19. A method for treating a disease state capable of being modulated by inhibiting production of cyclic AMP phosphodiesterase comprising administering to a patient suffering from said disease state an effective amount of the compound according to claim 1.

20. The method of claim 9 wherein the disease state is a pathological condition associated with a function of cyclic AMP phophodiesterase, eosinophil accumulation or a function of the eosinophil.

21. The method of claim 20 wherein the pathological condition is asthma, atopic dermatitis, urticaria, allergic rhinitis, psoriasis, rheumatic arthritis, ulcerative colitis, Crohn's disease, adult respiratory distress syndrome, diabetes insipidus, keratosis, dermatitis, cerebral senility, multi-infarct dementia, senile dementia, memory impairment associated with Parkinson's disease, cardiac arrest, stroke and intermittent claudication.

22. The method of claim 21 wherein the pathological condition is asthma.

* * * * *